(12) United States Patent
Vanura et al.

(10) Patent No.: US 10,280,156 B2
(45) Date of Patent: May 7, 2019

(54) HETEROAROMATIC CHALCONE DERIVATIVES AND THEIR MEDICAL USE

(71) Applicants: Medizinische Universität Wien, Vienna (AT); Universität Wien, Vienna (AT)

(72) Inventors: Katrina Vanura, Vienna (AT); Ulrich Jäger, Vienna (AT); Thomas Erker, Vienna (AT); Gerda Brunhofer-Bolzer, Vienna (AT)

(73) Assignees: Medizinische Universität Wien, Vienna (AT); Universität Wien, Vienna (AT)

( * ) Notice: Subject to any disclaimer, the term of this patent is extended or adjusted under 35 U.S.C. 154(b) by 0 days.

(21) Appl. No.: 15/507,006

(22) PCT Filed: Aug. 28, 2015

(86) PCT No.: PCT/EP2015/069758
§ 371 (c)(1),
(2) Date: Feb. 27, 2017

(87) PCT Pub. No.: WO2016/030510
PCT Pub. Date: Mar. 3, 2016

(65) Prior Publication Data
US 2017/0253583 A1 Sep. 7, 2017

(30) Foreign Application Priority Data

Aug. 28, 2014 (EP) ..................... 14182679

(51) Int. Cl.
| | |
|---|---|
| *C07D 209/10* | (2006.01) |
| *C07D 307/80* | (2006.01) |
| *C07D 317/08* | (2006.01) |
| *C07D 333/56* | (2006.01) |
| *C07D 409/04* | (2006.01) |
| *C07C 49/255* | (2006.01) |
| *C07C 49/577* | (2006.01) |
| *A61K 31/404* | (2006.01) |
| *A61P 35/00* | (2006.01) |
| *A61K 31/381* | (2006.01) |
| *A61K 31/423* | (2006.01) |
| *A61K 31/4184* | (2006.01) |
| *A61K 31/343* | (2006.01) |
| *A61K 31/416* | (2006.01) |
| *A61K 31/33* | (2006.01) |
| *C07C 49/20* | (2006.01) |

(52) U.S. Cl.
CPC ............ *C07D 409/04* (2013.01); *A61K 31/33* (2013.01); *A61K 31/343* (2013.01); *A61K 31/381* (2013.01); *A61K 31/404* (2013.01); *A61K 31/416* (2013.01); *A61K 31/4184* (2013.01); *A61K 31/423* (2013.01); *A61P 35/00* (2018.01); *C07C 49/20* (2013.01); *C07D 209/10* (2013.01); *C07D 307/80* (2013.01); *C07D 317/08* (2013.01); *C07D 333/56* (2013.01)

(58) Field of Classification Search
CPC .. C07D 209/10; C07D 307/80; C07D 317/08; C07D 333/56; C07D 409/04; A61K 31/404; A61K 31/416; A61K 31/4184; A61K 31/423; A61K 31/343; A61K 31/381; A61P 35/00
USPC ......... 548/152, 207, 217, 241, 304.4, 360.1, 548/452; 549/49, 50, 434, 402, 428, 462; 514/366, 373, 375, 379, 394, 405, 415, 514/443, 469
See application file for complete search history.

(56) References Cited

U.S. PATENT DOCUMENTS 8,324,231 B2 * 12/2012 Koltun ................ C07D 403/04
514/272

FOREIGN PATENT DOCUMENTS

| | | |
|---|---|---|
| EP | 01748044 | 1/2007 |
| JP | 2008308496 | 12/2008 |
| WO | WO 2012/013725 | 2/2012 |

OTHER PUBLICATIONS

Das et al., Journal of Toxicology, vol. 2016, pp. 1-14.*
Kamal et al. Expert Opin. Drug Discov. (2013) 8(3):289-304.*
Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Wolff Manfred E. "Burger's Medicinal Chemistry, 5ed, Part 1", John Wiley & Sons, 1995, pp. 975-977.*
(Continued)

*Primary Examiner* — Venkataraman Balasubramanian
(74) *Attorney, Agent, or Firm* — Parker Highlander PLLC

(57) ABSTRACT

The present invention relates to heteroaromatic chalcone derivatives, particularly the compounds of formula (I) as described and defined herein, pharmaceutical compositions comprising these compounds, and their medical use, including their use in the treatment or prevention of cancer and, in particular, in the treatment or prevention of hematologic malignancies.

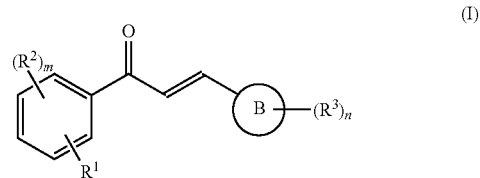

14 Claims, 11 Drawing Sheets

(56) References Cited

OTHER PUBLICATIONS

Figure 1:
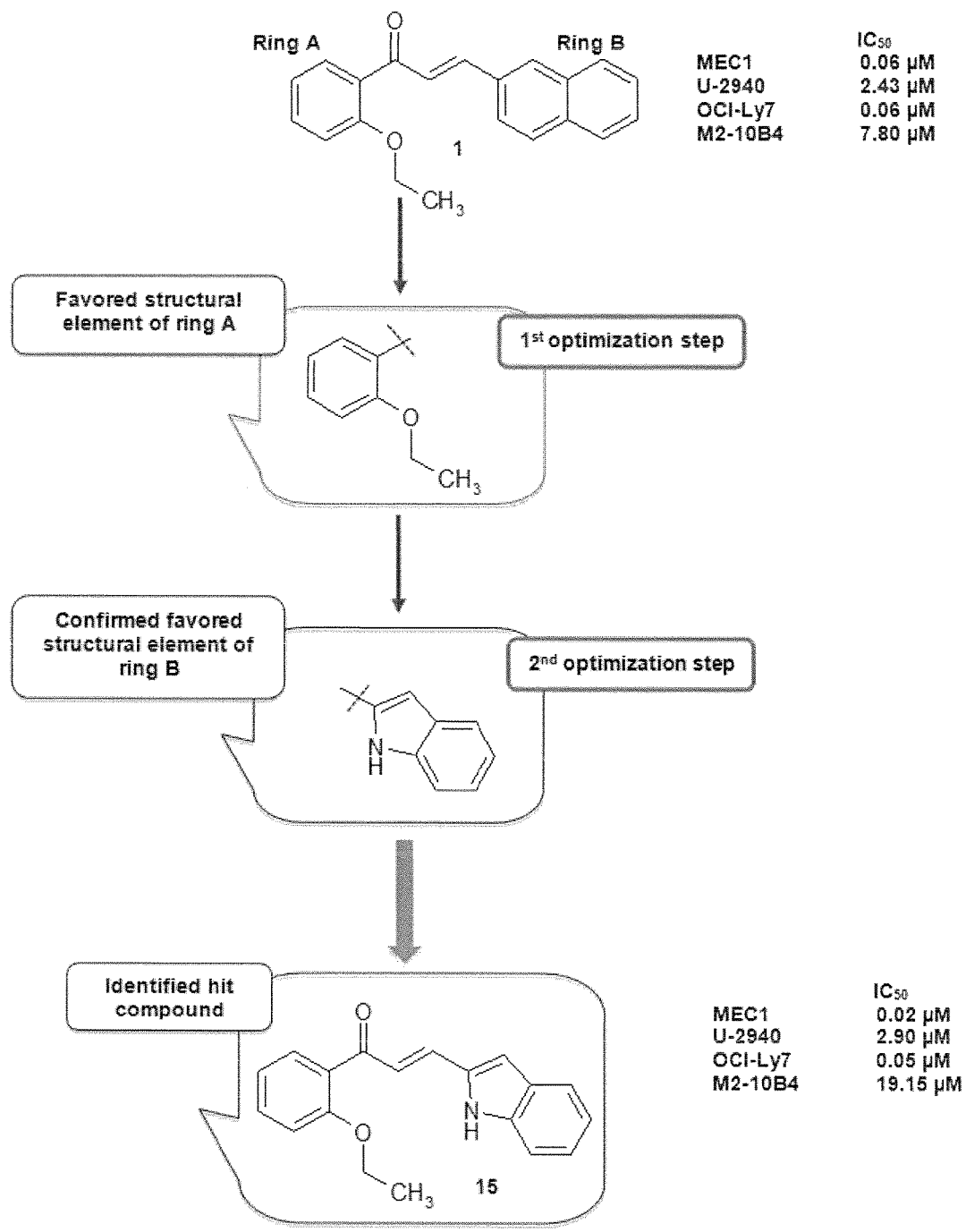

Banker, G.S. et al, "Modern Pharmaceutices, 3ed.", Marcel Dekker, New York. 1996, pp. 451 and 596.*
Guo et al. Gaodeng Xuexiao Huaxue Xuebao (2006), 27(9), 1660-1663. CAPLUS Abstract provided.*
Pccompound-selected items 2, Create Date Dec. 5, 2007 to Dec. 3, 2011.*
Pccompound-selected items 22, Create Date May 29, 2009 to Dec. 1, 2013.*
Pccompound-list-5, Create Date Jun. 10, 2009 to Jun. 23, 2014.*
Pccompound-selected items 13, Create Date Jul. 29, 2005 to Aug. 16, 2014.*
Pccompound-selected items 4, Create Date Dec. 5, 2007 to Dec. 4, 2013.*
Pccompound-list-16, Create Date Oct. 25, 2006 to Aug. 20, 2012.*
Abdel-Halim et al., "Trisubstituted and tetrasubstituted pyrazolines as a novel class of cell-growth inhibitors in tumor cells with wild type p53," *Bioorg. Med. Chem.*, 21:7343-7356, 2013.
Andotra et al., "Synthesis of 1,2,3,4-tetrahydro-2,4-dioxo-7-(2,4-dialkoxyphenyl)-5-subsituted-phenyl-5H-pyrano-[2,3-d]-pyrimidines and 3-(2,4-dialkoxyphenyl)-5-substituted-phenylisoxazoles," *J. Indian Chem. Soc.*, 83:509-512, 2006.
Barot and Desai, "Synthesis of Bioactive Isothiazoline Derivatives," *Asian J. Chem.*, 21(8):6091-6094, 2009.
Batagin-Neto and Lavarda, "The correlation between electronic structure and antimalarial activity of alkoxylated and hydroxylated chalcones," *Med. Chem. Res.*, 23:580-586, 2014.
Boumedjel et al., "Antimitotic and Antiproliderative Activities of Chalcones: Forward Structure-Activity Relationship," *J. Med. Chem.*, 51:2307-2310, 2008.

Cheng et al., "Synthesis and cytotoxic, anti-inflammatory, and anti-oxidant activities of 2',5'-dialkylchalcones as cancer chemopreventive agents," *Bioorg. Med. Chem.*, 16, 7270-7276, 2008.
Extended European Search Report issued in corresponding European Patent Application No. 14182679.2-1462, dated Nov. 12, 2014.
Goodarzi et al., "Binary classification of chalcone derivatives with LDS or KNN based on their antileishmanial activity and molecular descriptors selected using the Successive Projections Algorithm feature-selection technique," *Eur. J. Pharm. Sci.*, 51:183-195, 2014.
International Search Report issued in corresponding PCT Application No. PCT/EP2015/069758, dated Nov. 9, 2015.
Khunt et al., "Synthesis and 3D-QSAR Analysis of 2-Chloroquinoline Derivatives as $H_{37}RV$ MTB Inhibitors," *Chem. Biol. Drug Des.*, 82:669-684, 2013.
Lo et al., "2'-Ethoxy-5'-Methoxy-2-(5-Methylthienyl)Chalcone Inhibits Collagen-Induced Protein Tyrosine Phosphorylation and Thromboxane Formation during Platelet Aggregation and Adhesion," *Pharmacology*, 84:145-152, 2009.
Mielcke et al., "Activity of novel quinoxaline-derived chalcones on in vitro glioma cell proliferation," *Eur. J. Med. Chem.*, 48:255-264, 2012.
Sriwilaijaroen et al., "Plasmepsin II inhibitory activity of alkoxylated and hydroxylated chalcones," *Southeast Asian J. Trop. Med. Public Health*, 37(4):607-612, 2006.
Wai Mai et al., "Chalcones with electron-withdrawing and electron-donating substitutents: Anticancer activity against TRAIL resistant cancer cells, structure-activity relationship analysis and regulation of apoptotic proteins," *Eur. J. Med. Chem.*, 77:378-387, 2014.

* cited by examiner

A)

B)

C)

A)

B)

c)

A)

B)

c)

HETEROAROMATIC CHALCONE DERIVATIVES AND THEIR MEDICAL USE

This application is a national phase application under 35 U.S.C. § 371 of International Application No. PCT/EP2015/069758, filed Aug. 28, 2015, which claims benefit of European Application No. 14182679.2, filed Aug. 28, 2014, the entire contents of each of which are hereby incorporated by reference.

The present invention relates to heteroaromatic chalcone derivatives, particularly the compounds of formula (I) as described and defined herein, pharmaceutical compositions comprising these compounds, and their medical use, including their use in the treatment or prevention of cancer and, in particular, in the treatment or prevention of hematologic malignancies.

Hematologic malignancies are a highly diverse group of cancers, which affect bone marrow, blood and the lymph nodes, and are also referred to as hematological cancer. They rank just outside the top ten list of cancers worldwide (GLOBOCAN, WHO, http://globocan.iarc.fr/), and are expected to constitute 9% of cancers and to account for 9.4% of deaths from cancers in the USA in 2013 (The Leukemia & Lymphoma Society, Facts 2013). Roughly 75% of these neoplasms are of lymphoid, the rest is of myeloid origin, incidence rates being about ~20 for lymphoid and ~7 for myeloid entities, respectively, per 100,000 persons per year in Western countries (The Leukemia & Lymphoma Society, Facts 2013; Jayasekara H et al. *Leukemia Lymphoma* 2010, 51, 456-468; Sant M et al. *Blood* 2010, 116, 3724-34; Cancer Facts & Figures 2013, *American Cancer Society*, 2013, 65). Acute diseases (leukemias and aggressive lymphomas) can be cured in approximately half of the patients, while the other patients die from their disease. Chronic leukemias and indolent lymphomas can be well controlled for years in most cases. However, the cure rate of these patients is low and the course of the disease is characterized by frequent recurrence.

Among lymphoid malignancies, mature B-cell neoplasms not only constitute the largest proportion of diseases (52%), they also show the highest incidence rates, 19.14 per 100,000 in Europe with similar numbers reported from other Western countries (Sant M et al. *Blood* 2010, 116, 3724-34), and are predominately diagnosed in elderly persons (Jayasekara H et al. *Leukemia Lymphoma* 2010, 51, 456-468). Due to the diversity of these malignancies, biology and pathological characteristics are highly heterogeneous as is clinical presentation and behavior, and, subsequently, therapeutic requirements. Conventional therapeutic regimens include chemotherapy, chemo-immunotherapy, and hematopoietic stem cell transplantation, experimental treatments comprise small and targeting molecules. Still, 30-50% of patients are resistant to treatment, progress rapidly, and die of their disease. Novel first line therapies are often very effective with response rates from 70-90%, however, many patients relapse or develop resistant disease. For these refractory patients, and for patients characterized by adverse factors, novel treatment opportunities and novel, targeted therapies are urgently needed.

One of the approaches for the development of novel anti-cancer drugs is the assessment of naturally occurring compounds for cancer therapy. In the context of the present invention, the chalcone scaffold has been used as a template for the structure-activity guided development of selective cytotoxic compounds towards B-cell neoplasms.

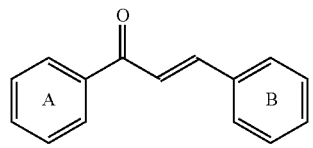

General structure of chalcones

Chemically, chalcones are biosynthetic precursors of flavonoids and both natural as well as synthetic derivatives have shown biologic activity in cancer cells (Henmi K et al. *Biol Pharm Bull* 2009, 32, 1109-13; Kong Y et al. *Bioorg Med Chem* 2010, 18, 971-977; Navarini A L F et al. *Eur J Med Chem* 2009, 44, 1630-1637; Yang X et al. *Bioorg Med Chem Lett* 2009, 19, 4385-4388; Szliszka E et al. *Int J Mol Sci* 2009, 11, 1-13; Cuendet, M et al. *Cancer Prevention Research* 2010, 3(2), 221-232). Recent studies have shown that chalcone derivatives exhibit cytotoxic activity in different tumor cell lines including hematological malignancies. (E)-α-Benzylthiochalcones are able to significantly inhibit proliferation of K562, a BCR-ABL positive chronic myeloid leukemia cell line (Reddy M V R et al. *Bioorg Med Chem* 2010, 18, 2317-2326). Nevertheless, little is known about the mode of action of chalcone-based compounds. Their apoptosis inducing properties seemed to be mediated by interference in microtubule formation (Bhat B A et al. *BioorgMed Chem Lett* 2005, 15, 3177-3180; Ducki S et al. *BioorgMed Chem Lett* 1998, 8, 1051-1056; Ducki S et al. *BioorgMed Chem* 2009, 17, 7698-7710; Edwards M L et al. *J Med Chem* 1990, 33, 1948-1954; Hsu Y L et al. *Food Chem Toxicol* 2006, 44, 704-713; Lawrence N J et al. *Bioorg Med Chem Lett* 2006, 16, 5844-5848; Liu X et al. *Bioorg Med Chem* 2006, 14, 153-163; Peyrot V et al. *J Biol Chem* 1989, 264, 21296-21301; Tu H-Y et al. *Bioorg Med Chem* 2010, 18, 2089-2098), inhibition of nuclear factor kappa B (NF-κB) (Srinivasan B et al. *J Med Chem* 2009, 52, 7228-7235) and/or depletion of mitochondrial glutathione (Navarini A L F et al. *Eur J Med Chem* 2009, 44, 1630-1637). Certain chalcone derivatives and, in some cases, their therapeutic use have further been described, e.g., in: Ivanova A et al. *In Vivo* 2008, 22(3), 379-84; Gutteridge C E et al. *Bioorg Med Chem Lett* 2006, 16(21), 5682-6; Chiaradia L D et al. *Bioorg Med Chem Lett* 2008, 18(23), 6227-30; Cabrera M et al. *Bioorg Med Chem* 2007, 15(10), 3356-67; Nam N H et al. *Eur J Med Chem* 2003, 38(2), 179-87; Sahu N K et al. *Curr Med Chem* 2012, 19(2), 209-25; Batovska D I et al. *Curr Clin Pharmacol* 2010, 5(1), 1-29; Lo H M et al. *Pharmacology* 2009, 84(3), 145-152; Goodarzi M et al. *Eur J Pharm Sci* 2014, 51, 189-195; Abdel-Halim M et al. *Bioorg Med Chem* 2013, 21(23), 7343-7356; Khunt R C et al. *Chem Biol Drug Des* 2013, 82(6), 669-684; Batagin-Neto A et al. *Med Chem Res* 2014, 23(2), 580-586; Andotra C S et al. *J Indian Chem Soc* 2006, 83(5), 509-512; Barot V M et al. *Asian J Chem* 2009, 21(8), 6091-6094; Sriwilaijaroen N et al. *Southeast Asian J Trop Med Public Health* 2006, 37(4), 607-612; EP-A-1748044; JP-A-2008/308496; and WO 2010/019861.

In Cheng J H et al. *Bioorg Med Chem* 2008, 16(15), 7270-7276, various 2',5'-dialkoxy-2-(5-methylthienyl) chalcones are described as potential cancer chemopreventative agents. These compounds, however, have a different chemical scaffold than the heteroaromatic chalcone derivatives of formula (I) provided in accordance with the present invention.

Particularly potent chalcone derivatives, including the compound 3-(2-napthyl)-1-(2-ethoxyphenyl)-2-propen-1-one, have furthermore been described for the treatment of hematological cancer in WO 2012/013725. However, there is still an urgent need for further therapeutics against hematological cancer.

In the context of the present invention, it has surprisingly been found that the heteroaromatic chalcone derivatives of formula (I) as described and defined herein are particularly effective in the therapy of hematological cancer. The present invention thus solves the problem of providing novel and improved therapeutic agents for the medical intervention in cancer, particularly in hematological cancer.

Accordingly, the present invention provides a compound of the following formula (I)

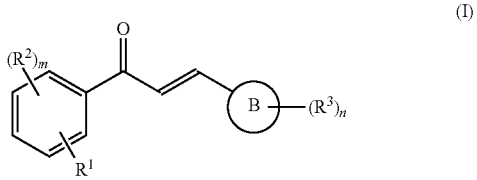

(I)

or a pharmaceutically acceptable salt, solvate or prodrug thereof.

In formula (I), $R^1$ is $C_{2-6}$ alkoxy. Preferably $R^1$ is $C_{2-4}$ alkoxy (e.g., ethoxy, n-propoxy, isopropoxy, n-butoxy, isobutoxy, sec-butoxy, or tert-butoxy), more preferably $R^1$ is linear $C_{2-4}$ alkoxy (e.g., ethoxy, n-propoxy, or n-butoxy), even more preferably $R^1$ is ethoxy or n-propoxy, and yet even more preferably $R^1$ is ethoxy. It is furthermore preferred that $R^1$ (including any of the aforementioned preferred groups $R^1$) is in ortho-position with respect to the carbonyl group (i.e., that $R^1$ is attached to the phenyl ring in ortho-position with respect to the carbonyl group that is also attached to the phenyl ring). Accordingly, it is most preferred that $R^1$ is ortho-ethoxy.

Each $R^2$ is independently selected from $C_{1-6}$ alkyl, $C_{2-6}$ alkenyl, $C_{2-6}$ alkynyl, —OH, —O($C_{1-6}$ alkyl), —O($C_{1-6}$ alkyl)-OH, —O($C_{1-6}$ alkyl)-O($C_{1-6}$ alkyl), —SH, —S($C_{1-6}$ alkyl), —S($C_{1-6}$ alkyl)-SH, —S($C_{1-6}$ alkyl)-S($C_{1-6}$ alkyl), —NH$_2$, —NH($C_{1-6}$ alkyl), —N($C_{1-6}$ alkyl)($C_{1-6}$ alkyl), halogen, —CF$_3$, —CN, —NO$_2$, —N$_3$, —CHO, —CO—($C_{1-6}$ alkyl), —COOH, —CO—O—($C_{1-6}$ alkyl), —O—CO—($C_{1-6}$ alkyl), —CO—NH$_2$, —CO—NH($C_{1-6}$ alkyl), —CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —SO$_2$—NH$_2$, —SO$_2$—NH($C_{1-6}$ alkyl), —SO$_2$—N($C_{1-6}$ alkyl)($C_{1-6}$ alkyl), —NH—SO$_2$—($C_{1-6}$ alkyl), or —N($C_{1-6}$ alkyl)-SO$_2$—($C_{1-6}$ alkyl). Preferably, each $R^2$ is independently selected from $C_{1-6}$ alkyl, $C_{2-6}$ alkenyl, $C_{2-6}$ alkynyl, —OH, —O($C_{1-6}$ alkyl), —O($C_{1-6}$ alkyl)-OH, —O($C_{1-6}$ alkyl)-O($C_{1-6}$ alkyl), —SH, —S($C_{1-6}$ alkyl), —S($C_{1-6}$ alkyl)-SH, —S($C_{1-6}$ alkyl)-S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. More preferably, each $R^2$ is independently selected from $C_{1-4}$ alkyl, halogen, —CF$_3$, —CN, —OH, —O($C_{1-4}$ alkyl), —NH$_2$, —NH($C_{1-4}$ alkyl), or —N($C_{1-4}$ alkyl)($C_{1-4}$ alkyl).

m is an integer of 0 to 4. Accordingly, the phenyl ring comprised in the compound of formula (I) has 0 to 4 substituents $R^2$. Preferably m is an integer of 0 to 3, more preferably m is 0, 1 or 2, even more preferably m is 0 or 1, and most preferably m is 0. It is to be understood that, if m is 0, the phenyl ring does not carry any substituents $R^2$, i.e., the corresponding ring atoms are in that case substituted with hydrogen instead of $R^2$.

B is benzoheteroaryl, wherein the heteroaryl moiety comprised in said benzoheteroaryl is a monocyclic heteroaryl moiety having 5 ring atoms, wherein 1 or 2 ring atoms are each independently selected from oxygen, sulfur or nitrogen and the other ring atoms are carbon atoms. For example, B may be selected from indolyl, isoindolyl, benzimidazolyl, benzofuranyl, isobenzofuranyl, indazolyl, benzothiophenyl, benzothiazolyl, benzoxazolyl, benzisoxazolyl, or benzo[b]thienyl. Preferably, B is benzoheteroaryl, wherein the heteroaryl moiety comprised in said benzoheteroaryl is a monocyclic heteroaryl moiety having 5 ring atoms, wherein 1 or 2 ring atoms are each independently selected from oxygen, sulfur or nitrogen and the other ring atoms are carbon atoms, and further wherein the benzoheteroaryl is attached to the remainder of the compound of formula (I), i.e. to the 2-propen-1-one moiety comprised in the compound of formula (I), via the heteroaryl moiety comprised in said benzoheteroaryl. More preferably, B is selected from indolyl (e.g., 1H-indol-2-yl, 1H-indol-3-yl or 1H-indol-5-yl), benzo[b]thienyl (e.g., 2-benzo[b]thienyl, 3-benzo[b]thienyl or 5-benzo[b]thienyl), or benzofuranyl (e.g., benzofuran-2-yl, benzofuran-3-yl or benzofuran-5-yl). Even more preferably, B is selected from 1H-indol-2-yl, 1H-indol-3-yl, 2-benzo[b]thienyl, 3-benzo[b]thienyl, benzofuran-2-yl, or benzofuran-3-yl.

Each $R^3$ is independently selected from $C_{1-6}$ alkyl, $C_{2-6}$ alkenyl, $C_{2-6}$ alkynyl, —OH, —O($C_{1-6}$ alkyl), —O($C_{1-6}$ alkyl)-OH, —O($C_{1-6}$ alkyl)-O($C_{1-6}$ alkyl), —SH, —S($C_{1-6}$ alkyl), —S($C_{1-6}$ alkyl)-SH, —S($C_{1-6}$ alkyl)-S($C_{1-6}$ alkyl), —NH$_2$, —NH($C_{1-6}$ alkyl), —N($C_{1-6}$ alkyl)($C_{1-6}$ alkyl), halogen, —CF$_3$, —CN, —NO$_2$, —N$_3$, —CHO, —CO—($C_{1-6}$ alkyl), —COOH, —CO—O—($C_{1-6}$ alkyl), —O—CO—($C_{1-6}$ alkyl), —CO—NH$_2$, —CO—NH($C_{1-6}$ alkyl), —CO—N($C_{1-6}$ alkyl)($C_{1-6}$ alkyl), —NH—C—($C_{1-6}$ alkyl), —N($C_{1-6}$ alkyl)-CO—($C_{1-6}$ alkyl), —SO$_2$—NH$_2$, —SO$_2$—NH($C_{1-6}$ alkyl), —SO$_2$—N($C_{1-6}$ alkyl)($C_{1-6}$ alkyl), —NH—SO$_2$—($C_{1-6}$ alkyl), —N($C_{1-6}$ alkyl)-SO$_2$—($C_{1-6}$ alkyl), optionally substituted aryl, or optionally substituted heteroaryl, wherein said aryl or said heteroaryl is optionally substituted with one or more (e.g., one, two, three or four) groups independently selected from $C_{1-4}$ alkyl, halogen, —CF$_3$, —CN, —OH, —O($C_{1-4}$ alkyl), —NH$_2$, —NH($C_{1-4}$ alkyl), or —N($C_{1-4}$ alkyl)($C_{1-4}$ alkyl). Preferably, each $R^3$ is independently selected from $C_{1-6}$ alkyl, $C_{2-6}$ alkenyl, $C_{2-6}$ alkynyl, —OH, —O($C_{1-6}$ alkyl), —O($C_{1-6}$ alkyl)-OH, —O($C_{1-6}$ alkyl)-O($C_{1-6}$ alkyl), —SH, —S($C_{1-6}$ alkyl), —S($C_{1-6}$ alkyl)-SH, —S($C_{1-6}$ alkyl)-S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. More preferably, each $R^3$ is independently selected from $C_{1-4}$ alkyl, halogen, —CF$_3$, —CN, —OH, —O($C_{1-4}$ alkyl), —NH$_2$, —NH($C_{1-4}$ alkyl), or —N($C_{1-4}$ alkyl)($C_{1-4}$ alkyl).

n is an integer of 0 to 4. Accordingly, the ring B comprised in the compound of formula (I) has 0 to 4 substituents $R^3$. Preferably n is an integer of 0 to 3, more preferably n is 0, 1 or 2, and even more preferably n is 0. It is to be understood that, if n is 0, then ring B is unsubstituted, i.e., the ring atoms of ring B are substituted with hydrogen in place of $R^3$. It is further to be understood that the upper limit of n (i.e., the upper limit of the number of substituents $R^3$) also depends on the chemical structure of ring B, i.e., the upper limit of n is at most equal to or less than (but not greater than) the number of hydrogen atoms bound to the ring atoms of ring B comprised in formula (I).

As indicated above, R¹ is preferably in ortho-position. Accordingly, it is preferred that the compound of formula (I) has the following structure:

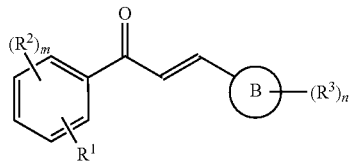

Particularly preferred compounds of formula (I) are the compounds 13 to 15, 18 to 29 and 31 to 33 shown below as well as pharmaceutically acceptable salts, solvates and prodrugs of each one of these compounds:

compound 15
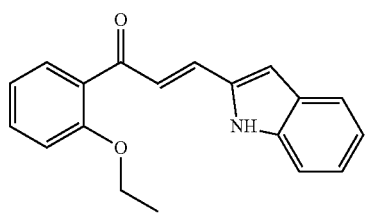

compound 20
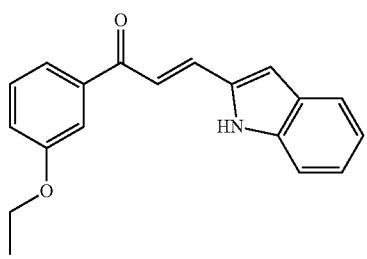

compound 21
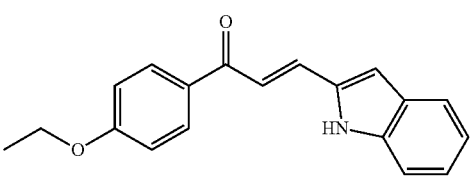

compound 22
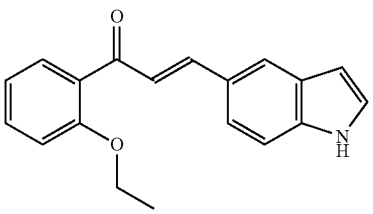

compound 23
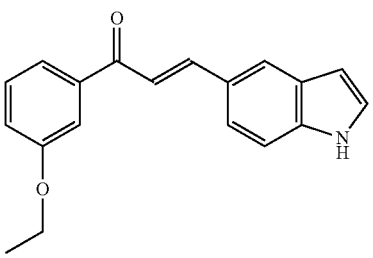

compound 24
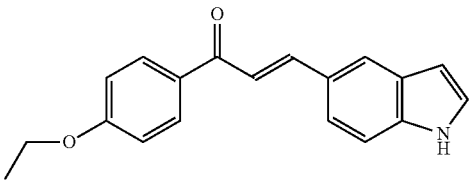

compound 25
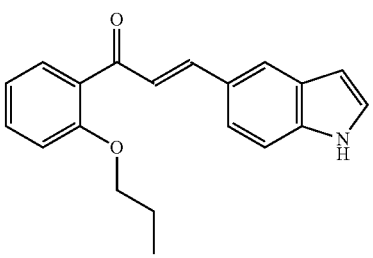

compound 26
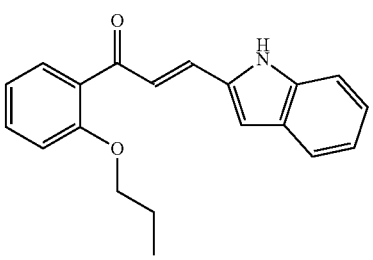

compound 13
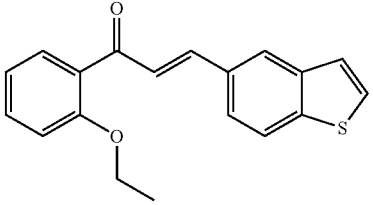

compound 14
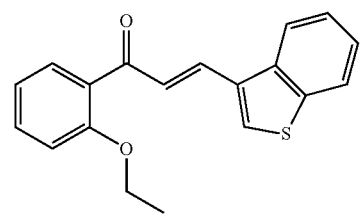

compound 18
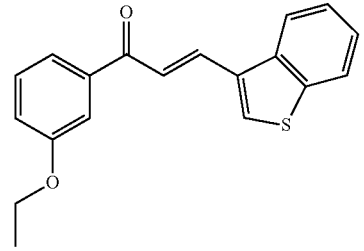

compound 19
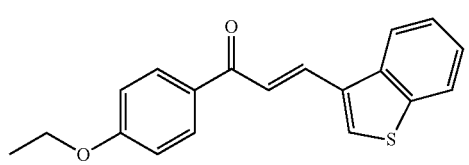

compound 27
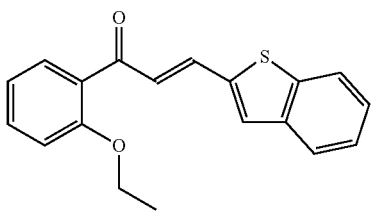

compound 28
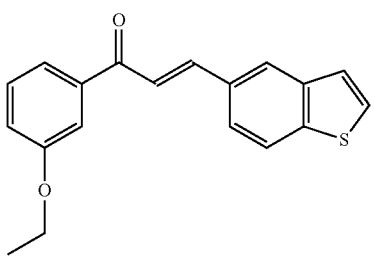

compound 29
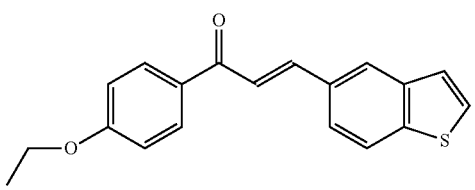

compound 31
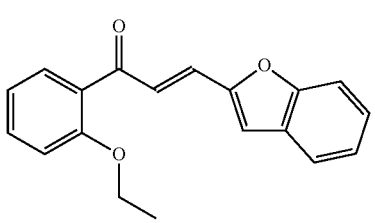

compound 32
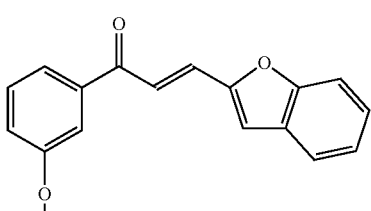

compound 33
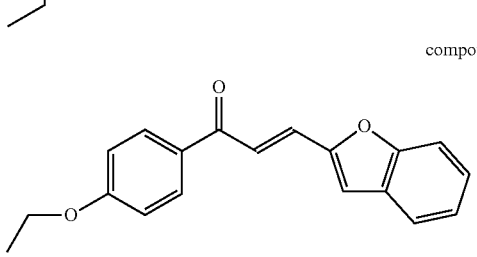

The present invention also relates to a pharmaceutical composition comprising a compound of formula (I) or a pharmaceutically acceptable salt, solvate or prodrug thereof, and a pharmaceutically acceptable excipient. Accordingly, the invention relates to a compound of formula (I) or a pharmaceutically acceptable salt, solvate or prodrug thereof, or a pharmaceutical composition comprising any of the aforementioned entities and a pharmaceutically acceptable excipient, for use as a medicament.

The invention further relates to a compound of formula (I) or a pharmaceutically acceptable salt, solvate or prodrug thereof, or a pharmaceutical composition comprising any of the aforementioned entities and a pharmaceutically acceptable excipient, for use in the treatment or prevention of cancer (particularly hematological cancer).

Moreover, the present invention relates to the use of a compound of formula (I) or a pharmaceutically acceptable salt, solvate or prodrug thereof in the preparation of a medicament for the treatment or prevention of cancer (particularly hematological cancer).

Furthermore, the invention relates to a method of treating or preventing cancer (particularly hematological cancer), the method comprising the administration of a compound of formula (I) or a pharmaceutically acceptable salt, solvate or prodrug thereof, or a pharmaceutical composition comprising any of the aforementioned entities and a pharmaceutically acceptable excipient, to a subject (preferably a human) in need thereof.

The compounds of formula (I) are highly effective against cancer, particularly against hematological cancer. It has been found that the compounds of formula (I) have cytotoxic activity with specificity to neoplastic cells, in particular to hematological cancer cells, as also demonstrated in Example 2 using the malignant hematological B-cell lines MEC1, U-2940, and OCI-Ly7. One of the compounds of formula (I), i.e. compound 15, has further been shown to have particularly advantageous cytotoxic activity in six additional types of human lymphoma and leukemia cells of both the lymphoid and the myeloid lineage (i.e., HL60, K562, CCRF, Jurkat, SU-DHL6, and SU-DHL9 cells) while healthy cells were hardly affected. The compounds of formula (I) are thus suitable for the treatment or prevention of cancer and, in particular, for the treatment or prevention of hematological cancer.

The cancer to be treated or prevented with the compounds or the pharmaceutical compositions according to the present invention is preferably a non-solid cancer and, more preferably, a hematological cancer (or a hematological malignancy), such as a myeloproliferative disorder (MPD), including, e.g., acute myeloid leukemia (AML), chronic myeloid leukemia (CML), or a chronic BCR-ABL negative MPD, or a lymphoid cancer, which may be a B-cell malignancy, such as B-cell lymphoma, non-Hodgkin lymphoma or B-cell derived chronic lymphatic leukemia (B-CLL), or a T-cell malignancy, such as, e.g., T-cell acute lymphoblastic leukemia (T-ALL). However, solid cancers can also be treated or prevented with the compounds or the pharmaceutical compositions of the invention.

The compounds or the pharmaceutical compositions of the present invention are particularly effective and, thus, particularly useful in the medical intervention of hematological cancer, as also demonstrated in Example 2. The hematological cancer to be treated or prevented in accordance with the invention is preferably selected from: Hodgkin's disease; non-Hodgkin's lymphoma, including, e.g., follicular non-Hodgkin's lymphoma, mantle cell lymphoma, or diffuse non-Hodgkin's lymphoma (e.g., diffuse large B-cell lymphoma or Burkitt's tumor); peripheral/cutaneous T-cell lymphoma, including, e.g., mycosis fungoides, Sézary's disease, T-zone lymphoma, lymphoepithelioid lymphoma (e.g., Lennert's lymphoma), or peripheral T-cell lymphoma; lymphosarcoma; a malignant immunoproliferative disease, including, e.g., Waldenström's macroglobulinaemia, alpha heavy chain disease, gamma heavy chain disease (e.g., Franklin's disease), or immunoproliferative small intestinal disease (e.g., Mediterranean disease); multiple myeloma, including, e.g., Kahler's disease, or myelomatosis; plasma cell leukemia; lymphoid leukemia, including, e.g., acute lymphoblastic leukemia, chronic lymphocytic leukemia, subacute lymphocytic leukemia, prolymphocytic leukemia, hairy-cell leukemia (e.g., leukemic reticuloendotheliosis), or adult T-cell leukemia; myeloid leukemia, including, e.g., acute myeloid leukemia, chronic myeloid leukemia, subacute myeloid leukemia, myeloid sarcoma (e.g., chloroma, or granulocytic sarcoma), acute promyelocytic leukemia, or acute myelomonocytic leukemia; chronic BCR-ABL negative myeloproliferative disorders, including, e.g., polycythaemia vera, essential thrombocythemia, or idiopathic myelofibrosis; monocytic leukemia; acute erythraemia or erythroleukemia, including, e.g., acute erythraemic myelosis, or Di Guglielmo's disease; chronic erythraemia, including, e.g., Heilmeyer-Schoner disease; acute megakaryoblastic leukemia; mast cell leukemia; acute panmyelosis; acute myelofibrosis; or Letterer-Siwe disease.

The compounds or the pharmaceutical compositions of the invention are furthermore useful in the treatment or prevention of other types of cancer including, for example, breast (mamma) cancer, genitourinary cancer (such as, e.g., prostate tumor, including a hormone-refractory prostate tumor), lung cancer (such as, e.g., small cell or non-small cell lung tumor), gastrointestinal cancer (such as, e.g., hepatocellular carcinoma, colorectal tumor, colon cancer or gastric cancer), epidermoid cancer (such as, e.g., epidermoid head and/or neck tumor or mouth tumor), melanoma, ovarian cancer, pancreas cancer, neuroblastoma, head and/or neck cancer, bladder cancer, renal cancer, or brain cancer.

As used herein, the term "alkyl" refers to a monovalent saturated aliphatic (i.e., non-aromatic) acyclic hydrocarbon group (i.e., a group consisting of carbon atoms and hydrogen atoms) which may be linear or branched and does not comprise any carbon-to-carbon double bond or any carbon-to-carbon triple bond. A "$C_{1-6}$ alkyl" denotes an alkyl group having 1 to 6 carbon atoms. Preferred exemplary alkyl groups are methyl, ethyl, propyl, or butyl.

The term "alkenyl" refers to a monovalent unsaturated aliphatic acyclic hydrocarbon group which may be linear or branched and comprises at least one carbon-to-carbon double bond while it does not comprise any carbon-to-carbon triple bond. The term "$C_{2-6}$ alkenyl" denotes an alkenyl group having 2 to 6 carbon atoms. Preferred exemplary alkenyl groups are ethenyl, propenyl, or butenyl.

The term "alkynyl" refers to a monovalent unsaturated aliphatic acyclic hydrocarbon group which may be linear or branched and comprises at least one carbon-to-carbon triple bond and optionally one or more carbon-to-carbon double bonds. The term "$C_{2-6}$ alkynyl" denotes an alkynyl group having 2 to 6 carbon atoms. Preferred exemplary alkynyl groups are ethynyl, propynyl, or butynyl.

The term "alkoxy" refers to an —O-alkyl group, wherein the alkyl comprised in said —O-alkyl group is as defined herein above.

The term "aryl" refers to a monovalent aromatic hydrocarbon group, also including bridged ring and/or fused ring systems, containing at least one aromatic ring. "Aryl" may, for example, refer to phenyl, naphthyl, anthracenyl, or phenanthrenyl.

The term "heteroaryl" refers to a monovalent aromatic ring group which may be a monocyclic aromatic ring group containing one or more (e.g., one, two, or three) ring heteroatoms independently selected from O, S or N, or a fused and/or bridged ring system (e.g., a fused bicyclic or tricyclic ring system) wherein at least one ring comprised in said ring system is aromatic and further wherein at least one ring comprised in said ring system contains one or more (e.g., one, two, or three) heteroatoms independently selected from O, S or N. Said aromatic ring group may, e.g., have 5 to 14 ring atoms. Non-limiting examples of heteroaryl groups are pyridinyl, imidazolyl, imidazopyridinyl, pyrimidinyl, pyrazolyl, triazolyl, pyrazinyl, tetrazolyl, furyl, thienyl, oxazolyl, isoxazolyl, oxadiazolyl, thiazolyl, isothiazolyl, pyrrolyl, quinolinyl, isoquinolinyl, indolyl, isoindolyl, benzimidazolyl, benzofuranyl, isobenzofuranyl, cinnolinyl, Indazolyl, indolizinyl, phthalazinyl, pyridazinyl, triazinyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, benzisoxazolyl, quinazolinyl, quinoxalinyl, naphthyridinyl, furopyridinyl, benzo[b]thienyl, naphtho[2,3-b]thienyl, thianthrenyl, chromenyl, xanthenyl, phenoxathiinyl, pyrazolo[1,5-a]pyrimidinyl, carbazolyl, β-carbolinyl, 1,3-benzodioxolyl, phenanthridinyl, acridinyl, perimidinyl, phenanthrolinyl, phenazinyl, phenothiazinyl, or phenoxazinyl.

The term "halogen" refers to —F, —Cl, —Br, or —I.

For a person skilled in the field of synthetic chemistry, various ways for the preparation of the compounds of formula (I) will be readily apparent. For example, the compounds of formula (I) can be prepared in accordance with or in analogy to the synthetic routes described in Example 1.

The scope of the present invention embraces all pharmaceutically acceptable salt forms of the compounds of formula (I) which may be formed, e.g., by protonation of an atom carrying an electron lone pair which is susceptible to protonation, such as an amino group, with an inorganic or organic acid, or as a salt of a carboxylic acid group with a physiologically acceptable cation as they are well-known in the art. Exemplary base addition salts comprise, for example, alkali metal salts such as sodium or potassium salts; alkaline earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

Moreover, the scope of the invention also embraces solid forms of the compounds of formula (I) in any solvated form including, e.g., solvates with water, for example hydrates, or with organic solvents such as, e.g., methanol, ethanol or acetonitrile, i.e., as a methanolate, ethanolate or acetonitrilate, respectively; or in the form of any polymorph.

Furthermore, the formulas in the present application are intended to cover all possible stereoisomers, including enantiomers and diastereomers, of the indicated compounds. Thus, all stereoisomers of the compounds of formula (I) are contemplated as part of the present invention, either in admixture or in pure or substantially pure form. The scope of the compounds according to the invention embraces all the possible stereoisomers and their mixtures. It very particularly embraces the racemic forms and the isolated optical isomers. The racemic forms can be resolved by physical methods, such as, e.g., fractional crystallization, separation or crystallization of diastereomeric derivatives or separation by chiral column chromatography. The individual optical isomers can be obtained from the racemates using conventional methods, such as, e.g., salt formation with an optically active acid followed by crystallization.

Pharmaceutically acceptable prodrugs of compounds of formula (I) are derivatives which have chemically or metabolically cleavable groups and become, by solvolysis or under physiological conditions, the corresponding compounds of formula (I) which are pharmaceutically active in vivo. Prodrugs of compounds of formula (I) may be formed in a conventional manner with a functional group of the compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound of the present invention has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester, N,N-diethylglycolamidoester or α-acetoxyethylester. When a compound of the present invention has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—$CH_3$, —OC(=O)—$C_2H_5$, —OC(=O)-(tert-Bu), —OC(=O)—$C_{15}H_{31}$, —OC(=O)-(m-COONa-Ph), —OC(=O)—$CH_2CH_2$COONa, —O(C=O)—CH($NH_2$)$CH_3$ or —OC(=O)—$CH_2$—N($CH_3$)$_2$. When a compound of the present invention has an amino group, an amide derivative prepared by reacting the amino group with a suitable acid halide or a suitable mixed anhydride is exemplified as a prodrug. An especially preferred amide derivative as a prodrug is —NHC(=O)—($CH_2$)$_2$O$CH_3$ or —NHC(=O)—CH($NH_2$)$CH_3$.

The compounds described herein may be administered as compounds per se or may be formulated as medicaments. Within the scope of the present invention are medicaments or pharmaceutical compositions comprising as an active ingredient a compound of formula (I) as described and defined above. The pharmaceutical compositions may optionally comprise one or more pharmaceutically acceptable excipients, such as carriers, diluents, fillers, disintegrants, lubricating agents, binders, colorants, pigments, stabilizers, preservatives, or antioxidants.

The pharmaceutical compositions can be formulated by techniques known to the person skilled in the art, such as the techniques published in Remington's Pharmaceutical Sciences, 20$^{th}$ Edition. The pharmaceutical compositions can be formulated as dosage forms for oral, parenteral, such as intramuscular, intravenous, subcutaneous, intradermal, intraarterial, intracardial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds of formula (I) or the above described pharmaceutical compositions comprising one or more compounds of formula (I) may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e.g., using injection techniques or infusion techniques, and including, for example, by injection, e.g. subcutaneous, intradermal, intramuscular, intravenous, intraarterial, intracardiac (i.e., intracardial), intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal.

If said compounds or pharmaceutical compositions are administered parenterally, then examples of such administration include one or more of: intravenously, intraarterially, intraperitoneally, intrathecally, intraventricularly, intraurethrally, intrasternally, intracranially, intracardially, intramuscularly or subcutaneously administering the compounds pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Alternatively, said compounds or pharmaceutical compositions can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds of formula (I) for administration to a human (of approximately 70 kg body weight) may be 0.001 mg to 2000 mg, preferably 0.05 mg to 1000 mg, of the active ingredient per unit dose. The unit dose may be administered, for example, 1 to 4 times per day. The dose will depend on the route of administration. It will be appreciated that it may be necessary to make routine variations to the dosage depending on the age and weight of the patient/subject as well as the severity of the condition to be treated. The precise dose and route of administration will ultimately be at the discretion of the attendant physician or veterinarian.

The compounds of formula (I) can be used in combination with other therapeutic agents. When a compound of the invention is used in combination with a second therapeutic agent active against the same disease, the dose of each compound may differ from that when the compound is used alone. The combination of a compound of the present invention with a second therapeutic agent may comprise the administration of the second therapeutic agent with the compound of the invention. Such an administration may comprise simultaneous/concomitant administration. However, also sequential/separate administration is envisaged, as also explained below.

Preferably, the second therapeutic agent to be administered in combination with the compounds of this invention is an anticancer drug. The anticancer drug to be administered in combination with a compound of formula (I) according to the present invention may be: a tumor angiogenesis inhibitor (for example, a protease inhibitor, an epidermal growth factor receptor kinase inhibitor, or a vascular endothelial growth factor receptor kinase inhibitor); a cytotoxic drug (for example, an antimetabolite, such as purine and pyrimidine analogue antimetabolites); an antimitotic agent (for example, a microtubule stabilizing drug or an antimitotic alkaloid); a platinum coordination complex; an anti-tumor antibiotic; an alkylating agent (for example, a nitrogen mustard or a nitrosourea); an endocrine agent (for example, an adrenocorticosteroid, an androgen, an anti-androgen, an estrogen, an anti-estrogen, an aromatase inhibitor, a gonadotropin-releasing hormone agonist, or a somatostatin analogue); or a compound that targets an enzyme or receptor that is overexpressed and/or otherwise involved in a specific metabolic pathway that is misregulated in the tumor cell (for example, ATP and GTP phosphodiesterase inhibitors, histone deacetylase inhibitors, protein kinase inhibitors (such as serine, threonine and tyrosine kinase inhibitors (for example, Abelson protein tyrosine kinase)) and the various growth factors, their receptors and corresponding kinase inhibitors (such as epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors)); methionine, aminopeptidase inhibitors, proteasome inhibitors, cyclooxygenase inhibitors (for example, cyclooxygenase-1 or cyclooxygenase-2 inhibitors) and topoisomerase inhibitors (for example, topoisomerase I inhibitors or topoisomerase II inhibitors).

An alkylating agent which can be used as an anticancer drug in combination with a compound of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazines (such as temozolomide).

A platinum coordination complex which can be used as an anticancer drug in combination with a compound of the present invention may be, for example, cisplatin, carboplatin, nedaplatin, oxaliplatin, satraplatin, or triplatin tetranitrate.

A cytotoxic drug which can be used as an anticancer drug in combination with a compound of the present invention may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent which can be used as an anticancer drug in combination with a compound of the present invention may be, for example, a taxane (such as docetaxel, larotaxel, ortataxel, paclitaxel/taxol, or tesetaxel), a Vinca alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/azaepothilone B).

An anti-tumor antibiotic which can be used as an anticancer drug in combination with a compound of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from *Streptomyces* (such as actinomycin (including actinomycin D), bleomycin, mitomycin (including mitomycin C), or plicamycin).

A tyrosine kinase inhibitor which can be used as an anticancer drug in combination with a compound of the present invention may be, for example, axitinib, bosutinib, cediranib, dasatinib, erlotinib, gefitinib, imatinib, lapatinib, lestaurtinib, nilotinib, semaxanib, sorafenib, sunitinib, or vandetanib.

A topoisomerase-inhibitor which can be used as an anticancer drug in combination with a compound of the present invention may be, for example, a topoisomerase I inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin).

Further anticancer drugs may be used in combination with a compound of the present invention. The anticancer drugs may comprise biological or chemical molecules, like TNF-related apoptosis-inducing ligand (TRAIL), tamoxifen, amsacrine, bexarotene, estramustine, irofulven, trabectedin, cetuximab, panitumumab, tositumomab, alemtuzumab, bevacizumab, edrecolomab, gemtuzumab, alvocidib, seliciclib, aminolevulinic acid, methyl aminolevulinate, efaproxiral, porfimer sodium, talaporfin, temoporfin, verteporfin, alitretinoin, tretinoin, anagrelide, arsenic trioxide, atrasentan, bortezomib, carmofur, celecoxib, demecolcine, elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, vorinostat, ABT199, idelalisib (CAL101), and ibrutinib (PCI32765).

Also biological drugs, like antibodies, antibody fragments, antibody constructs (for example, single-chain constructs), and/or modified antibodies (like CDR-grafted antibodies, humanized antibodies, "full humanized" antibodies, etc.) directed against cancer or tumor markers/factors/cytokines involved in proliferative diseases can be employed in co-therapy approaches with the compounds of the invention. Examples of such biological molecules are anti-HER2 antibodies (e.g. trastuzumab, Herceptin®), anti-CD20 antibodies (e.g. Rituximab, Rituxan®, MabThera®, Reditux®), anti-CD19/CD3 constructs (see, e.g., EP-B1 1071752) and anti-TNF antibodies (see, e.g., Taylor P C. Antibody therapy for rheumatoid arthritis. Curr Opin Pharmacol. 2003. 3(3): 323-328). Further antibodies, antibody fragments, antibody constructs and/or modified antibodies to be used in co-therapy approaches with the compounds of the invention can be found in Taylor P C. Curr Opin Pharmacol. 2003. 3(3):323-328; Roxana A. Maedica. 2006. 1(1):63-65.

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the compound of the present invention (i.e., the compound of formula (I)) or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately, they may be provided in any convenient formulation.

The compounds of formula (I) can also be administered in combination with physical therapy, such as radiotherapy. Radiotherapy may commence before, after, or simultaneously with administration of the compounds of the invention. For example, radiotherapy may commence 1-10 minutes, 1-10 hours or 24-72 hours after administration of the compounds. Yet, these time frames are not to be construed as limiting. The subject is exposed to radiation, preferably gamma radiation, whereby the radiation may be provided in a single dose or in multiple doses that are administered over several hours, days and/or weeks. Gamma radiation may be delivered according to standard radiotherapeutic protocols using standard dosages and regimens.

The present invention thus relates to a compound of formula (I) or a pharmaceutically acceptable salt, solvate, or prodrug thereof, or a pharmaceutical composition comprising any of the aforementioned entities in combination with a pharmaceutically acceptable excipient, for use in the treatment or prevention of cancer, in particular the treatment or prevention of hematological cancer, wherein the compound or the pharmaceutical composition is to be administered in combination with an anticancer drug and/or in combination with radiotherapy.

As also described in Example 3, the combination of a compound of formula (I) with any one of the anticancer drugs ABT199, idelalisib (CAL101) and ibrutinib (PCI32765) has been found to provide a synergistically enhanced cytotoxic effect on primary cells from CLL patients. In a preferred embodiment, the invention thus relates to a compound of formula (I) or a pharmaceutically acceptable salt, solvate, or prodrug thereof, or a pharmaceutical composition comprising any of the aforementioned entities in combination with a pharmaceutically acceptable excipient, for use in the treatment or prevention of cancer, particularly in the treatment or prevention of hematological cancer (such as, e.g., chronic lymphoid leukemia (CLL), or other B-cell malignancies), wherein the compound or the pharmaceutical composition is to be administered in combination with ABT199, idelalisib and/or ibrutinib.

The term "treatment of a disorder or disease" as used herein, such as "treatment of cancer", is well known in the art. "Treatment of a disorder or disease" implies that a disorder or disease is suspected or has been diagnosed in a patient/subject. A patient/subject suspected of suffering from a disorder or disease typically shows specific clinical and/or pathological symptoms which a skilled person can attribute to a specific pathological condition (i.e., diagnose a disorder or disease).

The "treatment" of a disorder or disease may, for example, lead to a halt in the progression of the disorder or disease (e.g., no deterioration of symptoms) or a delay in the progression of the disorder or disease (in case the halt in progression is of a transient nature only). The "treatment" of a disorder or disease may also lead to a partial response (e.g., amelioration of symptoms) or complete response (e.g., disappearance of symptoms) of the subject/patient suffering from the disorder or disease. Accordingly, the "treatment" of a disorder or disease may also refer to an amelioration of the disorder or disease, which may, e.g., lead to a halt in the progression of the disorder or disease or a delay in the progression of the disorder or disease. Such a partial or complete response may be followed by a relapse. It is to be understood that a subject/patient may experience a broad range of responses to a treatment (e.g., the exemplary responses as described herein above). The treatment of a disorder or disease may, inter alia, comprise curative treatment (preferably leading to a complete response and eventually to healing of the disorder or disease) and palliative treatment (including symptomatic relief).

The term "prevention of a disorder or disease" as used herein, such as "prevention of cancer", is also well known in the art. For example, a patient/subject suspected of being prone to suffer from a disorder or disease as defined herein may, in particular, benefit from a prevention of the disorder or disease. The subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician.

The subject or patient to be treated in accordance with the invention may be an animal (e.g., a non-human animal), a vertebrate animal, a mammal, a rodent (e.g., a guinea pig, a hamster, a rat, a mouse), a murine (e.g., a mouse), a canine (e.g., a dog), a feline (e.g., a cat), a porcine (e.g., a pig), an equine (e.g., a horse), a primate, a simian (e.g., a monkey or ape), a monkey (e.g., a marmoset, a baboon), an ape (e.g., a gorilla, chimpanzee, orang-utan, gibbon), or a human. In the context of this invention, it is particularly envisaged that animals are to be treated which are economically, agronomically or scientifically important. Scientifically important organisms include, but are not limited to, mice, rats, and rabbits. Lower organisms such as, e.g., fruit flies like *Drosophila melanogaster* and nematodes like *Caenorhabditis elegans* may also be used in scientific approaches. Non-limiting examples of agronomically important animals are sheep, cattle and pigs, while, for example, cats and dogs may be considered as economically important animals. Preferably, the subject/patient is a mammal; more preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orang-utan, a gibbon, a sheep, cattle, or a pig); most preferably, the subject/patient is a human.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "A is optionally substituted with B" (or "A may be substituted with B") means that A is either substituted with B, or A is not substituted with B. Likewise, if a component of a composition is indicated to be "optional", the invention specifically relates to both possibilities, i.e., that the corresponding component is present (contained in the composition) or that the corresponding component is absent from the composition.

It is to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in formula (I).

In this specification, a number of documents including patent applications, scientific literature and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention is also illustrated by the following illustrative figures. The appended figures show:

FIG. 1: Structure-activity relationship (SAR) studies based on the lead compound 1 were obtained by structural modifications of rings A and B and resulted in compound 15 as new hit compound. The cytotoxic impact of the compounds 1 and 15 on three malignant hematological cell lines (MEC1, U-2940 and OCI-Ly7) as well as the mouse fibroblast cell line (M2-10B4) used in the lead structure optimization process are shown.

Figure 2:
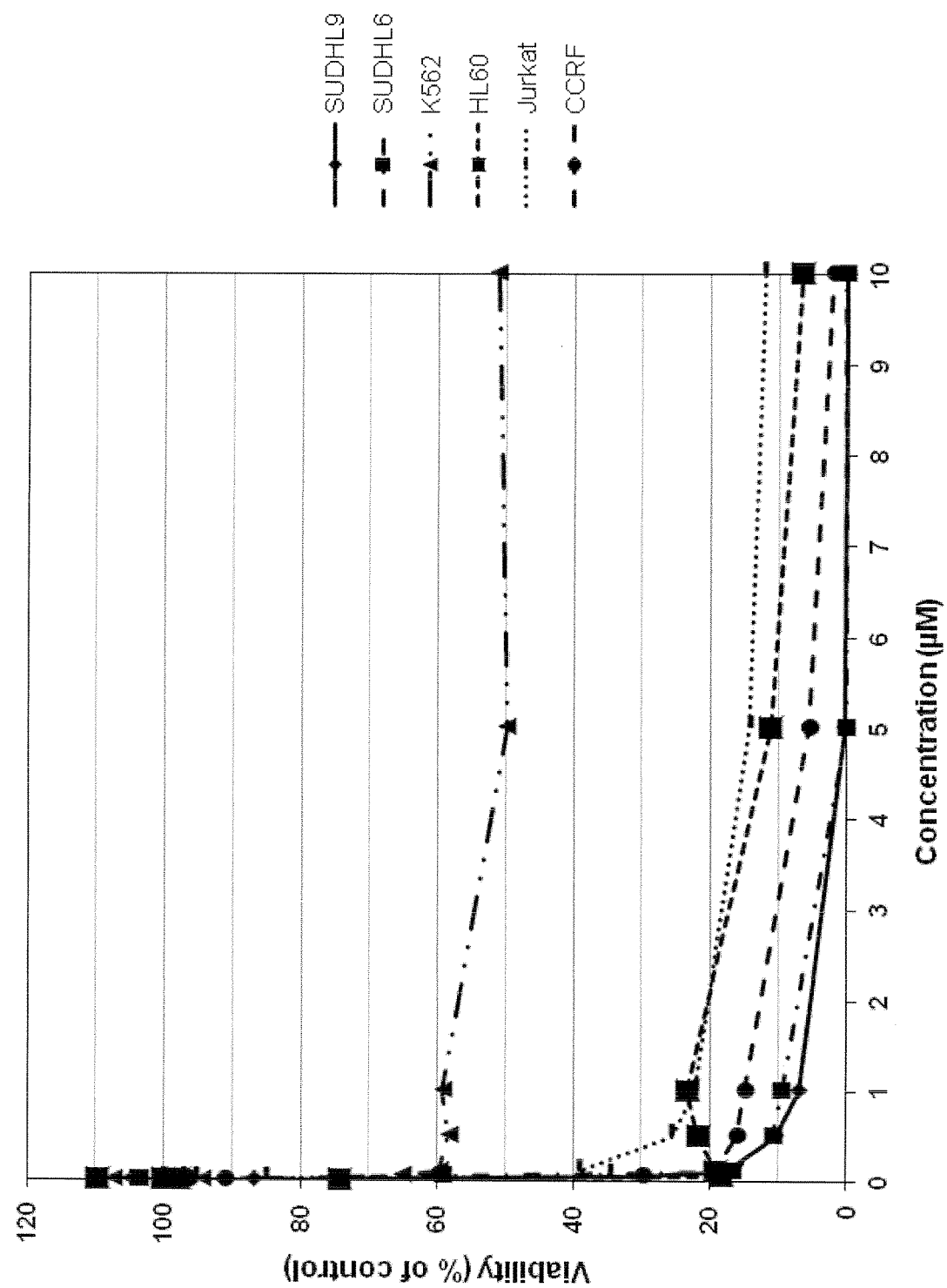

FIG. 2: Cytotoxic effect of compound 15 on a variety of hematologic cell lines. CCRF, Jurkat: T-cell acute lymphoblastic leukemia; HL60, K562: myeloid leukemia; SU-DHL6, SU-DHL9: B-cell lymphoma. Viability was determined as described in the methods section in Example 2 and normalized to cells incubated with vehicle only.

Figure 3:
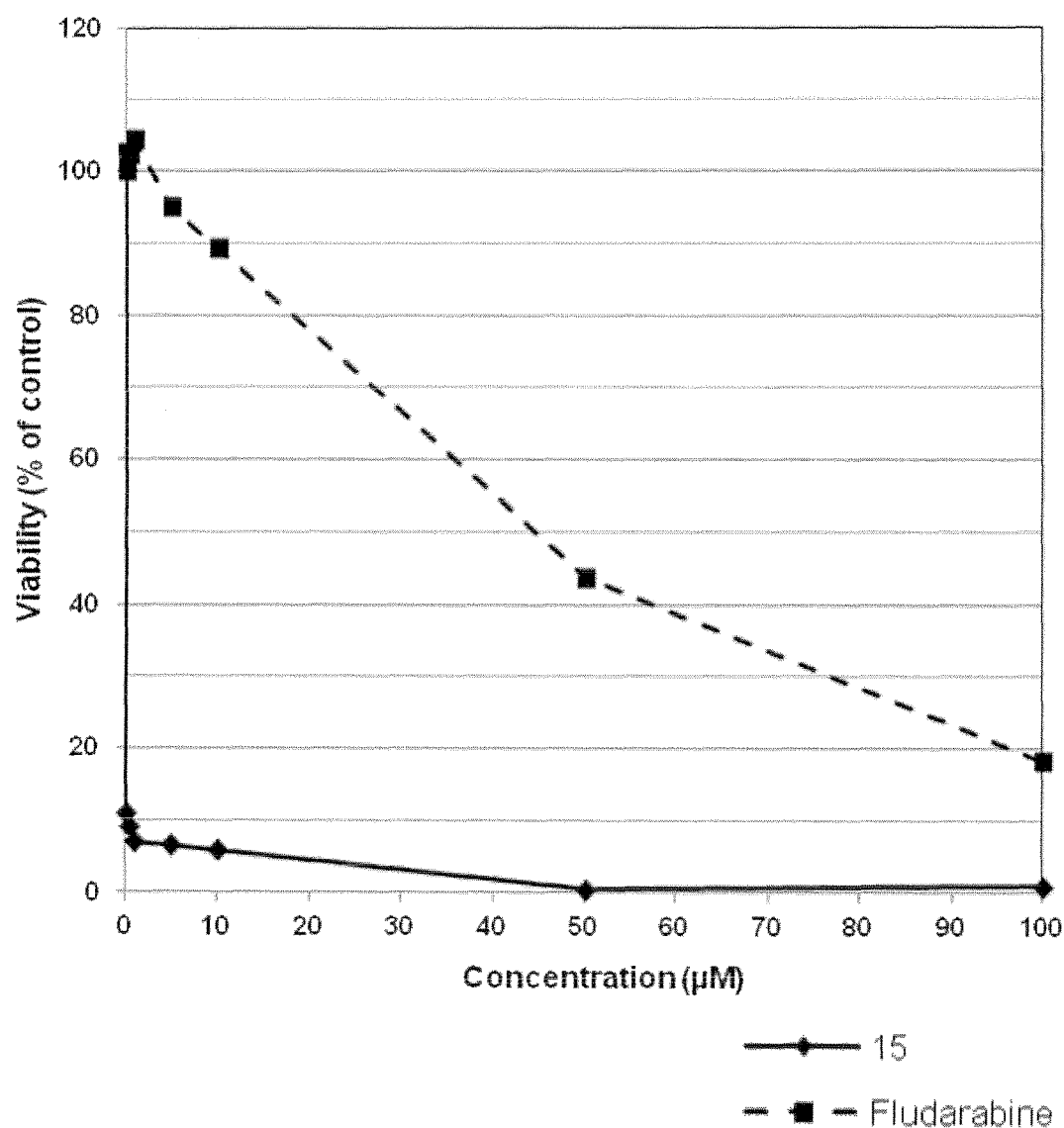
Figure 3:
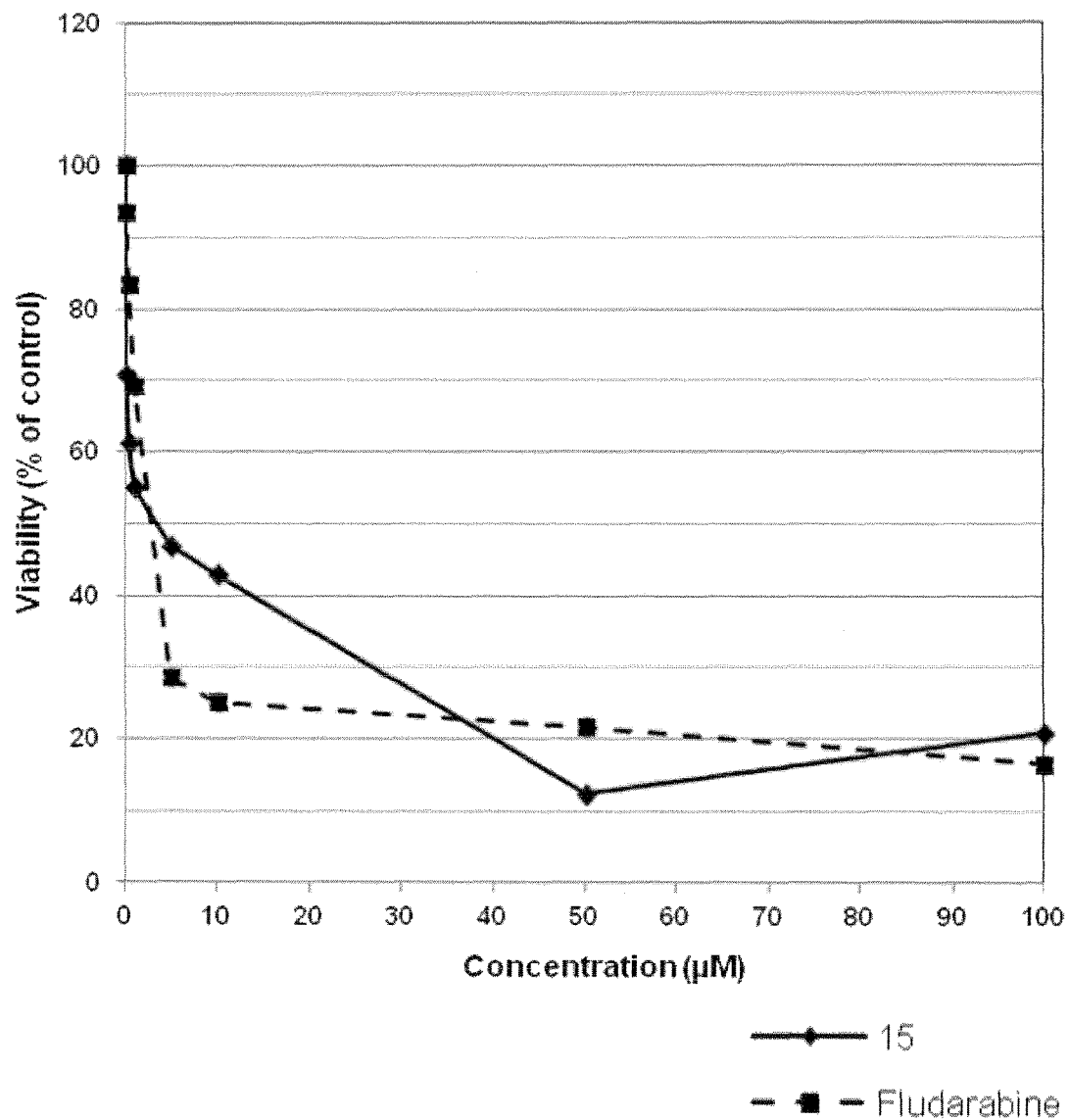
Figure 3:
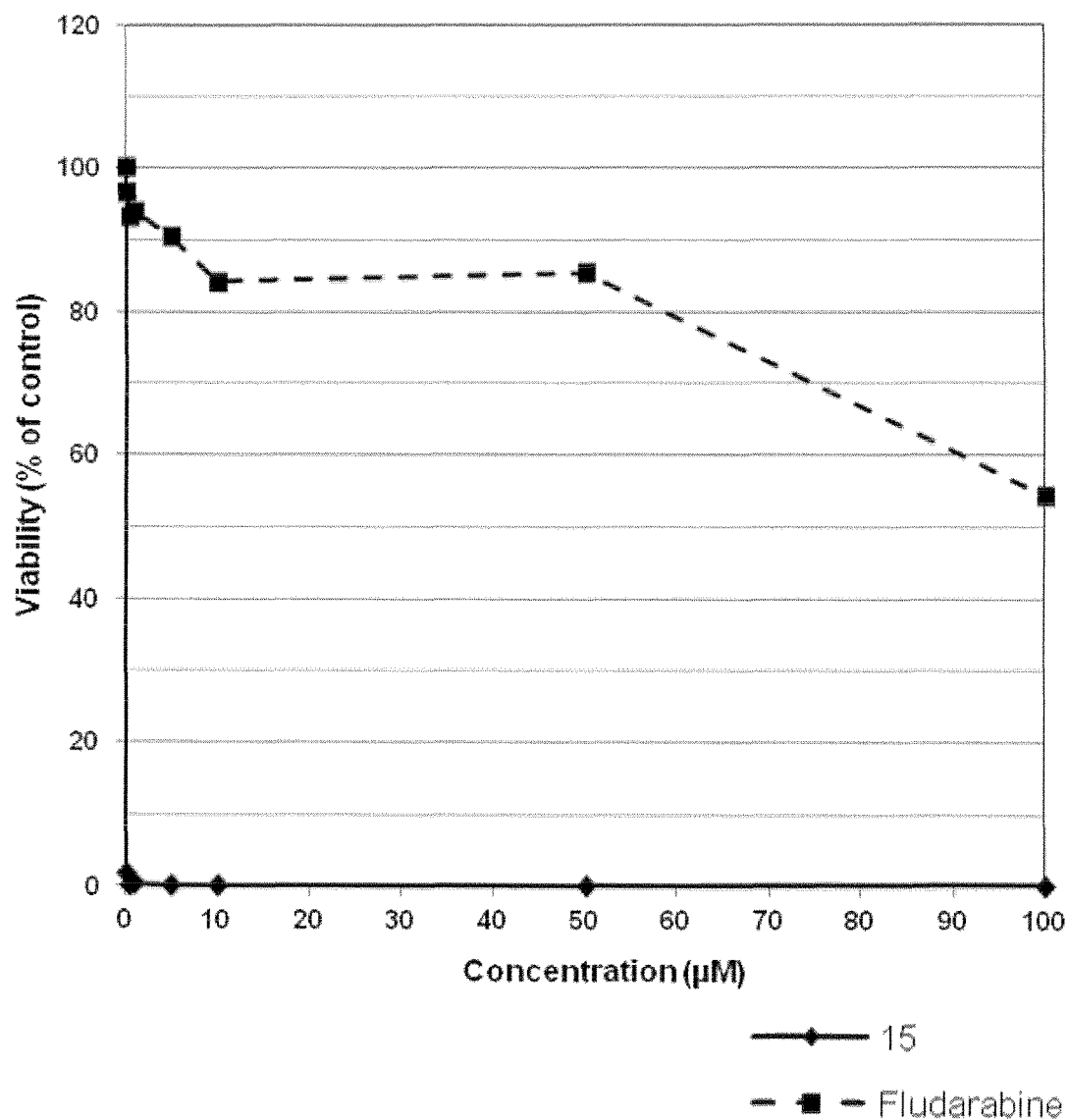

FIG. 3: Comparison of cytotoxic efficacies of compound 15 and fludarabine in 3 cell lines of the B-cell lineage. (A) MEC1; (B) U-2940; (C) OCI-Ly7. Results were normalized to incubations with vehicle only. $IC_{50}$ values (µM) were 0.022 and 42.34 (MEC1), 0.052 and 1.95 (U-2940), 2.9 and 105.5 (OCI-Ly7) for compound 15 and fludarabine, respectively.

Figure 4:
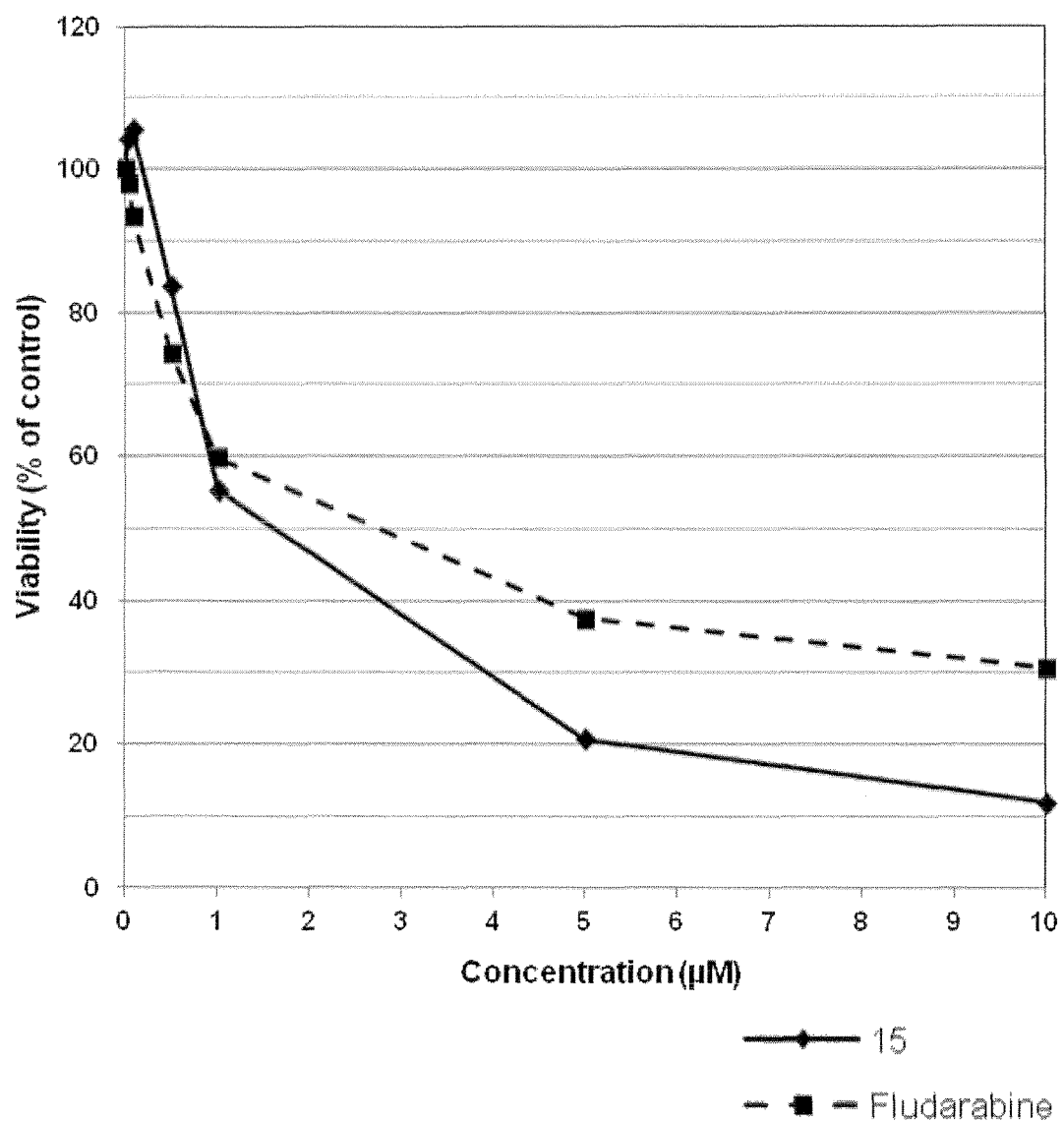
Figure 4:
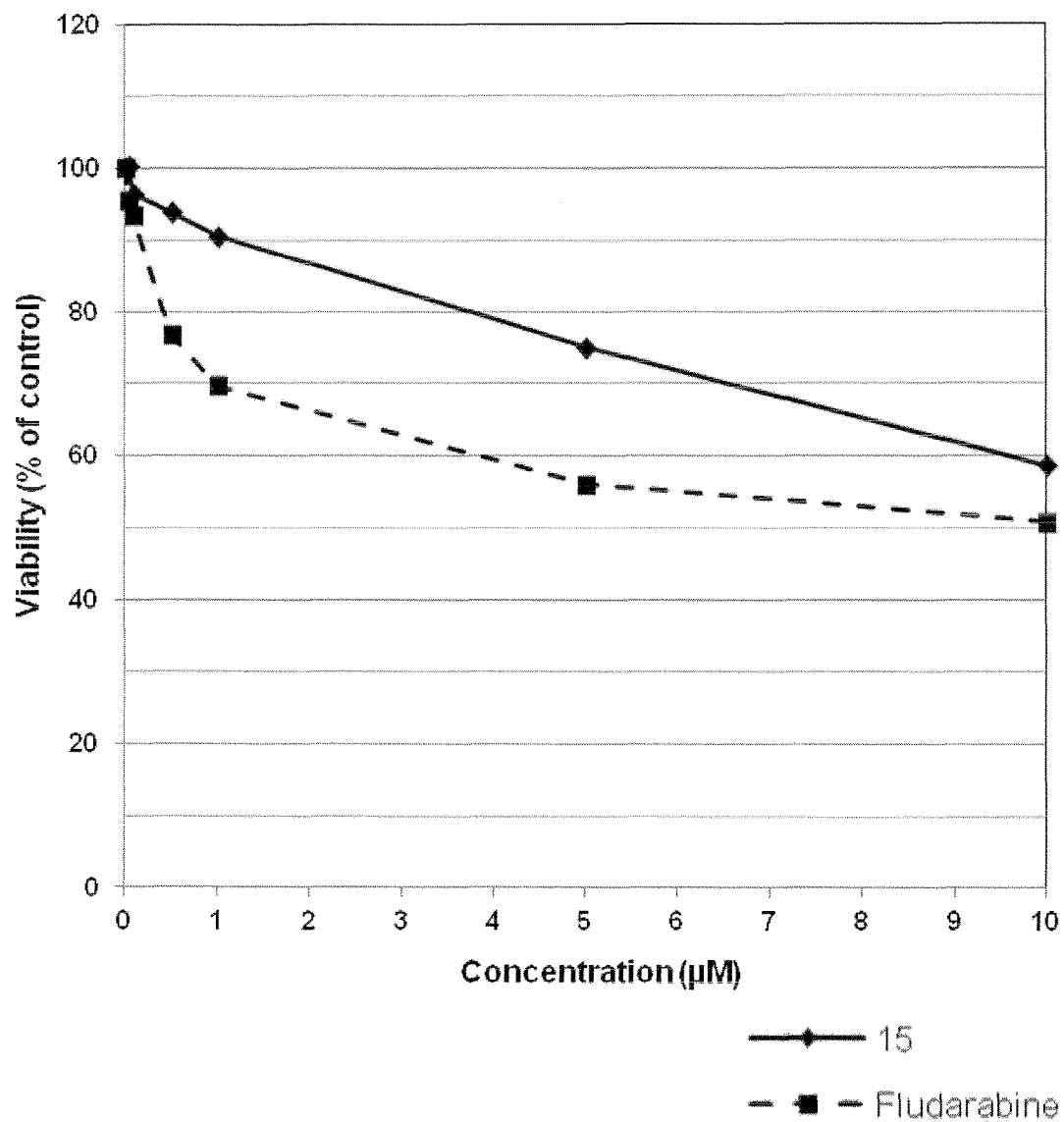
Figure 4:
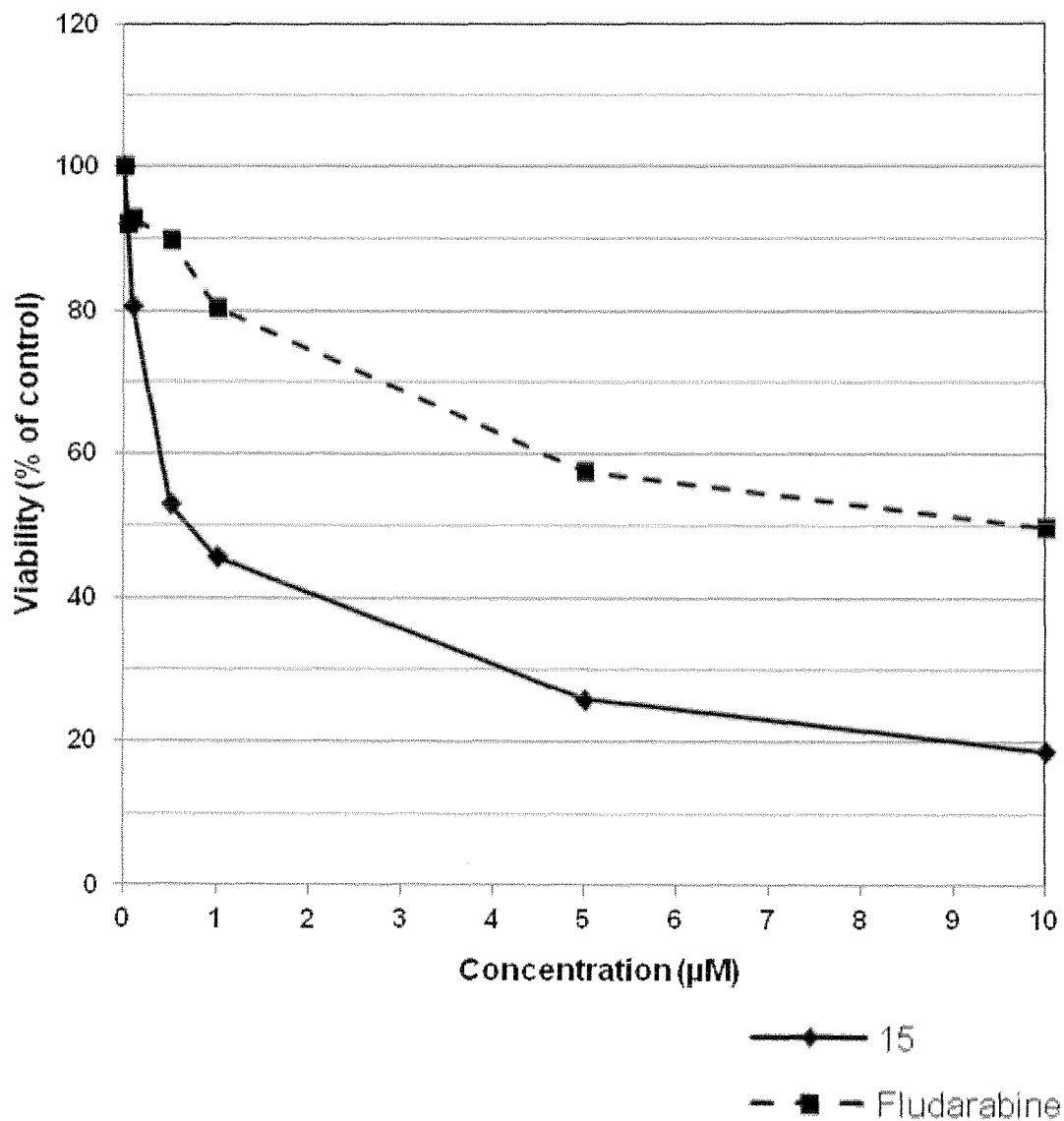

FIG. 4: Comparison of cytotoxic efficacies of compound 15 and fludarabine in primary cells. (A) Peripheral blood mononuclear cells (PBMC) of chronic lymphocytic leukemia (CLL) patients (N=15) tested in suspension culture; (B) PBMC of healthy individuals (N=4) in suspension culture;

(C) PBMC of CLL patients (N=9) cultured over a layer of mouse fibroblast cells (M2-10B4). Results were normalized to incubations with vehicle only. $IC_{50}$ values are listed in Table 4 (see Example 2).

Figure 5:
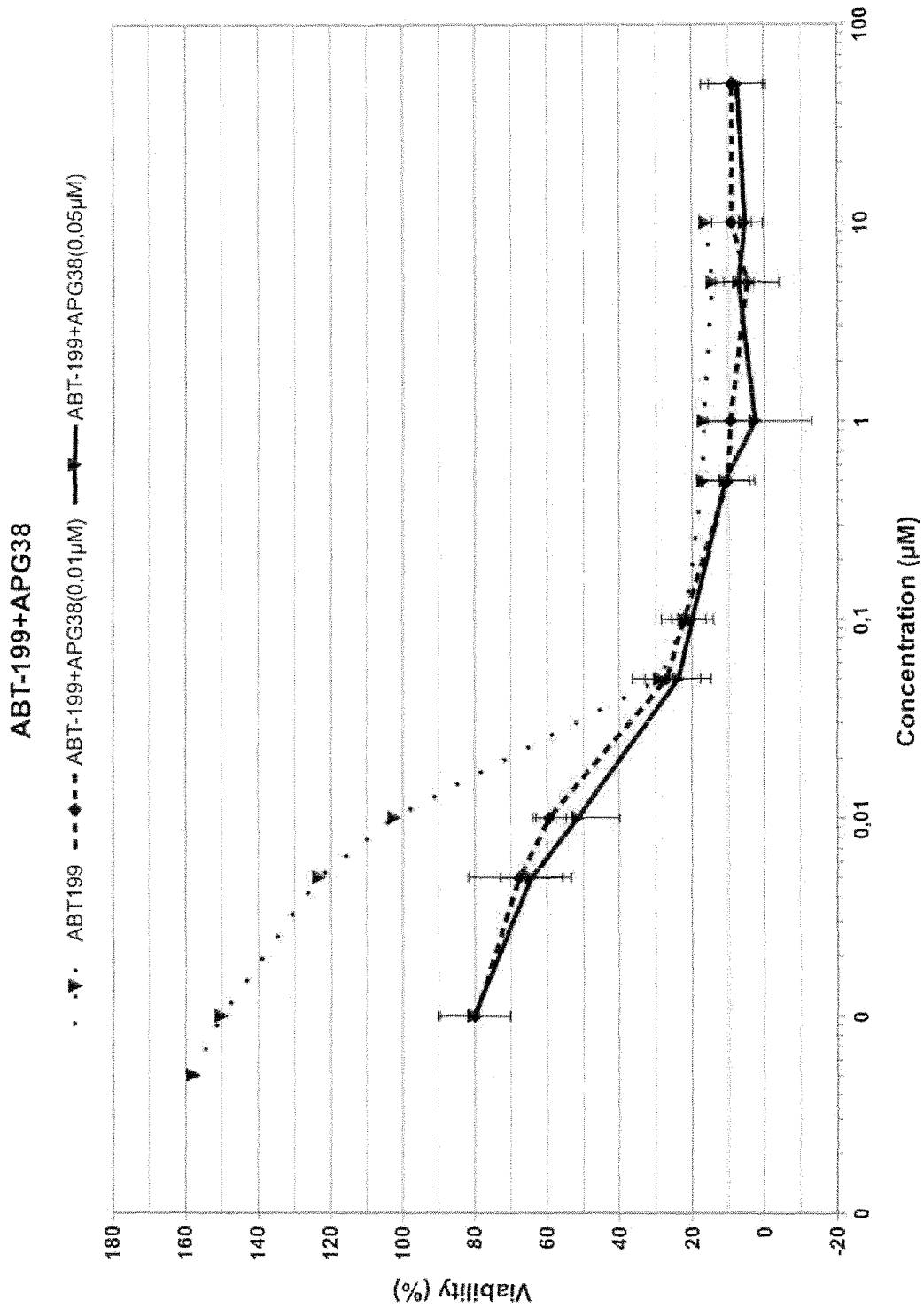
Figure 5:
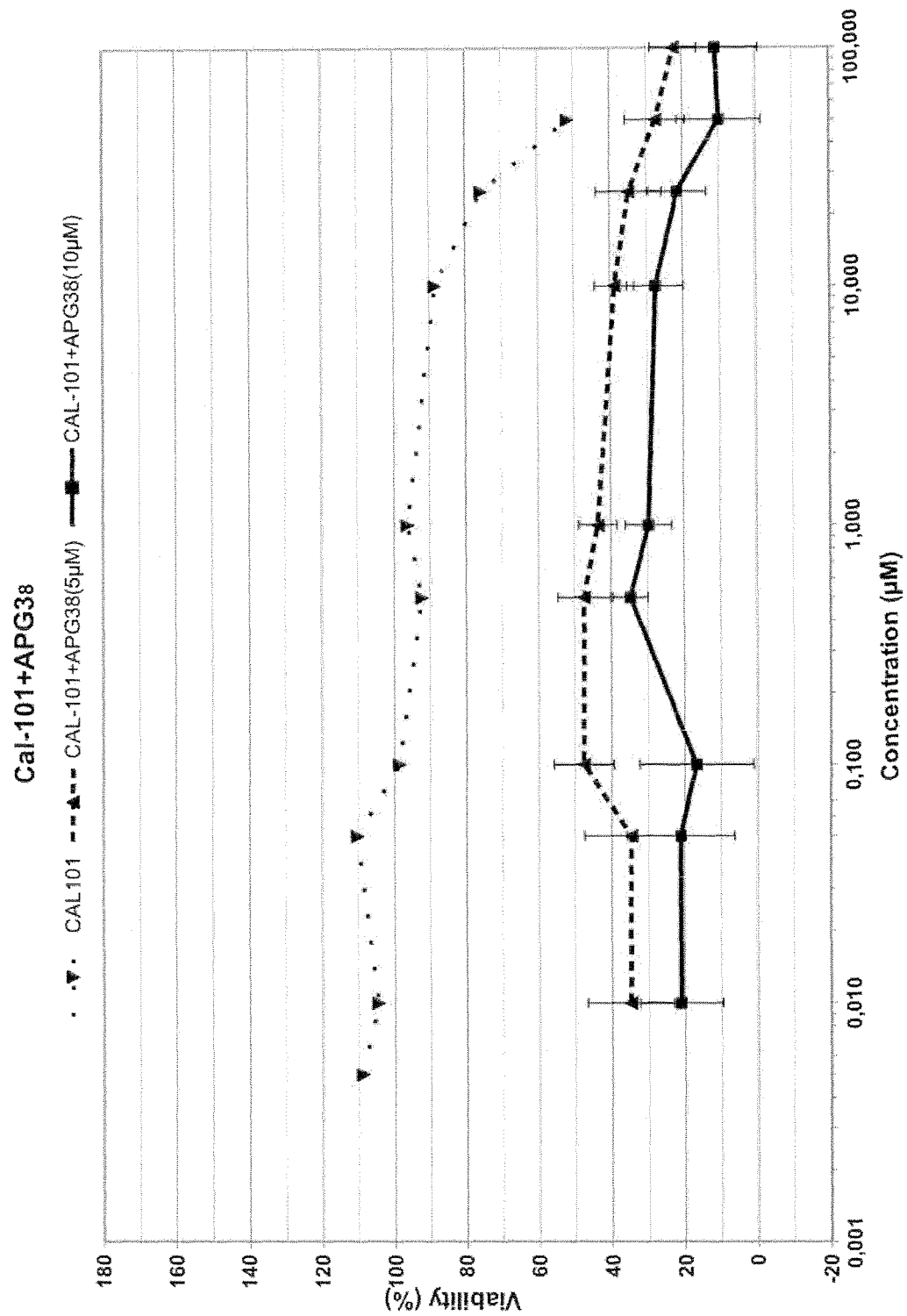
Figure 5:
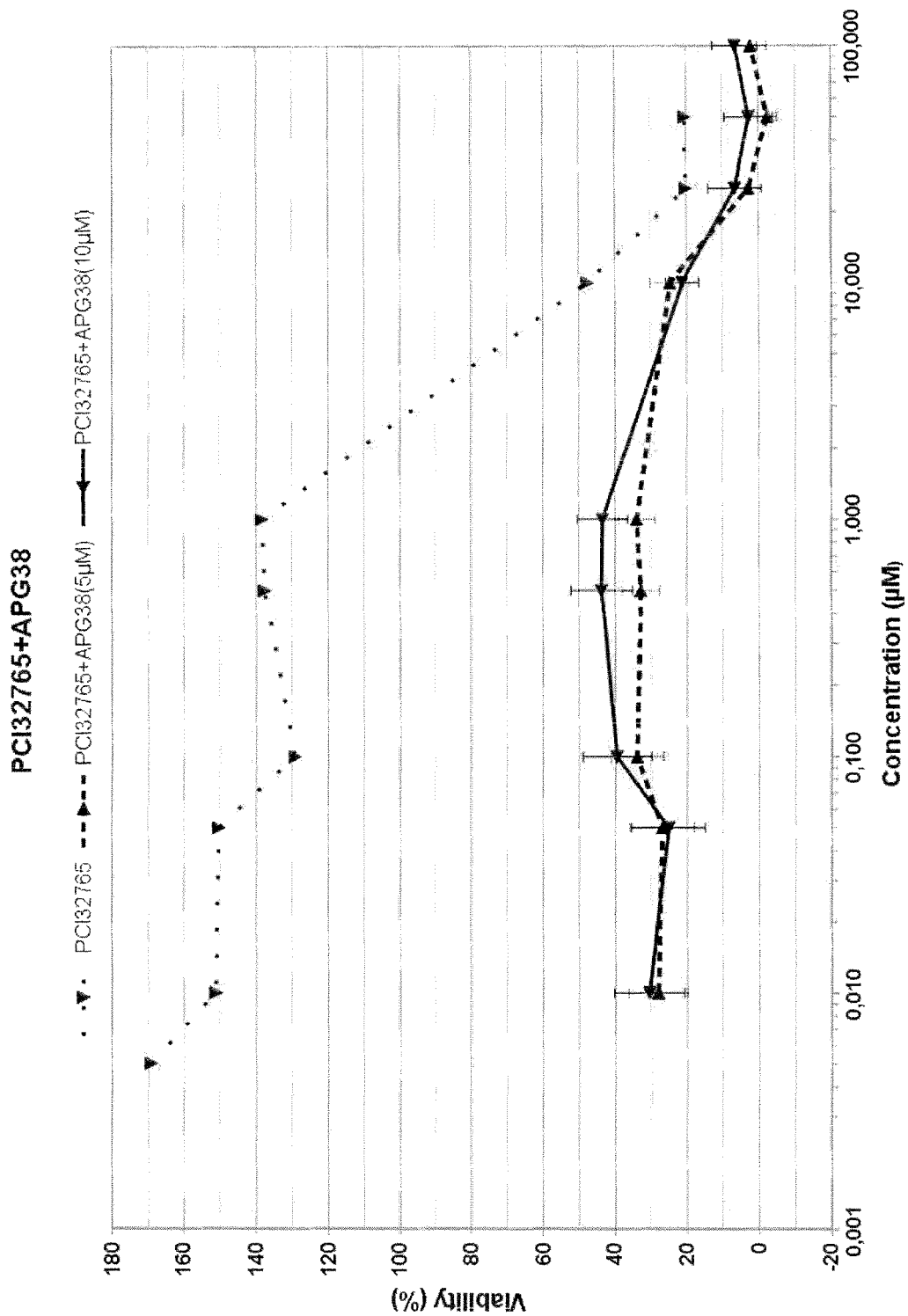

FIG. 5: Combination treatment of CLL primary cells with compound 15 (referred to as "APG38" in this Figure) together with a further anticancer agent (ABT199, CAL101 or PCI32765); see Example 3. (A) Impact of ABT199 alone and in combination with compound 15 on the viability of primary cells from CLL patients (N=5). Cells were incubated in triplicates for 48 h before viability was determined. Mean values and standard deviations are shown. (B) Impact of CAL101 alone and in combination with compound 15 on the viability of primary cells from CLL patients (N=6). Cells were incubated in triplicates for 48 h before viability was determined. Mean values and standard deviations are shown. Since the x-axis has a logarithmic scale, the vehicle only incubation (=origin–"0") with the 100% viability reference point is not depicted. (C) impact of CAL101 alone and in combination with compound 15 on the viability of primary cells from CLL patients (N=6). Cells were incubated in triplicates for 48 h before viability was determined. Mean values and standard deviations are shown. Since the x-axis has a logarithmic scale, the vehicle only incubation (=origin–"0") with the 100% viability reference point is not depicted.

The present invention particularly relates to the following items:

1. A compound of formula (I)

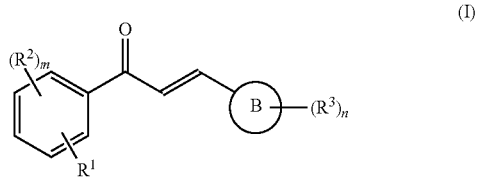

(I)

wherein:
R$^1$ is C$_{2-6}$ alkoxy;
each R$^2$ is independently selected from C$_{1-6}$ alkyl, C$_{2-6}$ alkenyl, C$_{2-6}$ alkynyl, —OH, —O(C$_{1-6}$ alkyl), —O(C$_{1-6}$ alkyl)-OH, —O(C$_{1-6}$ alkyl)-O(C$_{1-6}$ alkyl), —SH, —S(C$_{1-6}$ alkyl), —S(C$_{1-6}$ alkyl)-SH, —S(C$_{1-6}$ alkyl)-S(C$_{1-6}$ alkyl), —NH$_2$, —NH(C$_{1-6}$ alkyl), —N(C$_{1-6}$ alkyl)(C$_{1-6}$ alkyl), halogen, —CF$_3$, —CN, —NO$_2$, —N$_3$, —CHO, —CO—(C$_{1-6}$ alkyl), —COOH, —CO—O—(C$_{1-6}$ alkyl), —O—CO—(C$_{1-6}$ alkyl), —CO—NH$_2$, —CO—NH(C$_{1-6}$ alkyl), —CO—N(C$_{1-6}$ alkyl)(C$_{1-6}$ alkyl), —NH—CO—(C$_{1-6}$ alkyl), —N(C$_{1-6}$ alkyl)-CO—(C$_{1-6}$ alkyl), —SO$_2$—NH$_2$, —SO$_2$—NH(C$_{1-6}$ alkyl), —SO$_2$—N(C$_{1-6}$ alkyl)(C$_{1-6}$ alkyl), —NH—SO$_2$—(C$_{1-6}$ alkyl), or —N(C$_{1-6}$ alkyl)-SO$_2$—(C$_{1-6}$ alkyl);
each R$^3$ is independently selected from C$_{1-6}$ alkyl, C$_{2-6}$ alkenyl, C$_{2-6}$ alkynyl, —OH, —O(C$_{1-6}$ alkyl), —O(C$_{1-6}$ alkyl)-OH, —O(C$_{1-6}$ alkyl)-O(C$_{1-6}$ alkyl), —SH, —S(C$_{1-6}$ alkyl), —S(C$_{1-6}$ alkyl)-SH, —S(C$_{1-6}$ alkyl)-S(C$_{1-6}$ alkyl), —NH$_2$, —NH(C$_{1-6}$ alkyl), —N(C$_{1-6}$ alkyl)(C$_{1-6}$ alkyl), halogen, —CF$_3$, —CN, —NO$_2$, —N$_3$, —CHO, —CO—(C$_{1-6}$ alkyl), —COOH, —CO—O—(C$_{1-6}$ alkyl), —O—CO—(C$_{1-6}$ alkyl), —CO—NH$_2$, —CO—NH(C$_{1-6}$ alkyl), —CO—N(C$_{1-6}$ alkyl)(C$_{1-6}$ alkyl), —NH—CO—(C$_{1-6}$ alkyl), —N(C$_{1-6}$ alkyl)-CO—(C$_{1-6}$ alkyl), —SO$_2$—NH$_2$, —SO$_2$—NH(C$_{1-6}$ alkyl), —SO$_2$—N(C$_{1-6}$ alkyl)(C$_{1-6}$ alkyl), —NH—SO$_2$—(C$_{1-6}$ alkyl), —N(C$_{1-6}$ alkyl)-SO$_2$—(C$_{1-6}$ alkyl), optionally substituted aryl or optionally substituted heteroaryl, wherein said aryl or said heteroaryl is optionally substituted with one or more groups independently selected from C$_{1-4}$ alkyl, halogen, —CF$_3$, —CN, —OH, —O(C$_{1-4}$ alkyl), —NH$_2$, —NH(C$_{1-4}$ alkyl), or —N(C$_{1-4}$ alkyl)(C$_{1-4}$ alkyl);
B is benzoheteroaryl, wherein the heteroaryl moiety comprised in said benzoheteroaryl is a monocyclic heteroaryl moiety having 5 ring atoms, wherein 1 or 2 ring atoms are each independently selected from oxygen, sulfur or nitrogen and the other ring atoms are carbon atoms;
m is an integer of 0 to 4; and
n is an integer of 0 to 4;
or a pharmaceutically acceptable salt, solvate or prodrug thereof.

2. The compound of item 1, wherein R$^1$ is ethoxy.
3. The compound of item 1 or 2, wherein R$^1$ is in ortho-position with respect to the carbonyl group.
4. The compound of any one of items 1 to 3, wherein each R$^2$ is independently selected from C$_{1-4}$ alkyl, halogen, —CF$_3$, —CN, —OH, —O(C$_{1-4}$ alkyl), —NH$_2$, —NH(C$_{1-4}$ alkyl), or —N(C$_{1-4}$ alkyl)(C$_{1-4}$ alkyl).
5. The compound of any one of items 1 to 4, wherein each R$^3$ is independently selected from C$_{1-4}$ alkyl, halogen, —CF$_3$, —CN, —OH, —O(C$_{1-4}$ alkyl), —NH$_2$, —NH(C$_{1-4}$ alkyl), or —N(C$_{1-4}$ alkyl)(C$_{1-4}$ alkyl).
6. The compound of any one of items 1 to 5, wherein B is benzoheteroaryl, wherein the heteroaryl moiety comprised in said benzoheteroaryl is a monocyclic heteroaryl moiety having 5 ring atoms, wherein 1 or 2 ring atoms are each independently selected from oxygen, sulfur or nitrogen and the other ring atoms are carbon atoms, and further wherein said benzoheteroaryl is attached to the remainder of the compound of formula (I) via the heteroaryl moiety comprised in said benzoheteroaryl.
7. The compound of any one of items 1 to 6, wherein B is indolyl, benzo[b]thienyl, or benzofuranyl.
8. The compound of any one of items 1 to 7, wherein B is 1H-indol-2-yl, 1H-indol-3-yl, 2-benzo[b]thienyl, 3-benzo[b]thienyl, benzofuran-2-yl, or benzofuran-3-yl.
9. The compound of item 1, wherein said compound is a compound of one of the following formulae 13 to 15, 18 to 29 or 31 to 33:

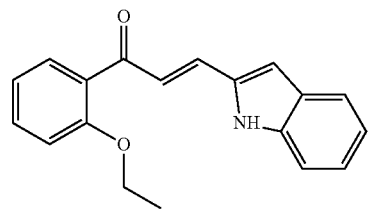

15

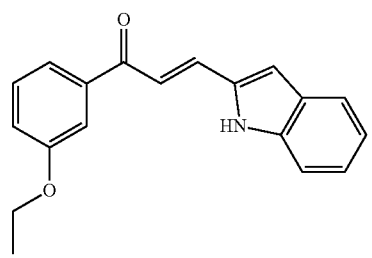

20

21
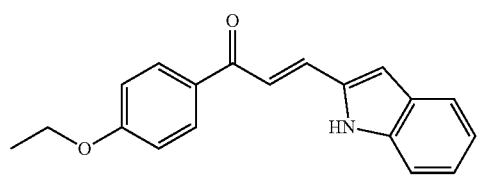
22
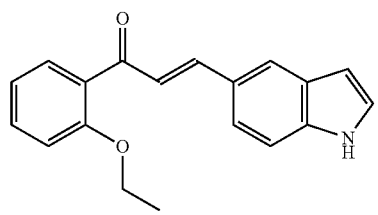
23
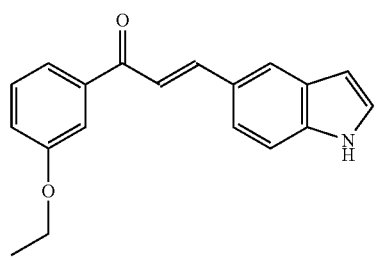
24
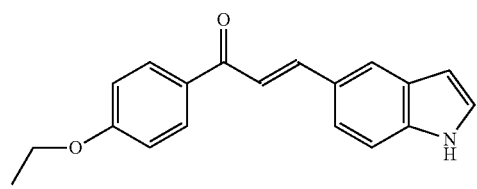
25
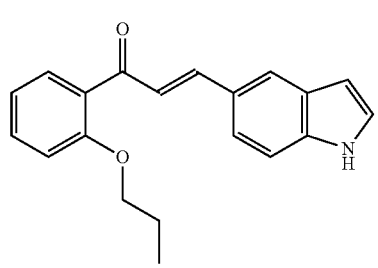
26
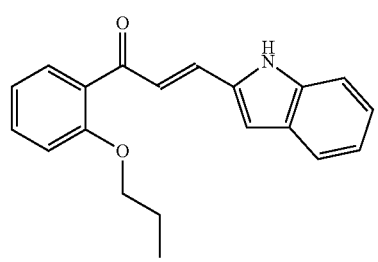
13
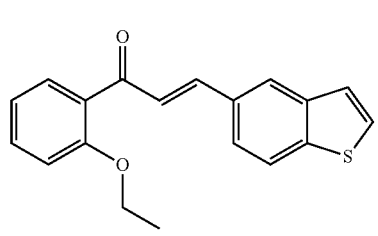
14
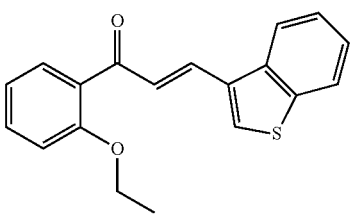
18
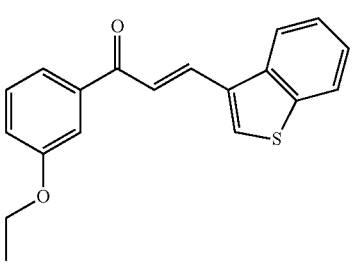
19
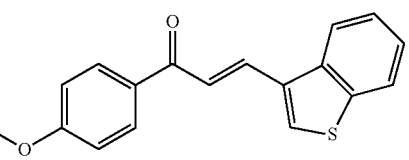
27
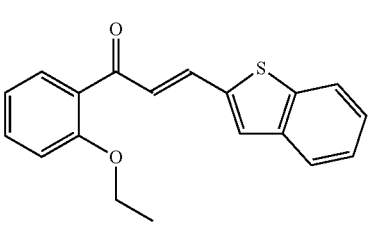
28
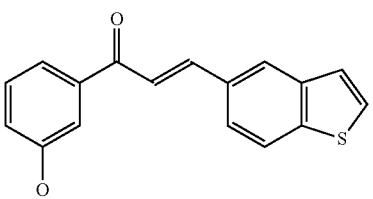
29
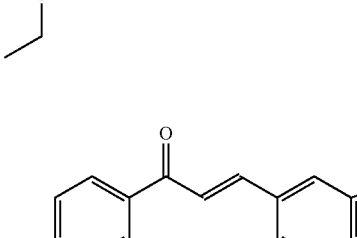
31
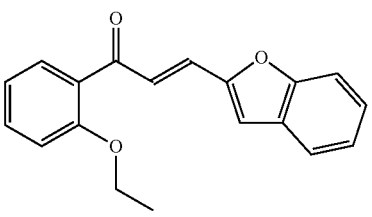

-continued

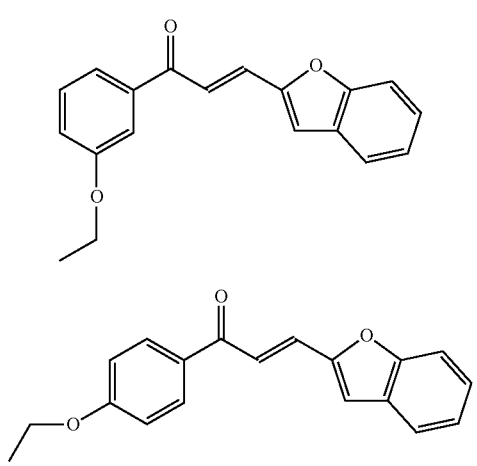

or a pharmaceutically acceptable salt, solvate or prodrug thereof.

10. A pharmaceutical composition comprising the compound of any one of items 1 to 9 and a pharmaceutically acceptable excipient.

11. The compound of any one of items 1 to 9 or the pharmaceutical composition of item 10 for use as a medicament.

12. The compound of any one of items 1 to 9 or the pharmaceutical composition of item 10 for use in the treatment or prevention of cancer.

13. A method of treating or preventing cancer, the method comprising the administration of the compound of any one of items 1 to 9 or the pharmaceutical composition of item 10 to a subject in need thereof.

14. The compound for use according to item 12 or the pharmaceutical composition for use according to item 12 or the method of item 13, wherein the cancer is hematological cancer.

15. The compound for use according to item 14 or the pharmaceutical composition for use according to item 14 or the method of item 14, wherein the hematological cancer is selected from Hodgkin's disease, non-Hodgkin's lymphoma, follicular non-Hodgkin's lymphoma, mantle cell lymphoma, diffuse non-Hodgkin's lymphoma, diffuse large B-cell lymphoma, Burkitt's tumor, peripheral or cutaneous T-cell lymphoma, mycosis fungoides, Sézary's disease, T-zone lymphoma, lymphoepithelioid lymphoma, Lennert's lymphoma, peripheral T-cell lymphoma, lymphosarcoma, a malignant immunoproliferative disease, Waldenström's macroglobulinaemia, alpha heavy chain disease, gamma heavy chain disease, Franklin's disease, an immunoproliferative small intestinal disease, Mediterranean disease, multiple myeloma, Kahler's disease, myelomatosis, plasma cell leukemia, lymphoid leukemia, acute lymphoblastic leukemia, chronic lymphocytic leukemia, subacute lymphocytic leukemia, prolymphocytic leukemia, hairy-cell leukemia, leukemic reticuloendotheliosis, adult T-cell leukemia, myeloid leukemia, acute myeloid leukemia, chronic myeloid leukemia, subacute myeloid leukemia, myeloid sarcoma, chloroma, granulocytic sarcoma, acute promyelocytic leukemia, acute myelomonocytic leukemia, a chronic BCR-ABL negative myeloproliferative disorder, polycythaemia vera, essential thrombocythemia, idiopathic myelofibrosis, monocytic leukemia, acute erythraemia, erythroleukemia, acute erythraemic myelosis, Di Guglielmo's disease, chronic erythraemia, Heilmeyer-Schöner disease, acute megakaryoblastic leukemia, mast cell leukemia, acute panmyelosis, acute myelofibrosis, or Letterer-Siwe disease.

16. The compound for use according to item 12 or the pharmaceutical composition for use according to item 12 or the method of item 13, wherein the cancer is selected from breast cancer, genitourinary cancer, prostate tumor, hormone-refractory prostate tumor, lung cancer, small cell lung tumor, non-small cell lung tumor, gastrointestinal cancer, hepatocellular carcinoma, colorectal tumor, colon cancer, gastric cancer, epidermoid cancer, epidermoid head and/or neck tumor, mouth tumor, melanoma, ovarian cancer, pancreas cancer, neuroblastoma, bladder cancer, renal cancer, or brain cancer.

17. The compound for use according to any one of items 12 or 14 to 16 or the pharmaceutical composition for use according to any one of items 12 or 14 to 16 or the method of any one of items 13 to 16, wherein the compound or the pharmaceutical composition is to be administered in combination with an anticancer drug and/or in combination with radiotherapy.

18. The method of any of items 13 to 17, wherein the subject is a human.

The invention will now be described by reference to the following examples which are merely illustrative and are not to be construed as a limitation of the scope of the present invention.

EXAMPLES

Unless stated otherwise, all chemicals were obtained from Sigma-Aldrich or Apollo Europe and were of analytical grade. Melting points were determined on a Kofler hot stage apparatus and are uncorrected. The $^1$H and 13C NMR spectra were recorded on a BrukerAvance DPx200 (200 and 50 MHz). Chemical shifts are reported in δ units (ppm) relative to Me$_4$Si line as internal standard and J values are reported in Hertz. Mass spectra were obtained by a Hewlett Packard (GC: 5890; MS: 5970) spectrometer. The purity of the synthesized compounds was established by combustion analysis with a Perkin-Elmer 2400 CHN elemental analyzer and was within +0.4%. Solutions in organic solvents were dried over anhydrous sodium sulphate.

Example 1: Synthesis of Chalcone Derivatives

Compounds 1 to 35 as described below, which include compounds of formula (I) according to the present invention as well as reference compounds, were prepared in accordance with the following general synthetic procedure (illustrated in Scheme 1 below):

General Synthetic Procedure

A solution of 2 mmol of the appropriate acetophenone derivative and 3 ml 50% NaOH in 5 ml ethanol was stirred at room temperature for 30 minutes. Then, 2 mmol of the corresponding aldehyde derivative, dissolved in 3 ml ethanol, were added and stirred at room temperature. After complete conversion of the starting materials (monitored by thin layer chromatography (TLC)), the reaction mixture was poured into ice water or extracted with ethyl acetate. The organic layer was dried over anhydrous Na$_2$SO$_4$ and evaporated. The so-obtained crude product was purified by column chromatography or by recrystallization in ethanol.

25

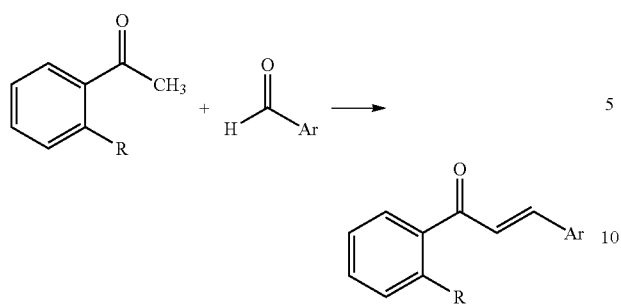

Scheme 1:

Synthetic route to compounds 1-35. Reagents and conditions: 50% NaOH, EtOH, room temperature, 1-24 h.

3-(2-Napthyl)-1-(2-ethoxyphenyl)-2-propen-1-one
(1)

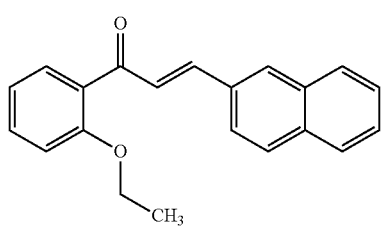 [SMILES: CCOc1ccccc1C(=O)/C=C/c1ccc2ccccc2c1]

Yield: 0.16 g (27%) yellow solid; mp: 96-97° C. $^1$H NMR (CDCl$_3$) δ 8.14-7.39 (m, 11H), 7.21-6.85 (m, 2H), 4.14 (q, J=6.9 Hz, 2H), 1.43 (t, J=6.9 Hz, 3H). $^{13}$C NMR (CDCl$_3$) δ 192.7, 157.7, 142.6, 134.2, 133.4, 133.0, 132.8, 130.6, 130.3, 129.3, 128.6, 128.5, 127.7, 127.4, 127.1, 126.6, 123.6, 120.7, 112.6, 64.2, 14.8. MS m/z 302 (13%, M$^+$), 287 (2%), 273 (3%), 151 (77%), 68 (100%). Anal Calcd for C$_{21}$H$_{18}$O$_2$×0.2H$_2$O. C, 82.44; H, 6.06. Found: C, 82.07; H, 5.62.

1-(2-Methoxyphenyl)-3-(2-naphthyl)-2-propen-1-one (2)

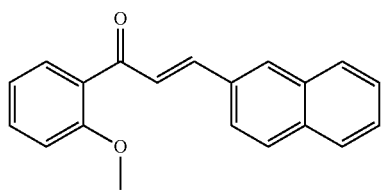 [SMILES: COc1ccccc1C(=O)/C=C/c1ccc2ccccc2c1]

Yield: 0.35 g (60%) yellow solid; mp: 81-83° C. $^1$H NMR (CDCl$_3$) δ 7.96 (s, 1H), 7.91-7.70 (m, 5H), 7.65 (dd, J=7.6 Hz, J=1.6 Hz, 1H), 7.68-7.38 (m, 4H), 7.12-6.96 (m, 2H), 3.92 (s, 3H). $^{13}$C NMR (CDCl$_3$: δ 193.0, 158.1, 143.4, 134.2, 133.3, 132.8, 132.6, 130.4, 130.3, 129.3, 128.6, 128.5, 127.8, 127.2, 127.2, 126.6, 123.7, 120.7, 111.6, 55.8. MS m/z 288 (61%, M$^+$), 287 (42%), 229 (39%), 152 (100%), 135 (47%). Anal Calcd for C$_{20}$H$_{16}$O$_2$: C, 83.31; H, 5.59. Found: C, 83.07; H, 5.64.

3-(2-Naphthyl)-1-(2-propoxyphenyl)-2-propen-1-one
(3)

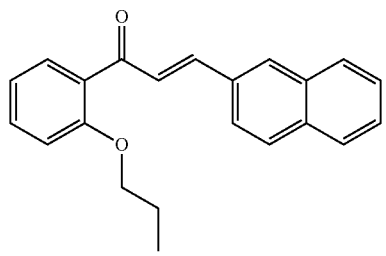 [SMILES: CCCOc1ccccc1C(=O)/C=C/c1ccc2ccccc2c1]

Yield: 0.42 g (66%) yellow oil. $^1$H NMR (CDCl$_3$) δ 7.96 (s, 1H), 7.89-7.65 (m, 6H), 7.65-7.39 (m, 4H), 7.09-6.93 (m, 2H), 4.02 (t, J=6.4 Hz, 2H), 1.92-1.70 (m, 2H), 1.00 (t, J=7.4 Hz, 3H). $^{13}$C NMR (CDCl$_3$: δ 192.7, 157.8, 142.5, 134.2, 133.4, 133.0, 132.7, 130.6, 130.3, 129.4, 128.6, 128.5, 127.7, 127.5, 127.1, 126.6, 123.7, 120.6, 112.4, 70.1, 22.6, 10.7. MS m/z 316 (1%, M$^+$), 141 (9%), 85 (27%), 43 (100%), 41 (20%). Anal Calcd for C$_{22}$H$_{20}$O$_2$: C, 83.51; H, 6.37. Found: C, 83.11; H, 6.09.

1-(2-Butoxyphenyl)-3-(2-naphthyl)-2-propen-1-one
(4)

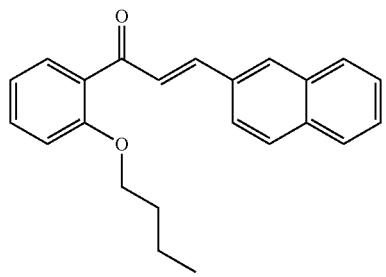 [SMILES: CCCCOc1ccccc1C(=O)/C=C/c1ccc2ccccc2c1]

Yield: 0.23 g (48%) yellow oil. $^1$H NMR (CDCl$_3$) δ 7.98 (s, 1H), 7.90-7.67 (m, 6H), 7.63 (s, 1H), 7.57-7.41 (m, 3H), 7.11-6.95 (m, 2H), 4.09 (t, J=6.3 Hz, 2H), 1.88-1.70 (m, 2H), 1.59-1.38 (m, 2H), 0.87 (t, J=7.3 Hz, 3H). $^{13}$C NMR (CDCl$_3$) δ 192.7, 157.9, 142.5, 134.2, 133.4, 133.0, 132.8, 130.6, 130.3, 129.3, 128.6, 128.5, 127.8, 127.5, 127.1, 126.6, 123.7, 120.6, 112.4, 68.3, 31.3, 19.4, 13.7. MS m/z 330 (12%, M$^+$), 273 (38%), 189 (45%), 141 (100%), 121 (41%). Anal Calcd for C$_{23}$H$_{22}$O$_2$: C, 83.60; H, 6.71. Found: C, 83.17; H, 6.49.

3-(2-Naphthyl)-1-[2-(2-propanoyloxy)phenyl]-2-propen-1-one (5)

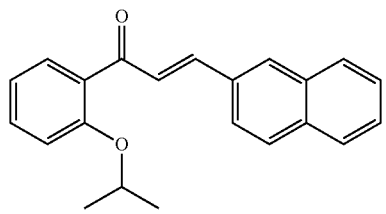 [SMILES: CC(C)Oc1ccccc1C(=O)/C=C/c1ccc2ccccc2c1]

Yield: 0.48 g (76%) yellow solid; mp: 82-85° C. $^1$H NMR (CDCl$_3$) δ 7.98 (s, 1H), 7.91-7.40 (m, 10H), 7.09-6.96 (m, 2H), 4.66 (sept, J=7.0 Hz, 1H), 1.37 (d, J=7.0 Hz, 3H). $^{13}$C NMR (CDCl$_3$) δ 192.9, 156.5, 142.2, 134.0, 133.3, 132.7, 130.6, 130.3, 130.2, 128.5, 128.4, 127.6, 127.4, 127.0, 126.5, 123.4, 120.6, 114.2, 71.0, 22.0. MS m/z 316 (25%, M$^+$), 273 (82%), 154 (100%), 152 (95%), 43 (39%). Anal Calcd for C$_{22}$H$_{20}$O$_2$×0.3H$_2$O: C, 82.11; H, 6.45. Found: C, 82.05; H, 6.33.

1-(2-Methylphenyl)-3-(2-naphthyl)-2-propen-1-one (6)

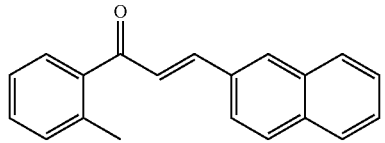 [SMILES: Cc1ccccc1C(=O)/C=C/c1ccc2ccccc2c1]

Yield: 0.25 g (45%) yellow oil. $^1$H NMR (CDCl$_3$) δ 7.93 (s, 1H), 7.90-7.78 (m, 3H), 7.76-7.27 (m, 8H), 7.20 (s, 1H), 2.47 (s, 3H). $^{13}$C NMR (CDCl$_3$) δ 197.0, 146.6, 139.6, 137.4, 134.8, 133.7, 132.6, 131.8, 131.1, 130.9, 129.2, 129.1, 128.5, 128.3, 127.9, 127.3, 127.2, 125.9, 124.0, 20.7. MS m/z 272 (30%, M$^+$), 141 (61%), 119 (100%), 91 (55%), 43 (37%). Anal Calcd for C$_{20}$H$_{16}$O: C, 88.20; H, 5.92. Found: C, 87.88; H, 5.66.

1-(2-Ethoxyphenyl)-3-(6-methoxy-2-naphthyl)-2-propen-1-one (7)

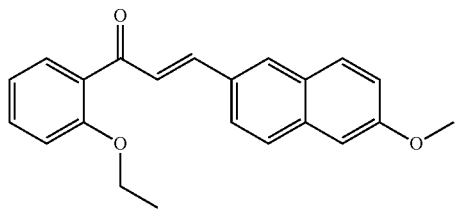 [SMILES: CCOc1ccccc1C(=O)/C=C/c1ccc2cc(OC)ccc2c1]

Yield: 0.46 g (68%) yellow solid; mp: 97-99° C. $^1$H NMR (CDCl$_3$) δ 67.90 (s, 1H), 7.84-7.64 (m, 5H), 7.60-7.39 (m, 2H), 7.20-7.10 (m, 2H), 7.08-6.94 (m, 2H), 4.13 (q, J=7.0 Hz, 2H), 3.92 (s, 3H), 1.43 (t, J=7.0 Hz, 3H). $^{13}$C NMR (CDCl$_3$) δ 192.9, 158.8, 157.6, 143.1, 135.7, 132.9, 130.7, 130.5, 130.2, 130.1, 129.5, 128.8, 127.5, 126.5, 124.4, 120.7, 119.4, 112.6, 106.0, 64.3, 55.4, 14.9. MS m/z 332 (39%, M$^+$), 171 (100%), 139 (65%), 121 (61%), 65 (35%). Anal Calcd for C$_{22}$H$_{20}$O$_3$: C, 79.50; H, 6.06. Found: C, 79.45; H, 5.86.

3-(3-Ethenylphenyl)-1-(2-ethoxyphenyl)-2-propen-1-one (8)

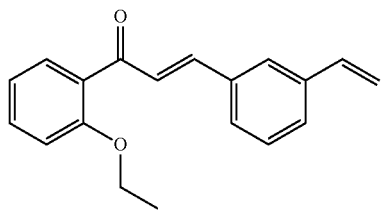 [SMILES: C=Cc1cccc(/C=C/C(=O)c2ccccc2OCC)c1]

Yield: 0.31 g (56%) yellow oil. $^1$H NMR (CDCl$_3$) δ 7.72-7.24 (m, 8H), 7.08-6.91 (m, 2H), 6.74 (dd, J=17.6 Hz, J=10.8 Hz, 1H), 5.78 (dd, J=17.6 Hz, J=0.7 Hz, 1H), 5.29 (dd, J=10.8 Hz, J=0.7 Hz, 1H), 4.12 (q, J=7.0 Hz, 2H), 1.42 (t, J=7.0 Hz, 3H). $^{13}$C NMR (CDCl$_3$) δ 192.5, 157.6, 142.2, 138.1, 136.1, 135.4, 133.0, 130.5, 129.1, 129.0, 127.7, 127.4, 126.1, 120.6, 114.6, 112.5, 64.1, 14.8. MS m/z 278 (7%, M$^+$), 161 (100%), 128 (36%), 121 (74%), 65 (23%). HRMS for C$_{19}$H$_{19}$O$_2$: 279.1385. Found: 279.1389.

3-(1,3-Benzodioxol-5-yl)-1-(2-ethoxyphenyl)-2-propen-1-one (9)

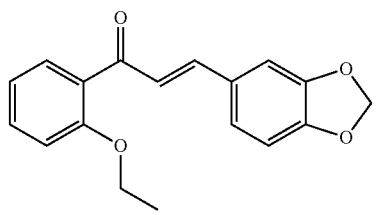 [SMILES: CCOc1ccccc1C(=O)/C=C/c1ccc2c(c1)OCO2]

Yield: 0.29 g (49%) brown solid; mp: 65-70° C. $^1$H NMR (CDCl$_3$) δ 7.69-7.27 (m, 4H), 7.13-6.92 (m, 4H), 6.86-6.77 (m, 1H), 6.00 (s, 2H), 4.13 (q, J=7.0 Hz, 2H), 1.43 (t, J=7.0 Hz, 3H). $^{13}$C NMR (CDCl$_3$) δ 192.6, 157.6, 149.5, 148.3, 142.5, 132.8, 130.5, 129.7, 129.5, 125.4, 124.8, 120.7, 112.6, 108.6, 106.5, 101.5, 64.2, 14.9. MS m/z 296 (4%, M$^+$), 149 (19%), 135 (29%), 121 (25%), 43 (100%). Anal Calcd for C$_{18}$H$_{16}$O$_6$×0.5H$_2$O: C, 70.81; H, 5.60. Found: C, 70.82; H, 5.35.

1-(2-Ethoxyphenyl)-3-(1-naphthyl)-2-propen-1-one (10)

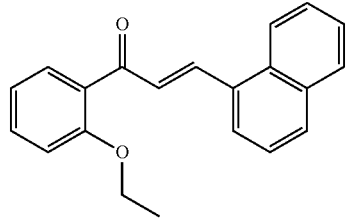 [SMILES: CCOc1ccccc1C(=O)/C=C/c1cccc2ccccc12]

Yield: 0.47 g (78%) yellow solid; mp: 109-110° C. $^1$H NMR (CDCl$_3$) δ 8.57-8.42 (m, 1H), 8.30-8.28 (m, 1H), 7.95-7.78 (m, 3H), 7.77-7.68 (m, 1H), 7.64-7.38 (m, 5H), 7.11-6.92 (m, 2H), 4.13 (q, J=7.0 Hz, 2H), 1.42 (t, J=7.0 Hz, 3H). $^{13}$C NMR (CDCl$_3$) δ 192.6, 157.7, 139.3, 133.7, 133.1, 132.6, 131.7, 130.7, 130.3, 129.7, 129.3, 128.7, 126.7, 126.2, 125.4, 124.9, 123.6, 120.7, 112.6, 64.2, 14.8. MS m/z 302 (40%, M$^+$), 152 (88%), 141 (54%), 121 (98%), 43 (100%). Anal Calcd for C$_{21}$H$_{18}$O$_2$×0.25 toluene: C, 83.97; H, 6.20. Found: C, 84.00; H, 5.82.

3-(9-Anthranyl)-1-(2-ethoxyphenyl)-2-propen-1-one (11)

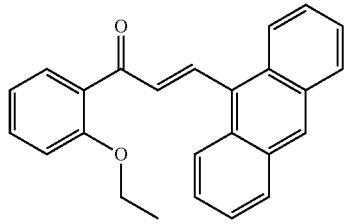 [SMILES: CCOc1ccccc1C(=O)/C=C/c1c2ccccc2cc2ccccc12]

Yield: 0.54 g (76%) yellow solid; mp: 93-96° C. $^1$H NMR (CDCl$_3$) δ 8.66-8.51 (m, 1H), 8.44-8.25 (m, 3H), 8.05-7.91 (m, 2H), 7.81-7.72 (m, 1H), 7.55-7.34 (m, 6H), 7.12-6.99 (m, 1H), 6.98-6.88 (m, 1H), 4.08 (q, J=6.9 Hz, 2H), 1.34 (t, J=6.9 Hz, 3H). $^{13}$C NMR (CDCl$_3$) δ 192.5, 157.7, 139.7, 135.7, 133.2, 131.3, 130.7, 130.4, 129.5, 129.3, 128.8, 128.1, 126.1, 125.5, 125.3, 120.8, 112.4, 64.2, 14.8. MS m/z 352 (31%, M$^+$), 202 (65%), 149 (61%), 121 (100%), 65 (21%). Anal Calcd for C$_{25}$H$_{20}$O$_2$×0.14H$_2$O: C, 84.60; H, 5.76. Found: C, 84.62; H, 5.52.

1-(2-Ethoxyphenyl)-3-(9-phenanthrenyl)-2-propen-1-one (12)

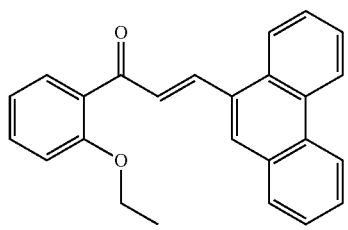 [SMILES: CCOc1ccccc1C(=O)/C=C/c1cc2ccccc2c2ccccc12]

Yield: 0.38 g (54%) yellow solid; mp: 117-120° C. $^1$H NMR (CDCl$_3$) δ 8.78-8.61 (m, 2H), 8.54-8.41 (m, 1H), 8.33-8.21 (m, 1H), 8.06 (s, 1H), 7.94-7.84 (m, 1H), 7.80-7.59 (i, 6H), 7.57-7.41 (m, 1H), 7.12-6.94 (m, 2H), 4.18 (q, J=6.9 Hz, 2H), 1.48 (t, J=6.9 Hz, 3H). $^{13}$C NMR (CDCl$_3$) δ 192.5, 157.8, 140.0, 133.2, 131.8, 131.2, 131.0, 130.7, 130.4, 130.3, 129.3, 129.1, 127.5, 127.0, 126.9, 126.4, 124.5, 123.1, 122.6, 120.8, 112.6, 64.3, 14.9. MS m/z 352 (49%, M$^+$), 202 (83%), 191 (46%), 121 (100%), 57 (53%). Anal Calcd for C$_{25}$H$_{20}$O$_2$: C, 85.20; H, 5.72. Found: C, 85.05; H, 5.44.

3-(5-Benzo[b]thienyl)-1-(2-ethoxyphenyl)-2-propen-1-one (13)

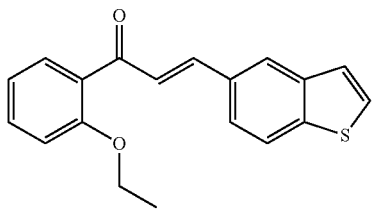 [SMILES: CCOc1ccccc1C(=O)/C=C/c1ccc2sccc2c1]

Yield: 0.090 g (14%) yellow solid; mp: 104-106° C. $^1$H NMR (CDCl$_3$) δ 8.03-7.97 (m, 1H), 7.94-7.33 (m, 8H), 7.10-6.94 (m, 2H), 4.15 (q, J=7.0 Hz, 2H), 1.44 (t, J=7.0 Hz, 3H). $^{13}$C NMR (CDCl$_3$) δ 192.8, 157.7, 142.9, 140.1, 132.9, 131.7, 130.6, 129.5, 127.5, 126.9, 124.6, 124.1, 123.2, 122.9, 120.7, 112.6, 64.3, 14.9. MS m/z 308 (11%, M$^+$), 279 (14%), 161 (38%), 147 (100%), 121 (37%), 65 (21%). Anal Calcd for C$_{19}$H$_{16}$O$_2$S×0.15H$_2$O: C, 73.36; H, 5.28. Found: C, 73.44; H, 4.95.

3-(1-Benzothien-3-yl)-1-(2-ethoxyphenyl)-2-propen-1-one (14)

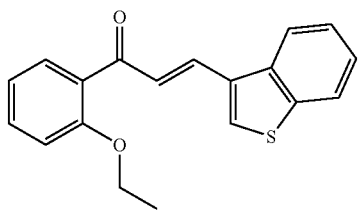 [SMILES: CCOc1ccccc1C(=O)/C=C/c1csc2ccccc12]

Yield: 0.39 g (63%) yellow oil. $^1$H NMR (CDCl$_3$) δ 8.13-7.81 (m, 3H), 7.80-7.56 (m, 3H), 7.50-7.33 (m, 3H), 7.10-6.90 (m, 2H), 4.12 (q, J=7.0 Hz, 2H), 1.41 (t, J=7.0 Hz, 3H). $^{13}$C NMR (CDCl$_3$) δ 192.3, 157.7, 140.5, 137.3, 134.1, 133.1, 132.5, 130.7, 129.2, 128.3, 127.4, 125.0, 124.8, 122.9, 122.2, 120.7, 112.6, 64.2, 14.8. MS m/z 308 (43%, M$^+$), 147 (100%), 121 (98%), 43 (89%), 41 (30%). Anal Calcd for C$_{19}$H$_{16}$O$_2$S: C, 74.00; H, 5.23. Found: C, 73.71; H, 4.92.

1-(2-Ethoxyphenyl)-3-(1H-indole-2-yl)-2-propen-1-one (15)

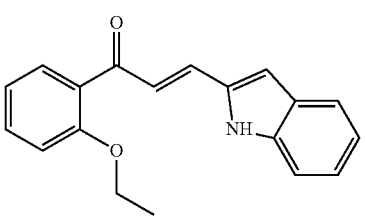 [SMILES: CCOc1ccccc1C(=O)/C=C/c1cc2ccccc2[nH]1]

Yield: 0.22 g (38%) brown solid; mp: 124-126° C. $^1$H NMR (CDCl$_3$) δ 9.05 (sbr, 1H), 7.72-7.54 (m, 3H), 7.49-6.89 (m, 7H), 6.87-6.80 (m, 1H), 4.08 (q, J=7.0 Hz, 2H), 1.37 (t, J=7.0 Hz, 3H). $^{13}$C NMR (CDCl$_3$) δ 192.9, 157.4, 138.0, 134.3, 133.3, 132.8, 130.3, 129.2, 128.5, 124.9, 124.5, 121.4, 120.6, 120.4, 112.6, 111.3, 108.8, 64.3, 14.7. MS m/z 291 (63%, M$^+$), 262 (42%), 130 (61%), 119 (100%), 91 (49%). Anal Calcd for C$_{19}$H$_{17}$NO$_2$: C, 78.33; H, 5.88; N, 4.81. Found: C, 78.24; H, 5.67; N, 4.79.

3-(2-Napthyl)-1-(3-ethoxyphenyl)-2-propen-1-one (16)

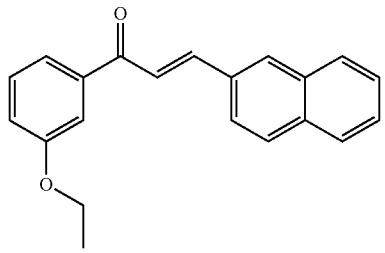 [SMILES: CCOc1cccc(C(=O)/C=C/c2ccc3ccccc3c2)c1]

Yield: 0.21 g (34%) yellow solid; mp: 97-100° C. $^1$H NMR (CDCl$_3$) δ 8.03-7.76 (m, 6H), 7.66-6.37 (m, 6H), 7.15-7.05 (m, 1H), 4.12 (q, J=7.0 Hz, 2H), 1.45 (t, J=7.0 Hz, 3H). $^{13}$C NMR (CDCl$_3$) δ 190.4, 159.4, 145.0, 139.8, 134.6, 133.5, 132.6, 130.8, 129.8, 128.9, 128.8, 128.0, 127.5, 126.9, 123.9, 122.4, 121.1, 119.8, 113.8, 63.9, 15.0. MS m/z 302 (100%, M$^+$), 181 (36%), 152 (84%), 128 (18%), 65 (15%). Anal Calcd for C$_{21}$H$_{18}$O$_2$. C, 83.42; H, 6.00. Found: C, 83.12; H, 5.95.

3-(2-Napthyl)-1-(4-ethoxyphenyl)-2-propen-1-one (17)

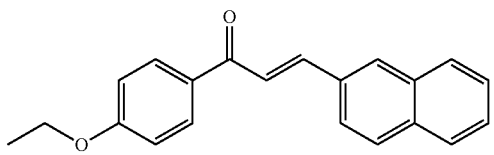 [SMILES: CCOc1ccc(C(=O)/C=C/c2ccc3ccccc3c2)cc1]

Yield: 0.44 g (73%) yellow solid; mp: 159-161° C. $^1$H NMR (CDCl$_3$) δ 8.09-7.48 (m, 11H), 6.97 (d, J=8.8 Hz, 2H), 4.11 (q, J=7.0 Hz, 2H), 1.45 (t, J=7.0 Hz, 3H). $^{13}$C NMR (CDCl$_3$) δ 188.8, 163.0, 144.1, 134.4, 133.5, 132.8, 131.1, 131.0, 130.6, 128.8, 128.8, 127.9, 127.4, 126.9, 123.9, 122.2, 114.5, 63.9, 14.9. MS m/z 302 (99%, M$^+$), 273 (36%), 152 (100%), 121 (59%), 65 (37%). Anal Calcd for C$_{21}$H$_{18}$O$_2$. C, 83.42; H, 6.00. Found: C, 83.07; H, 5.87.

3-(1-Benzothien-3-yl)-1-(3-ethoxyphenyl)-2-propen-1-one (18)

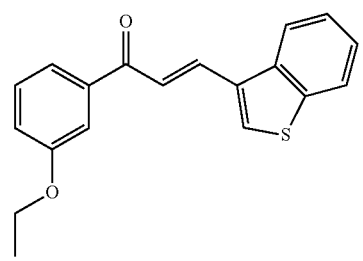 [SMILES: CCOc1cccc(C(=O)/C=C/c2csc3ccccc23)c1]

Yield: 0.21 g (34%) yellow solid; mp: 103-106° C. $^1$H NMR (CDCl$_3$) δ 8.15-8.07 (m, 2H), 7.92-7.88 (m, 2H), 7.65-7.38 (m, 6H), 7.16-7.11 (m, 1H), 4.12 (q, J=7.0 Hz, 2H), 1.45 (t, J=7.0 Hz, 3H). $^{13}$C NMR (CDCl$_3$) δ 190.3, 159.5, 140.7, 139.7, 137.5, 136.5, 132.5, 129.8, 128.9, 125.3, 125.2, 123.3, 122.7, 122.4, 121.0, 119.9, 113.8, 63.9, 15.0. MS m/z 308 (60%, M$^+$), 279 (26%), 187 (48%), 115 (100%), 69 (56%). Anal Calcd for C$_{19}$H$_{16}$O$_2$S: C, 74.00; H, 5.23. Found: C, 73.99; H, 4.87.

3-(1-Benzothien-3-yl)-1-(4-ethoxyphenyl)-2-propen-1-one (19)

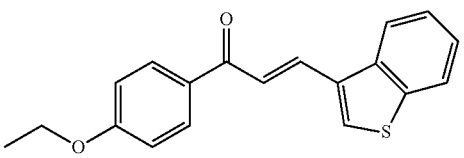 [SMILES: CCOc1ccc(C(=O)/C=C/c2csc3ccccc23)cc1]

Yield: 0.45 g (74%) yellow solid; mp: 129-130° C. $^1$H NMR (CDCl$_3$) δ 8.14-8.04, (m, 4H), 7.92-7.88 (m, 2H), 7.65 (AB-system, J$_{AB}$=15.6 Hz, 1H), 7.50-7.41 (m, 2H), 7.00-6.96 (m, 2H), 4.12 (q, J=7.0 Hz, 2H), 1.46 (t, J=7.0 Hz, 3H). $^{13}$C NMR (CDCl$_3$) δ 188.7, 163.1, 140.7, 137.6, 132.7, 131.1, 131.0, 128.3, 125.3, 125.2, 123.2, 122.5, 122.4, 114.5, 64.0, 14.9. MS m/z 308 (100%, M$^+$), 279 (27%), 251 (25%), 115 (35%), 65 (10%). Anal Calcd for C$_{19}$H$_{16}$O$_2$S× 0.13H$_2$O: C, 73.44; H, 5.27. Found: C, 73.24; H, 4.87.

1-(3-Ethoxyphenyl)-3-(1H-indole-2-yl)-2-propen-1-one (20)

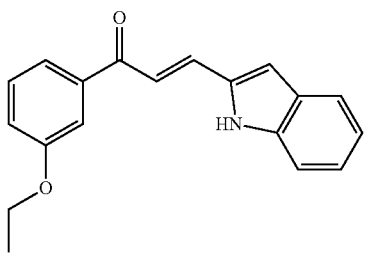 [SMILES: CCOc1cccc(C(=O)/C=C/c2cc3ccccc3[nH]2)c1]

Yield: 0.18 g (31%) brown solid; mp: 156-158° C. $^1$H NMR (CDCl$_3$) δ 8.99 (s, 1H), 7.85 (d, J=15.6 Hz, 1H), 7.65-7.07 (m, 9H), 6.91 (s, 1H), 4.03 (q, J=7.0 Hz, 2H), 1.40 (t, J=7.0 Hz, 3H). $^{13}$C NMR (CDCl$_3$) δ190.3, 159.4, 139.7, 135.0, 134.3, 129.8, 128.7, 125.1, 121.9, 121.0, 120.9, 119.9, 119.6, 113.7, 111.5, 110.3, 63.9, 14.9. MS m/z 291 (100%, M$^+$), 262 (71%), 234 (49%), 170 (35%), 115 (32%). Anal Calcd for C$_{19}$H$_{17}$NO$_2$: C, 78.33; H, 5.88. Found: C, 78.20; H, 5.56.

1-(4-Ethoxyphenyl)-3-(1H-indole-2-yl)-2-propen-1-one (21)

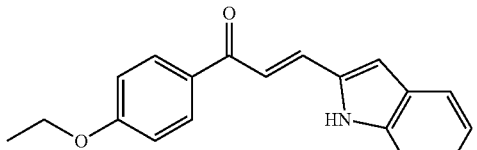

33

Yield: 0.09 g (15%) brown solid; mp: 178-181° C. $^1$H NMR (CDCl$_3$) δ 8.83 (sbr, 1H), 8.03-6.90 (m, 11H), 4.07 (q, J=7.0 Hz, 2H), 1.43 (t, J=7.0 Hz, 3H). $^{13}$C NMR (CDCl$_3$) δ 188.5, 163.1, 138.1, 134.0, 131.0, 130.9, 128.8, 125.0, 121.8, 120.9, 119.5, 114.5, 111.4, 109.8, 64.0, 14.9. MS m/z 291 (100%, M$^+$), 262 (43%), 234 (29%), 117 (44%), 65 (30%). Anal Calcd for C$_{19}$H$_{17}$NO$_2$: C, 78.33; H, 5.88, N, 4.81. Found: C, 78.18; H, 5.40, N, 4.77.

(E)-1-(2-Ethoxyphenyl)-3-(1H-indol-5-yl)-2-propen-1-one (22)

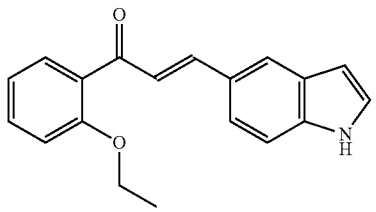 [SMILES: CCOc1ccccc1C(=O)/C=C/c1ccc2[nH]ccc2c1]

Yield: 0.26 g (45%) yellow solid; mp: 151-153° C. $^1$H NMR (CDCl$_3$): δ 8.48 (s, 1H), 7.89-7.80 (m, 2H), 7.69-7.60 (m, 1H), 7.54-7.34 (m, 4H), 7.28-7.19 (m, 1H), 7.09-6.94 (m, 2H), 6.62-6.54 (m, 1H), 4.13 (q, J=6.9 Hz, 2H), 1.42 (t, J=6.9 Hz, 3H). $^{13}$C NMR (CDCl$_3$): δ 193.5, 157.4, 145.4, 137.1, 132.4, 130.3, 129.9, 128.2, 127.2, 125.3, 124.6, 122.8, 121.8, 120.6, 112.6, 111.6, 103.4, 64.3, 14.8. MS m/z 291 (18%, M$^+$), 130 (93%), 69 (100%), 55 (72%), 43 (87%). Anal. Calcd for C$_{19}$H$_{17}$NO$_2$: C, 78.33; H, 5.88; N, 4.81. Found: C, 78.23; H, 5.68; N, 4.73.

(E)-1-(3-Ethoxyphenyl)-3-(1H-indol-5-yl)-2-propen-1-one (23)

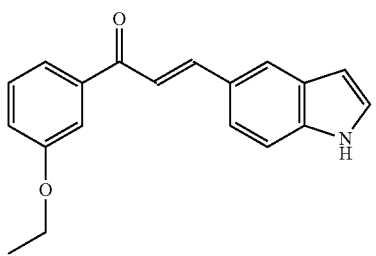 [SMILES: CCOc1cccc(C(=O)/C=C/c2ccc3[nH]ccc3c2)c1]

Yield: 0.11 g (19%); mp: 121-123° C. $^1$H NMR (CDCl$_3$): δ 7.31-8.76 (m, 9H), 7.08-7.13 (m, 1H), 6.60 (d, J=3.2 Hz, 1H), 5.70 (s, 1H), 4.10 (q, J=7.0 Hz, 2H), 1.43 (t, J=7.0 Hz, 3H). $^{13}$C NMR (CDCl$_3$): δ 190.9, 159.3, 147.3, 140.3, 137.3, 129.7, 128.4, 127.1, 125.5, 123.3, 122.2, 121.0, 119.5 (2C), 113.7, 111.8, 103.7, 63.9, 15.0. MS m/z 291 (100%, M$^+$), 262 (23%), 170 (73%), 117 (82%), 65 (35%). Anal. Calcd for C$_{19}$H$_{17}$NO$_2$:C, 78.33; H, 5.88; N, 4.81. Found: C, 77.92; H, 5.51; N, 4.70.

34

(E)-1-(4-Ethoxyphenyl)-3-(1H-indol-5-yl)-2-propen-1-one (24)

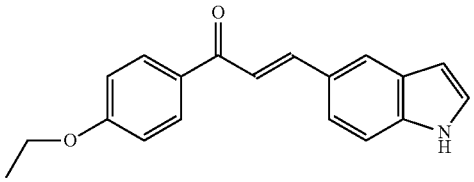 [SMILES: CCOc1ccc(C(=O)/C=C/c2ccc3[nH]ccc3c2)cc1]

Yield: 0.35 g (60%); mp: 171-173° C. $^1$H NMR (DMSO-d$_6$): δ 11.40 (s, 1H), 8.22-8.08 (m, 3H), 7.88 (s, 2H), 7.73 (d, J=8.0 Hz, 1H), 7.49 (m, 2H), 7.09 (d, J=8.8 Hz, 2H), 6.55 (d, J=2.6 Hz, 1H), 4.17 (q, J=7.0 Hz, 2H), 1.40 (t, J=7.0 Hz, 3H). $^{13}$C NMR (DMSO-d$_6$): δ 187.2, 162.2, 145.6, 137.3, 130.7, 130.7, 127.9, 126.6, 126.0, 122.8, 121.5, 118.2, 114.3, 111.9, 102.1, 63.5, 14.5. MS m/z 291 (100%, M$^+$), 262 (49%), 170 (40%), 117 (46%), 65 (48%). Anal. Calcd for C$_{19}$H$_{17}$NO$_2$ 0.1 mol EtOH: C, 77.92; H, 5.99; N, 4.73. Found: C, 77.56; H, 5.69; N, 4.73.

(E)-3-(1H-indol-5-yl)-1-(2-propoxyphenyl)-2-propen-1-one (25)

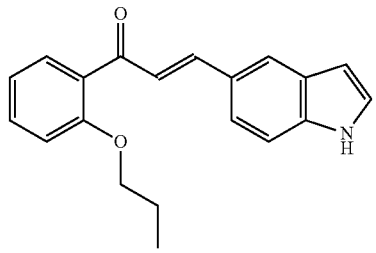 [SMILES: CCCOc1ccccc1C(=O)/C=C/c1ccc2[nH]ccc2c1]

Yield: 0.35 g (57%) brown solid; mp: 114-116° C. $^1$H NMR (CDCl$_3$): δ 10.2 (s, 1H), 7.89-7.34 (m, 7H), 7.28-7.19 (m, 1H), 7.09-6.95 (m, 2H), 6.58-6.49 (m, 1H), 4.03 (t, J=6.4 Hz, 2H), 1.93-1.71 (m, 2H), 1.00 (t, J=7.4 Hz, 3H). $^{13}$C NMR (CDCl$_3$): δ 193.0, 157.1, 145.3, 137.1, 132.1, 129.8, 129.5, 127.8, 126.1, 125.4, 123.8, 122.4, 120.8, 120.1, 112.1, 111.6, 102.2, 69.7, 22.2, 10.3. MS m/z 305 (14%, M$^+$), 262 (15%), 130 (100%), 115 (36%), 43 (19%). Anal. Calcd for C$_{20}$H$_{19}$NO$_2$: C, 78.66; H, 6.27; N, 4.59. Found: C, 78.58; H, 6.04; N, 4.54.

(E)-3-(1H-indol-2-yl)-1-(2-propoxyphenyl)-2-propen-1-one (26)

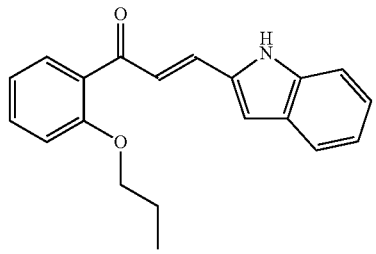 [SMILES: CCCOc1ccccc1C(=O)/C=C/c1cc2ccccc2[nH]1]

Yield: 0.20 g (32%) yellow solid; mp: 112-114° C. $^1$H NMR (CDCl$_3$): δ 8.7 (s, 1H), 7.73-7.57 (s, 3H), 7.51-7.31 (m, 4H), 7.30-6.93 (m, 3H), 6.90-6.82 (m, 1H), 4.01 (t, J=6.4 Hz, 2H), 1.90-1.70 (m, 2H), 1.00 (t, J=7.4 Hz, 3H). $^{13}$C NMR (CDCl$_3$): δ 192.6, 157.6, 137.9, 134.3, 132.9, 132.8, 130.4, 129.3, 128.6, 124.9, 124.5, 121.5, 120.7, 120.5, 112.5, 111.2, 109.0, 70.2, 22.6, 10.7. MS m/z 305 (37%, M$^+$), 130 (55%), 115 (39%), 69 (100%), 43 (99%). Anal. Calcd for C$_{20}$H$_{19}$NO$_2$: C, 78.66; H, 6.27; N, 4.59. Found: C, 78.52; H, 6.07; N, 4.53.

(E)-3-(1-Benzothiophen-2-yl)-1-(2-ethoxyphenyl)-2-propen-1-one (27)

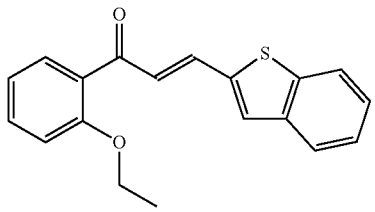 [SMILES: CCOc1ccccc1C(=O)/C=C/c1cc2ccccc2s1]

Yield: 0.32 g (51%) orange solid; mp: 95-98° C. $^1$H NMR (CDCl$_3$): δ 7.95-7.82 (m, 1H), 7.81-7.69 (m, 3H), 7.52-7.30 (m, 5H), 7.08-6.90 (m, 2H), 4.13 (q, J=7.0 Hz, 2H), 1.49 (t, J=7.0 Hz, 3H). $^{13}$C NMR (CDCl$_3$): δ 191.2, 158.0, 140.9, 140.0, 139.8, 135.0, 133.4, 130.8, 129.1, 128.7, 128.5, 126.1, 124.8, 124.3, 122.4, 120.7, 112.5, 64.2, 14.9. MS m/z 308 (20%, M$^+$), 147 (83%), 69 (100%), 43 (100%), 41 (73%). Anal. Calcd for C$_{19}$H$_{16}$O$_2$S: C, 74.00; H, 5.23. Found: C, 74.04; H, 5.08.

(E)-3-(1-Benzothiophen-2-yl)-1-(3-ethoxyphenyl)-2-propen-1-one (28)

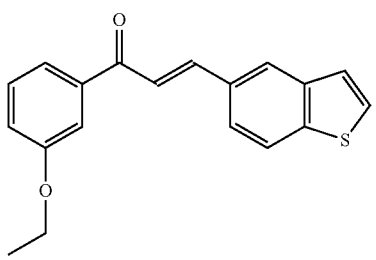 [SMILES: CCOc1cccc(C(=O)/C=C/c2ccc3sccc3c2)c1]

Yield: 0.49 g (79%); mp: 98-99° C. $^1$H NMR (CDCl$_3$): δ 8.05 (d, J=1.4 Hz, 1H), 7.99-7.88 (m, 2H), 7.68-7.37 (m, 7H), 7.15-7.09 (m, 1H), 4.12 (q, J=7.0 Hz, 2H), 1.45 (t, J=7.0 Hz, 3H). $^{13}$C NMR (CDCl$_3$): δ 190.4, 159.4, 145.3, 142.0, 140.4, 139.8, 131.5, 129.7, 127.8, 124.9, 123.5, 123.1, 121.8, 121.1, 119.8, 113.8, 63.9, 15.0. MS m/z 308 (69%, M$^+$), 307 (60%), 187 (45%), 115 (100%), 65 (44%). Anal. Calcd for C$_{19}$H$_{16}$O$_2$S: C, 74.00; H, 5.23. Found: C, 73.84; H, 4.88.

(E)-3-(1-Benzothiophen-2-yl)-1-(4-ethoxyphenyl)-2-propen-1-one (29)

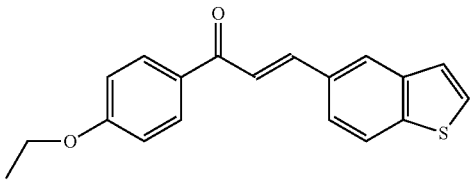 [SMILES: CCOc1ccc(C(=O)/C=C/c2ccc3sccc3c2)cc1]

Yield: 0.46 g (74%); mp: 149-151° C. $^1$H NMR (CDCl$_3$): δ 8.09-8.07 (m, 3H), 8.03-7.87 (m, 2H), 7.68-7.58 (m, 2H), 7.48 (A-part of an AB-system, J$_{AB}$=5.6 Hz, 1H), 7.37 (B-part of an AB-system, J$_{AB}$=5.6 Hz, 1H), 7.00-6.93 (m, 2H), 4.11 (q, J=7.0 Hz, 2H), 1.45 (t, J=7.0 Hz, 3H). $^{13}$C NMR (CDCl$_3$): δ 188.8, 163.0, 144.4, 141.7, 140.2, 131.6, 131.2, 131.0, 127.7, 124.8, 124.3, 123.5, 123.0, 121.5, 114.4, 63.9, 14.9. MS m/z 308 (100%, M$^+$), 307 (61%), 279 (40%), 115 (38%), 65 (9%). Anal. Calcd for C$_{19}$H$_{16}$O$_2$S: C, 74.00; H, 5.23. Found: C, 73.73; H, 4.82.

(E)-3-(2,2'-bithiophen-5-yl)-1-(2-ethoxyphenyl)-2-propen-1-one (30)

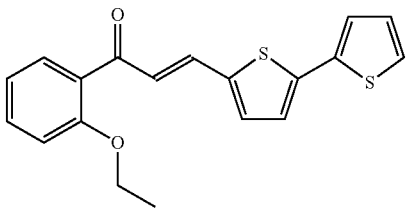 [SMILES: CCOc1ccccc1C(=O)/C=C/c1ccc(-c2cccs2)s1]

Yield: 0.32 g (47%) brown oil. $^1$H NMR (CDCl$_3$): δ 7.80-7.65 (m, 2H), 7.50-7.38 (m, 1H), 7.36-7.15 (m, 4H), 7.14-7.08 (m, 1H), 7.07-6.90 (m, 3H), 4.13 (q, J=7.0 Hz, 2H), 1.47 (t, J=7.0 Hz, 3H). $^{13}$C NMR (CDCl$_3$): δ 191.5, 157.8, 140.1, 139.5, 136.8, 134.6, 133.1, 132.7, 130.7, 129.0, 128.0, 125.9, 125.6, 124.7, 124.5, 120.7, 112.5, 64.2, 14.9. MS m/z 340 (38%, M$^+$), 179 (100%), 147 (20%), 121 (36%), 57 (56%). Anal. Calcd for C$_{19}$H$_{16}$O$_2$S$_2$: C, 67.03; H, 4.74. Found: C, 66.73; H, 4.39.

(E)-3-(1-Benzofuran-2-yl)-1-(2-ethoxyphenyl)-2-propen-1-one (31)

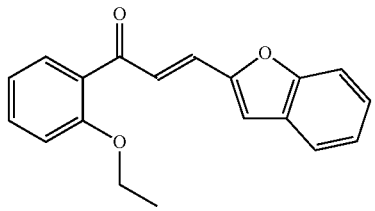 [SMILES: CCOc1ccccc1C(=O)/C=C/c1cc2ccccc2o1]

Yield: 0.35 g (60%) yellow solid; mp: 79-81° C. $^1$H NMR (CDCl$_3$): δ 7.78-7.62 (m, 2H), 7.61-7.16 (m, 6H), 7.08-6.91 (m, 3H), 4.14 (q, J=7.0 Hz, 2H), 1.46 (t, J=7.0 Hz, 3H). $^{13}$C NMR (CDCl$_3$): δ 191.6, 158.0, 155.4, 153.4, 133.3, 130.6, 128.9, 128.5, 127.5, 126.2, 123.2, 121.6, 120.6, 112.6, 111.3, 111.2, 64.3, 14.6. MS m/z 292 (16%, M⁺), 131 (100%), 121 (37%), 115 (35%), 65 (18%). Anal. Calcd for $C_{19}H_{16}O_3$: C, 78.06; H, 5.52. Found: C, 77.58; H, 5.25.

(E)-3-(1-Benzofuran-2-yl)-1-(3-ethoxyphenyl)-2-propen-1-one (32)

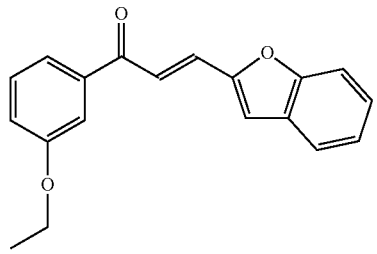 [SMILES: CCOc1cccc(C(=O)/C=C/c2cc3ccccc3o2)c1]

Yield: 0.33 g (56%); mp: 127-129° C. ¹H NMR (CDCl₃): δ 7.70-7.58 (m, 5H), 7.55-7.50 (m, 1H), 7.46-7.34 (m, 2H), 7.29-7.21 (m, 1H), 7.16-7.10 (m, 1H), 7.03 (s, 1H), 4.13 (q, J=7.0 Hz, 2H), 1.46 (t, J=7.0 Hz, 3H). ¹³C NMR (CDCl₃): δ 189.5, 159.5, 155.8, 153.2, 139.5, 131.0, 129.8, 128.7, 126.9, 123.6, 122.2, 122.0, 121.2, 120.1, 113.7, 112.7, 111.6, 63.9, 15.0. MS m/z 292 (100%, M⁺), 235 (44%), 207 (22%), 171 (45%), 115 (58%). Anal. Calcd for $C_{19}H_{16}O_3$: C, 78.06; H, 5.52. Found: C, 77.83; H, 5.22.

(E)-3-(1-Benzofuran-2-yl)-1-(4-ethoxyphenyl)-2-propen-1-one (33)

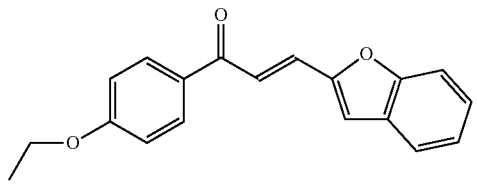 [SMILES: CCOc1ccc(C(=O)/C=C/c2cc3ccccc3o2)cc1]

Yield: 0.43 g (74%); mp: 100-101° C. ¹H NMR (CDCl₃): δ 8.11-8.05 (m, 2H), 7.79-7.70 (m, 2H), 7.62-7.50 (m, 2H), 7.41-7.21 (m, 2H), 7.00-6.94 (m, 3H), 4.12 (q, J=7.0 Hz, 2H), 1.45 (t, J=7.0 Hz, 3H). ¹³C NMR (CDCl₃): δ 187.9, 163.2, 155.7, 153.4, 131.1, 130.9, 130.2, 128.8, 126.7, 123.5, 122.1, 122.0, 114.5, 112.2, 111.5, 64.0, 14.9. MS m/z 292 (100%, M⁺), 264 (30%), 235 (36%), 171 (28%), 121 (54%). Anal. Calcd for $C_{19}H_{16}O_3$: C, 78.06; H, 5.52. Found: C, 77.83; H, 5.16.

(E)-3-(1,3-benzodioxol-5-yl)-1-(3-ethoxyphenyl)prop-2-en-1-one (34)

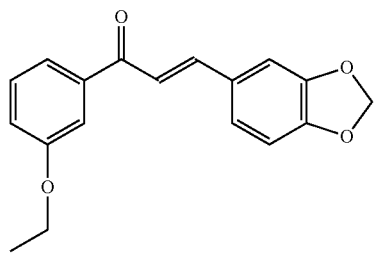 [SMILES: CCOc1cccc(C(=O)/C=C/c2ccc3c(c2)OCO3)c1]

Yield: 0.49 g (83%); mp: 119-120° C. ¹H NMR (CDCl₃): δ 87.73 (d, J=15.0 Hz, 1H), 7.60-7.51 (m, 2H), 7.43-7.30 (m, 2H), 7.17-7.08 (m, 3H), 6.84 (d, J=8.0 Hz, 1H), 6.03 (s, 2H), 4.11 (q, J=7.0 Hz, 2H), 1.45 (t, J=7.0 Hz, 3H). ¹³C NMR (CDCl₃): δ 190.3, 159.4, 150.1, 148.6, 144.8, 139.9, 129.7, 129.5, 125.4, 121.0, 120.3, 119.7, 113.7, 108.8, 106.8, 101.8, 63.9, 15.0. MS m/z 296 (100%, M⁺), 267 (22%), 145 (33%), 89 (37%), 65 (30%). Anal. Calcd for $C_{18}H_{16}O_4$: C, 72.96; H, 5.44. Found: C, 72.72; H, 4.99.

(E)-3-(1,3-benzodioxol-5-yl)-1-(3-ethoxyphenyl)prop-2-en-1-one (35)

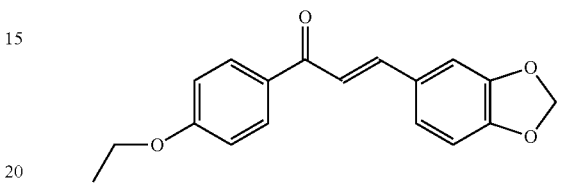

Yield: 0.44 g (75%); mp: 98-100° C. ¹H NMR (CDCl₃): δ 8.01 (d, J=6.7 Hz, 2H), 7.72 (A-part of an AB-system, $J_{AB}$=15.4 Hz, 1H), 7.38 (B-part of an AB-system, $J_{AB}$=15.4 Hz, 1H), 7.17-7.09, (m, 2H), 6.99-6.92 (m, 2H), 6.83 (d, J=8.0 Hz, 1H), 6.02 (s, 2H), 4.11 (q, J=7.0 Hz, 2H), 1.45 (t, J=7.0 Hz, 3H). ¹³C NMR (CDCl₃): δ 188.7, 162.9, 149.9, 148.5, 143.9, 131.2, 130.9, 129.7, 125.2, 120.1, 114.4, 108.8, 106.8, 101.7, 63.9, 14.9. MS m/z 296 (100%, M⁺), 267 (41%), 121 (35%), 89 (25%), 65 (25%). Anal. Calcd for $C_{18}H_{16}O_4$: C, 72.96; H, 5.44. Found: C, 72.77; H, 4.98.

Example 2: Structure-Activity Relationship (SAR)-Guided Development of Potent Antitumor Compounds Materials and Methods Cell Lines and Patients Hematological cell lines were acquired from the Leibniz Institute DSMZ-German Collection of Microorganisms and Cell Cultures (www.dsmz.de). Sixteen patients diagnosed with chronic lymphocytic leukemia at the Division of Hematology and Hemostaseology at the Vienna General Hospital and four healthy donors were included in the study. All participants signed informed consent according to the Declaration of Helsinki (Ethics Committee Nr: EK 1722/2012). Peripheral blood mononuclear cells (PBMC) were isolated using standardized Ficoll-Hypaque gradient centrifugation (Seromed, Berlin, Germany) and stored in liquid nitrogen until use.

Cell Culture

JURKAT and CCRF-CEM (T-cell acute lymphoblastic leukemia), HL60 and K562 representing acute and chronic myeloid leukemia, respectively, the chronic lymphocytic leukemia cell line MEC-1, and the diffuse large B-cell lymphoma cell line U-2940 were cultured in Gibco RPMI 1640+GlutaMAX (Life Technologies, Carlsbad, Calif., USA) supplemented with 10% fetal bovine serum gold (FBS gold; PAA Laboratories, Pasching, Austria) and 1% Pen-Strep (100 U/ml penicillin and 100 μg/ml streptomycin; PAA Laboratories), and maintained at 37° C. in humidified atmosphere with 5% CO₂. The diffuse large B-cell lymphoma cell line OCI-LY7 was cultured in Gibco IMDM+GlutaMAX and 25 mM HEPES (Life Technologies) containing 20% FBS gold and 1% PenStrep.

Primary Cells

Primary cells were thawed in Gibco RPMI 1640+L-glutamine (PAA Laboratories) supplemented with 20% FBS gold and cultured overnight at standard conditions before cells were incubated with the compounds.

Viability Tests

All experiments with hematological cell lines were done using phenol red-free RPMI 1640+L-glutamine (PAA Laboratories) supplemented with 1% PenStrep and 10% FBS gold, except experiments with OCI-Ly7 which were carried out in Gibco IMEM+GlutaMAX and 25 mM HEPES containing 20% FBS gold and 1% PenStrep. Cells were incubated in triplicates with increasing concentrations of the compounds for 48 h, changes in viability were determined using the cell proliferation and cytotoxicity assays EZ4U (Biomedica Group, Austria) and CellTiter-Blue Cell Viability Assay (Promega, Madison, Wis., USA) following instructions of the manufacturers. $IC_{50}$ values were calculated from two independent experiments using GraphPad Prism 5 software.

Primary cells were incubated at a density of 300,000 cells per well in 96-well plates in a total volume of 100 µl of Gibco RPMI 1640+L-glutamine (PAA Laboratories) supplemented with 20% FBS gold with increasing concentrations of compounds for 48 h. For co-culture experiments, 150,000 M2-10B4 mouse fibroblast cells were seeded into 12-well plates and allowed to form a confluent layer over night. Supernatant was replaced by 3 million primary cells in a total volume of 1 ml medium and incubated with increasing concentrations of compounds for 48 h. Viability was measured using CellTiter-Blue Cell Viability Assay (Promega, Madison, Wis., USA) following the instructions of the manufacturers. Experiments with primary cells were done in triplicates, $IC_{50}$ values were calculated from the mean values of all samples used in the various experiments using GraphPad Prism 5 software.

Results and Conclusions

In an initial screening of an in-house library the compound 3-(2-napthyl)-1-(2-ethoxyphenyl)-2-propen-1-one (1) was identified as a highly potent cytotoxic agent with $IC_{50}$ values in the nanomolar range. As initial screening panel the three cell lines MEC1 (chronic lymphocytic leukemia), U-2940 (diffuse large B-cell lymphoma) and OCI-Ly7 (Non-Hodgkin lymphoma) representing B-cell neoplasms were used.

Structurally seen, the small molecule compound 1 represents a typical chalcone scaffold. It is characterized by an ortho-ethoxy-substituted phenyl part as ring A and a 2-naphthyl moiety symbolizing ring B. The focus of the present study was to guide the systematic identification of a growth inhibitor with specificity to neoplastic cells, as cytotoxicity towards healthy cells is mostly associated with adverse effects, which can be related to morbidity and mortality of the patient (Milligan D W et al. *Brit J Haematol* 2006, 135, 450-474). To discriminate in vitro between structural elements necessary for potent cytotoxicity towards tumor cells which, at the same time, clearly show less activity on normal cells, the compounds were additionally tested on the murine bone marrow fibroblast cell line M2-10B4. This cell line is regularly used as feeder layer when cultured with patient cells providing additional support and survival signals in particular in drug screens (Kurtova A V et al. *Blood* 2009, 114, 4441-4450).

Beginning with compound 1 as lead, the inventors first started with homologous variation of the 2-alkoxy substituent of ring A. In a second step, the ring B site of compound 1 was replaced and optimized (see FIG. 1). In a last set of compounds the inventors focused on the substitution pattern of ring A with respect to the ethoxy group. Three triplets including the most active compounds were generated and biologically investigated. All the compounds were obtained by base-catalyzed reaction of the corresponding acetophenone with an appropriate benzaldehyde derivative (Claisen-Schmidt condensation), as also described in Example 1 and shown in Scheme 1 above.

Initially, compounds were biologically tested in six concentration steps (0.1 µM; 1 µM; 5 µM; 10 µM; 50 µM; and 100 µM) using the CellTiter-Blue Cell Viability Assay (Promega, Madison, Wis., USA) and an incubation time of 48 hours. In case of a highly active compound ($IC_{50}<1$ µM) the tested concentration range was shifted to 0.005 µM, 0.01 µM, 0.05 µM and 0.1 µM to define the $IC_{50}$ more precisely. $IC_{50}$ values were calculated from at least two independent experiments with 3 replicates each. In order to evaluate the biologic activity of the new compounds, cytotoxicity was compared to that of fludarabine, an already approved drug for the treatment of various B-cell malignancies. The cytotoxic potential ($IC_{50}$) of fludarabine was 42.34 µM in MEC1, 1.95 µM in U-2940, and 105.50 µM in OCI-Ly7 cells, respectively. Differences in $IC_{50}$ values for the different cell types can be explained by the biological and genetic particularities of each subtype of B-cell Non-Hodgkin lymphoma (Stacchini A et al. *Leukemia Res* 1999, 23, 127-136; Sambade C et al. *Int J Cancer* 2006, 118, 555-563; Chang H et al. *Leukemia lymphoma* 1995, 19, 165-171; Tweeddale M E et al. *Blood* 1987, 69, 1307-1314; Tweeddale M et al. *Blood* 1989, 74, 572-578).

First Optimization Step

Compound 1 was used as lead structure to study the influence of the ortho-ethoxy group with respect to the biological activity. The inventors kept the 3-(2-naphthyl)-1-phenyl-2-propen-1-one backbone and started to systematically vary the substituents of ring A in position 2. Hence, the first derivatives synthesized represented the homologous series of the alkoxy substituent and started with methoxy, followed by propoxy and butoxy. The biological data (see Table 1 below) clearly showed the significance of this structural element: the methoxy derivative 2 demonstrated an almost 10-fold loss of activity on MEC1 and OCI-Ly7 cells (0.43 µM and 0.46 µM) and half of the activity towards U-2940 (4.09 µM) although the unwanted cytotoxic potential on M2-10B4 ($IC_{50}$ 41.79 µM) was reduced. Elongation of the ethoxy group of compound 1 by one more methylene group to obtain the n-propoxy derivative 3 represented only half of the cytotoxic potency on the malignant kind of cell lines (0.13 µM, 5.31 µM and 0.10 µM vs. 0.06 µM, 2.43 µM and 0.06 µM). The compound did not show any activity on the mouse fibroblast cell line up to 100 µM. The inhibition of cell growth demonstrated clear SAR depending on the length of the alkoxy chain as n-butoxy (compound 4) showed reduced activity compared to the n-propoxy compound 3. Compound 5 with an isopropoxy residue presented even weaker activity than compounds 2 and 3. Moreover, using methyl instead of an alkoxy substituent like it is the case in compound 6, the inhibitory activity on all three malignant cell lines decreased further to the lower micromolar range (6.36 µM, 10.34 µM and 4.92 µM) and also a cytotoxic potential towards M2-10B4 was observed (72.00 µM). With regard to the biological activity, already small changes of the 2-substituent of ring A considerably influenced the inhibitory activity with ethoxy being the most favorable structural feature.

Second Optimization Step

As outlined above and illustrated in FIG. 1, the second optimization step focused on a replacement of ring B. The presence of a 6-methoxy substituent on the naphthyl part (compound 7) resulted in a cell line dependent loss of activity with no cytotoxic potential on M2-10B4 cells. Further modifications of the naphthyl moiety led to compound 8 with a "dissected" aromatic ring. The vinylphenyl derivative was almost equipotent in killing U-2940 cells (2.50 µM) but less active on MEC1 and OCI-Ly7 (0.20 µM and 0.50 µM) as compared to compound 1 and did not show any activity on mouse fibroblasts. Further variations of ring B included a benzodioxole moiety (compound 9) as well as the 1-naphthyl congener of derivative 1, compound 10. Both modifications exhibited lower activity on MEC1 (1.10 µM and 1.90 µM), U-2940 (9.49 µM and 7.37 µM) and OCI-Ly7 (0.13 µM and 1.48 µM). Compound 10 showed an $IC_{50}$ value of 14.05 µM on M2-10B4 which is half as much as compound 1 (7.80 µM). The insertion of a third phenyl ring led in case of the anthracene derivative 11 to a complete loss of activity (up to 50 µM) towards all of the four cell lines whereas when having a phenanthrene moiety (compound 12) the cytotoxic activity on the malignant cell lines was retained even though a little bit lower compared to compound 1 (MEC1 1.63 µM, U2940 39.90 µM and OCI-Ly7 0.06 µM). Introduction of 5-thionaphthene and 3-thionaphthene (compound 13 and 14), respectively, resulted in a 10-fold loss of cytotoxic activity in MEC1 and OCI-Ly7 cells whereas regarding U-2940 the 3-thionaphthene 14 (0.86 µM) proved to be more potent than its congener 13 (9.05 µM). This fact applies also for the healthy fibroblasts: compound 13 (21.12 µM) shows lower and compound 14 (8.20 µM) similar activity than the lead compound 1 (7.80 µM). In compound 15 the 2-naphthyl was replaced by a 2-indole ring system which presented an improvement of the biological activity on the malignant cell lines (MEC 0.02 µM, U2940 2.90 µM and OCI-Ly7 0.05 µM). Interestingly, the compound showed less cytotoxic potential on healthy cells (19.15 µM) in comparison to compound 1 (7.80 µM). Together, from steps 1 and 2 compound 15 resulted as hit with respect to hematological B-cell malignancies.

TABLE 1

Cytotoxic activity of the compounds 1-15 on three malignant hematological cell lines (MEC1, U-2940 and OCI-Ly7) as well as the mouse fibroblast cell line (M2-10B4). For comparison, $IC_{50}$ values (in µM) upon incubation with fludarabine, an approved drug for hematologic malignancies, were 42.34 (MEC1), 1.95 (U-2940), 105.50 (OCI-Ly7), and >100 (M2-10B4), respectively.

1st optimization step

| | | $IC_{50}$ [µM] | | | |
|---|---|---|---|---|---|
| Compound | R | MEC1 | U-2940 | OCI-Ly7 | M2-10B4 |
| 1 | $OC_2H_5$ | 0.06 | 2.43 | 0.06 | 7.80 |
| 2 | $OCH_3$ | 0.43 | 4.09 | 0.46 | 41.79 |
| 3 | $OC_3H_7$ | 0.13 | 5.31 | 0.10 | >100 |
| 4 | $OC_4H_9$ | 0.70 | 5.31 | 0.12 | >100 |
| 5 | O-CH(CH₃)₂ | 1.17 | 11.13 | 0.15 | >100 |
| 6 | $CH_3$ | 6.36 | 10.34 | 4.92 | 72.00 |

2nd optimization step

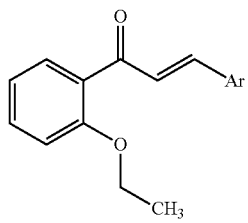

TABLE 1-continued

Cytotoxic activity of the compounds 1-15 on three malignant hematological cell lines (MEC1, U-2940 and OCI-Ly7) as well as the mouse fibroblast cell line (M2-10B4). For comparison, $IC_{50}$ values (in μM) upon incubation with fludarabine, an approved drug for hematologic malignancies, were 42.34 (MEC1), 1.95 (U-2940), 105.50 (OCI-Ly7), and >100 (M2-10B4), respectively.

| Compound | Ar | $IC_{50}$ [μM] | | | |
|---|---|---|---|---|---|
| | | MEC1 | U-2940 | OCI-Ly7 | M2-10B4 |
| 7 | 6-methoxynaphthalen-2-yl | 7.16 | 24.72 | 1.01 | >100 |
| 8 | 3-vinylphenyl | 0.20 | 2.50 | 0.50 | >100 |
| 9 | benzo[d][1,3]dioxol-5-yl | 1.10 | 9.49 | 0.13 | >100 |
| 10 | naphthalen-1-yl | 1.90 | 7.37 | 1.48 | 17.05 |
| 11 | anthracen-9-yl | >100 | >100 | >100 | nt |
| 12 | phenanthren-9-yl | 1.63 | 39.90 | 0.68 | >100 |
| 13 | benzo[b]thiophen-5-yl | 0.34 | 9.05 | 0.34 | 21.12 |
| 14 | benzo[b]thiophen-3-yl | 0.17 | 0.86 | 0.10 | 8.20 |

TABLE 1-continued

Cytotoxic activity of the compounds 1-15 on three malignant hematological cell lines (MEC1, U-2940 and OCI-Ly7) as well as the mouse fibroblast cell line (M2-10B4). For comparison, IC$_{50}$ values (in μM) upon incubation with fludarabine, an approved drug for hematologic malignancies, were 42.34 (MEC1), 1.95 (U-2940), 105.50 (OCI-Ly7), and >100 (M2-10B4), respectively.

| | | | | | |
|---|---|---|---|---|---|
| 15 | (indole structure) | 0.02 | 2.90 | 0.05 | 19.15 | nt: not tested.

Comparison of the Ortho, Meta and Para Derivatives

The position of the ethoxy group which proved as biologically advantageous in the first optimization step was systemically varied. In particular, compounds 1 (as original lead), 14 and 15 (the two most active compounds arising from the optimization process) were chosen, and the corresponding congeners were synthesized and tested. The biological results thus obtained are indicated in Table 2 below.

In all three sets the meta and para isomers were 10 to 100 fold less active than the ortho isomer. It can be clearly seen that para is being less preferred than meta which is very apparent in case of the sets of compound 1 and 15. The position of the ethoxy substituent thus plays an important role for the compounds' cytotoxic activity and ortho has been proved to be the most favored substituent position.

TABLE 2

Comparison of the biological activity of the ortho, meta and para derivatives of the three most active compounds on three malignant hematological cell lines (MEC1, U-2940 and OCI-Ly7).

| Compound | Position of the ethoxy substituent | Ar | IC$_{50}$ [μM] | | |
|---|---|---|---|---|---|
| | | | MEC1 | U2940 | OCI-Ly7 |
| 1 | ortho | naphthyl | 0.06 | 4.43 | 0.06 |
| 16 | meta | | 2.85 | 16.22 | 1.76 |
| 17 | para | | nd | nd | nd |
| 14 | ortho | benzothiophene | 0.17 | 0.86 | 0.10 |
| 18 | meta | | 2.21 | 7.59 | 1.67 |
| 19 | para | | 7.50 | 14.59 | 4.77 |
| 15 | ortho | indole | 0.02 | 2.90 | 0.05 |
| 20 | meta | | 3.33 | nd | 4.83 |
| 21 | para | | nd | nd | 25.26 | nd: no significant cytotoxic activity was detected up to 100 μM.

The cytotoxic activity of further heteroaromatic chalcone derivatives, including compounds of formula (I) according to the present invention as well as reference compounds, on the three malignant hematological cell lines MEC1, U-2940 and OCI-Ly7 is shown in the following Table 3:

TABLE 3

Cytotoxic activity of further heteroaromatic chalcone derivatives, i.e. compounds 22 to 35, on the malignant hematological cell lines MEC1, U-2940 and OCI-Ly7.

| Compound | Structure | IC50 [μM] | | |
|---|---|---|---|---|
| | | MEC1 | U-2940 | OCI-Ly7 |
| 22 | (chalcone with ortho-ethoxy phenyl and indole) | 0.05 | 1.71 | 0.03 |

TABLE 3-continued
Cytotoxic activity of further heteroaromatic chalcone derivatives, i.e. compounds 22 to 35, on the malignant hematological cell lines MEC1, U-2940 and OCI-Ly7.
| Compound | Structure | IC50 [μM] | | |
|---|---|---|---|---|
| | | MEC1 | U-2940 | OCI-Ly7 |
| 23 | 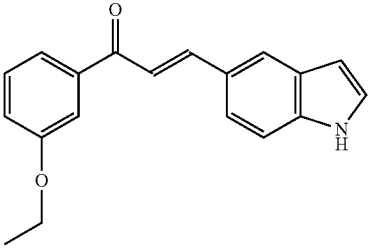 [SMILES: CCOc1cccc(C(=O)/C=C/c2ccc3[nH]ccc3c2)c1] | 2.60 | 10.04 | 1.47 |
| 24 | 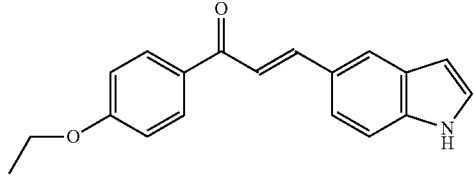 [SMILES: CCOc1ccc(C(=O)/C=C/c2ccc3[nH]ccc3c2)cc1] | 26.57 | 49.98 | 15.92 |
| 25 | 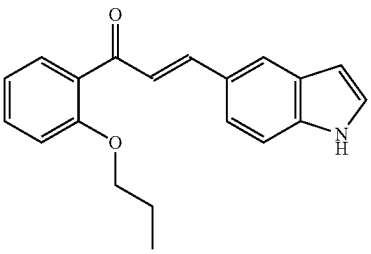 [SMILES: CCCOc1ccccc1C(=O)/C=C/c1ccc2[nH]ccc2c1] | 0.14 | 7.10 | 0.12 |
| 26 | 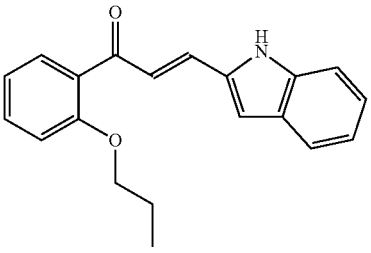 [SMILES: CCCOc1ccccc1C(=O)/C=C/c1cc2ccccc2[nH]1] | 0.04 | 10.14 | 0.08 |
| 27 | 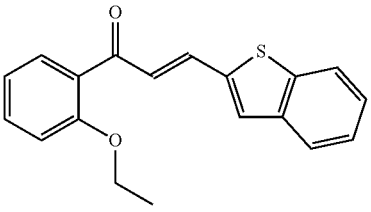 [SMILES: CCOc1ccccc1C(=O)/C=C/c1cc2ccccc2s1] | 0.06 | 2.31 | 0.07 |
| 28 | 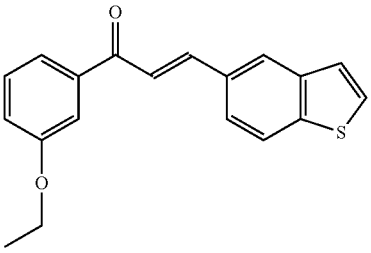 [SMILES: CCOc1cccc(C(=O)/C=C/c2ccc3sccc3c2)c1] | 5.48 | 12.89 | 4.78 |

TABLE 3-continued
Cytotoxic activity of further heteroaromatic chalcone derivatives, i.e. compounds 22 to 35, on the malignant hematological cell lines MEC1, U-2940 and OCI-Ly7.
| Compound | Structure | IC50 [μM] | | |
| --- | --- | --- | --- | --- |
| | | MEC1 | U-2940 | OCI-Ly7 |
| 29 | 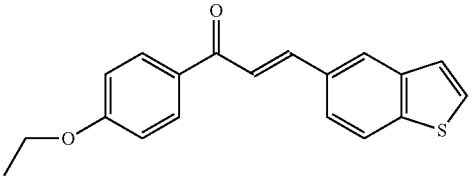 [SMILES: CCOc1ccc(C(=O)/C=C/c2ccc3sccc3c2)cc1] | 230.89 | nd | nd |
| 30 | 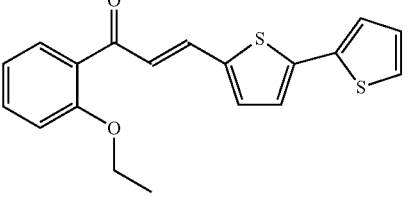 | 0.02 | 3.13 | 0.02 |
| 31 | 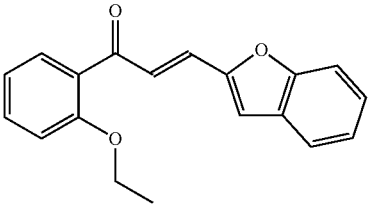 [SMILES: CCOc1ccccc1C(=O)/C=C/c1cc2ccccc2o1] | 0.20 | 7.10 | 0.05 |
| 32 | 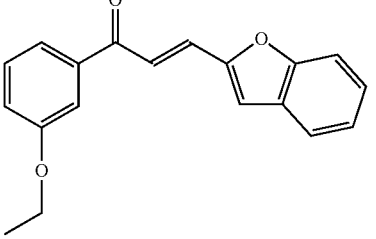 | 6.91 | 44.32 | 16.66 |
| 33 | 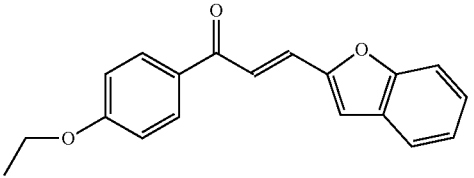 [SMILES: CCOc1ccc(C(=O)/C=C/c2cc3ccccc3o2)cc1] | 38.79 | 42.17 | 19.49 |
| 34 | 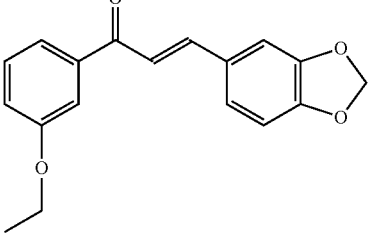 | 8.73 | 18.79 | 6.35 |

TABLE 3-continued

Cytotoxic activity of further heteroaromatic chalcone derivatives, i.e. compounds 22 to 35, on the malignant hematological cell lines MEC1, U-2940 and OCI-Ly7.

| Compound | Structure | IC50 [µM] | | |
|---|---|---|---|---|
| | | MEC1 | U-2940 | OCI-Ly7 |
| 35 | (structure) | 34.32 | 56.20 | 19.04 | nd: no significant cytotoxic activity was detected up to 100 µM.

Together, compound 15 developed by two lead optimization processes turned out to have the optimal structural requirements for potent inhibition of malignant hematological cell lines with less biological activity on normal mouse fibroblasts. Especially in conjunction with chalcone derivatives, the 3,4,5-trimethoxyphenyl moiety was previously described as an essential structural feature of potent cytotoxic compounds (Das U et al. Bioorg Med Chem 2009, 17, 3909-15; Dimmock J R et al. Bioorg Med Chem Lett 2005, 15, 1633-6; Romagnoli R et al. Bioorg Med Chem 2008, 16, 5367-76; Schobert R et al. J Med Chem 2009, 52, 241-6). Also in the case of other small molecules, for example 1,5-diaryl imidazole derivatives, this substitution pattern of the aromatic site proved to be most favored (Bellina F et al. Bioorg Med Chem Lett 2006, 16, 5757-62). In the context of the present invention, however, the 2-ethoxyphenyl moiety (as comprised in compounds 14 and 15) has been identified as a novel highly active structural principle in cytotoxic chalcone derivatives, including in particular the compounds of formula (I) according to the invention. Biological investigation of the homologous series of this structural feature proved the ethoxy substituent as most preferred. A recent study conducted by Maioral et al. investigating apoptosis induction of 1-naphthylchalcones in human acute leukemia cell lines described the derivative with a 2,5-dimethoxy substituent on the site of ring A as the most potent cytotoxic representative of the series tested with an $IC_{50}$ value of 40.12 µM on K562 and 20.98 µM on Jurkat cells after 24 hours of incubation (Maioral M F et al. Biochimie 2013, 95(4), 866-74). Moreover, the compound showed to be non-toxic to peripheral blood lymphocytes with a cell viability of 99.89±10.69% at 50 µM compound concentration after 24 hours. These data can be seen in accordance with the results presented herein: the 1-naphthylchalcone with a 2-methoxy substituent on ring A proved to be the most potent one. However, through optimization of both ring A and ring B in the context of the present invention, an even more potent cytotoxic compound on hematological cell lines has been obtained.

Effect of Compound 15 on Other Hematological Cell Lines

Hematologic malignancies are highly heterogeneous in their biology and behavior. This and the fact that some patient groups are resistant to therapy underlines the urgent need for new therapeutic drugs. Compound 15 has therefore been tested on other cell lines representing a variety of hematologic neoplasms: two T-cell acute leukemia cell lines (CCRF, Jurkat), two myeloid leukemia cell lines (HL60, K562), and two additional B-cell lines (SU-DHL6, SU-DHL9). Viability was assessed as described in the methods section above. The results obtained in these tests are shown in FIG. 2. Compound 15 considerably reduced the viability of the hematologic cell lines to less than 30% of control already at concentrations<1 µM. An exception was the chronic myeloid leukemia line K562. Although viability was reduced down to 60% already at low concentrations, toxicity did not increase at increasing concentrations of compound 15 in this cell line (see FIG. 2). However, this cell line derives from a patient in blast crisis and is characterized by a number of genetic aberrations associated with aggressive disease and resistance to treatment (Drexler H G. K-562. In: The Leukemia-Lymphoma Cell Line FactsBook, Drexler H G (ed.), Academic Press: London, 2001; pp. 632-633). In all other cell lines, the biologic activity of compound 15 reached levels comparable to standard drugs used in therapy (Beesley A H et al. Brit J Cancer 2006, 95, 1537-1544; Tang R et al. BMC Cancer 2008, 8, 51; Lubgan D et al. Cell Mol Biol Lett 2009, 14, 113-127; Parker B W et al. Blood 1998, 91, 458-465; Dohse M et al. Drug Metab Dispos 2010, 38, 1371-1380; Weisberg E et al. Cancer Cell 2005, 7, 129-141; Czyzewski K et al. Neoplasma 2009, 56, 202-207). $IC_{50}$ values for compound 15 are listed in Table 4.

TABLE 4

$IC_{50}$ values (in µM) determined for compound 15 in different cell types. For comparison, the standard therapeutic drug fludarabine was tested in parallel in experiments using primary cells.

| | CCRF | Jurkat | HL60 | K562 | SU-DHL6 | SU-DHL9 | CLL Suspension | HD Suspension | CLL Co-culture |
|---|---|---|---|---|---|---|---|---|---|
| 15 | 0.03 | 0.04 | 0.02 | nd | 0.06 | 0.03 | 1.18 | 13.56 | 0.68 |
| Fludarabine | nd | nd | nd | nd | nd | nd | 1.85 | 13.87 | 10.22 |

CCRF, Jurkat: T-cell acute leukemia; HL60, K562: myeloid leukemia; SU-DHL6, SU-DHL9: B-cell lymphoma; CLL Suspension: primary CLL cells in suspension culture; HD Suspension: healthy donor cells in suspension culture; CLL co-culture: CLL cells in co-culture with M2-10B4 fibroblast cells; nd: no significant cytotoxic activity was detected up to 100 µM.

Comparison of Compound 15 with Fludarabine on MEC1, OCI-Ly7 and U2940

To put the efficacy of compound 15 into perspective, the inventors screened the cell lines of their screening panel also with fludarabine, i.e. [(2R,3R,4S,5R)-5-(6-amino-2-fluoro-purin-9-yl)-3,4-dihydroxy-oxolan-2-yl]methoxyphosphonic acid, which is a purine analog used in treatment regimens for a variety of indolent Non-Hodgkin lymphomas, for instance chronic lymphocytic leukemia (CLL). As shown in FIG. 3, compound 15 displayed much higher toxicity as compared to fludarabine in MEC1 and OCI-Ly cells and, furthermore, it had comparable efficacy in U-2940 cells. This is also reflected by the corresponding $IC_{50}$ values which were 1-3 log smaller for compound 15 as compared to fludarabine ($IC_{50}$ values were 0.02 µM and 42.34 µM (MEC1), 0.05 µM and 1.95 µM (U-2940), 2.90 µM and 105.50 µM (OCI-Ly7) for compound 15 and fluudarabine, respectively). Notably, while fludarabine had variable impact on viability in these 3 cell lines, the effect of compound 15 was more consistent. This not only reflects the biological and genetic differences involved, but also indicates a high therapeutic potential of compound 15 in antitumor regimens (Stacchini A et al. *Leukemia Res* 1999, 23, 127-136; Sambade C et al. *Int J Cancer* 2006, 118, 555-563; Chang H et al. *Leukemia lymphoma* 1995, 19, 165-171; Tweeddale M et al. *Blood* 1989, 74, 572-578).

Investigating the Effect of Compound 15 in Primary Cells

As a last step, it has been sought to evaluate the cytotoxicity of compound 15 in primary cells and compare its activity to the impact of fludarabine. To this end, peripheral blood mononuclear cells (PBMC) of chronic lymphocytic leukemia (CLL) patients were used in two experimental settings. They were cultured in conventional suspension culture being exposed to increasing concentrations of drug. However, CLL cells need close contact to the tumor microenvironment depending on and receiving survival signals from stromal cells which has impact on response to therapy. Therefore, as a second approach, CLL cells were cultured over a layer of mouse fibroblasts (M2-10B4) to include this biological aspect in drug evaluation. Such an approach is often used in pre-clinical assessment and testing of drugs in CLL cells (Kurtova A V et al. *Blood* 2009, 114, 4441-4450). Cells from healthy donors (HD) were included as control.

FIG. 4 shows the reduction of viability in the tested settings, and Table 4 (above) lists the $IC_{50}$ values for both compound 15 and fludarabine in CLL and HD primary cells. Higher cytotoxicity of compound 15 was observed in PBMC from CLL as compared to HD in suspension culture (see FIGS. 4A and 4B). Also, in comparison, fludarabine had less effect in tumor cells and displayed a greater reduction of viability in healthy cells. This indicates a more favorable therapeutic ratio for compound 15. In co-culture, a protective effect for CLL cells usually is observed, also in the present experiments with fludarabine (see FIG. 4C). In contrast, when incubated with compound 15, CLL cells showed a similar reduction in viability as in suspension culture. Again, this indicates a high therapeutic potential of this novel compound.

Example 3: Combined Treatment of CLL Primary Cells with a Compound of Formula (I) and Further Anticancer Agents To further explore the therapeutic potential of the compounds of formula (I) according to the present invention, compound 15 was tested in combination with three anticancer agents—i.e., ABT199, CAL101 (idealisib), or PCI32765 (ibrutinib)—which are currently tested in clinical studies for CLL and other B-cell malignancies. ABT199 is a BCL2 inhibitor, CAL101 a PI3Kδ inhibitor, and PCI32765 a BTK inhibitor. ABT199 is being used in various neoplasms where overexpression of BCL2 has been reported. Both CAL101 and PCI32765 target signaling pathways, PCI132765 the B-cell receptor pathway plus several other less defined kinases, CAL101 also the B-cell receptor pathway and in addition several other signaling pathways involving cytokines, hormones and other factors. Both drugs are tested in clinical studies in indolent B-cell malignancies.

Peripheral blood mononuclear cells (PBMCs) of CLL patients were incubated in increasing concentrations of one of the above-mentioned anticancer agents alone or increasing anticancer agent concentrations plus compound 15 in two different concentrations under standard conditions for 48 h before viability was determined (CellTiterBlue, Promega). Primary cells from 5 (ABT199) or 6 patients (CAL101, PCI32765) were included.

It was found that the addition of compound 15 to the different anticancer agents added to the cytotoxic effect of the respective anticancer agent alone, providing a synergistic effect, as also shown in FIGS. 5A to 5C. In all cases, higher concentrations of compound 15 also led to higher synergistic toxicities.

These results indicate that compound 15 enhances the cytotoxic effect of the tested anticancer agents ABT199, CAL101 and PCI32765. The compounds of formula (I), such as compound 15, are thus advantageous for combination treatments with a further anticancer agent (such as, e.g., ABT199, CAL101 or PCI32765), particularly for the therapy of chronic lymphoid leukemia (CLL). In addition, the compounds of formula (I) are also advantageous, e.g., as novel, single drug options for relapsed and/or refractory patients.

The invention claimed is:
1. A compound of formula (I)

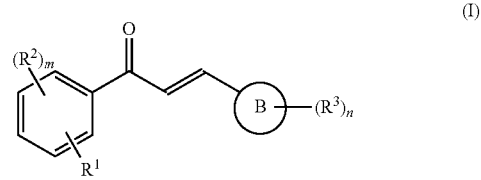

wherein:
$R^1$ is $C_{2-6}$ alkoxy;
each $R^2$ is independently selected from the group consisting of $C_{1-6}$ alkyl, $C_{2-6}$ alkenyl, $C_{2-6}$ alkynyl, —OH, —O($C_{1-6}$ alkyl), —O($C_{1-6}$ alkyl)-OH, —O($C_{1-6}$ alkyl)-O($C_{1-6}$ alkyl), —SH, —S($C_{1-6}$ alkyl), —S($C_{1-6}$ alkyl)-SH, —S($C_{1-6}$ alkyl)-S($C_{1-6}$ alkyl), —NH$_2$, —NH($C_{1-6}$ alkyl), —N($C_{1-6}$ alkyl)($C_{1-6}$ alkyl), halogen, —CF$_3$, —CN, —NO$_2$, —N$_3$, —CHO, —CO—($C_{1-6}$ alkyl), —COOH, —CO—O—($C_{1-6}$ alkyl), —O—CO—($C_{1-6}$ alkyl), —CO—NH$_2$, —CO—NH($C_{1-6}$ alkyl), —CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —SO$_2$—NH$_2$, —SO$_2$—NH($C_{1-6}$ alkyl), —SO$_2$—N($C_{1-6}$ alkyl)($C_{1-6}$ alkyl), —NH—SO$_2$—($C_{1-6}$ alkyl), and —N($C_{1-6}$ alkyl)-SO$_2$—($C_{1-6}$ alkyl);

each R³ is independently selected from the group consisting of C₁₋₆ alkyl, C₂₋₆ alkenyl, C₂₋₆ alkynyl, —OH, —O(C₂₋₆ alkyl), —O(C₁₋₆ alkyl)-OH, —O(C₁₋₆ alkyl)-O(C₁₋₆ alkyl), —SH, —S(C₁₋₆ alkyl), —S(C₁₋₆ alkyl)-SH, —S(C₁₋₆ alkyl)-S(C₁₋₆ alkyl), —NH₂, —NH(C₁₋₆ alkyl), —N(C₁₋₆ alkyl)(C₁₋₆ alkyl), halogen, —CF₃, —CN, —NO₂, —N₃, —CHO, —CO—(C₁₋₆ alkyl), —COOH, —CO—O—(C₁₋₆ alkyl), —O—CO—(C₁₋₆ alkyl), —CO—NH₂, —CO—NH(C₁₋₆ alkyl), —CO—N(C₁₋₆ alkyl)(C₁₋₆ alkyl), —NH—CO—(C₁₋₆ alkyl), —N(C₁₋₆ alkyl)-CO—(C₁₋₆ alkyl), —SO₂—NH₂, —SO₂—NH(C₁₋₆ alkyl), —SO₂—N(C₁₋₆ alkyl)(C₁₋₆ alkyl), —NH—SO₂—(C₁₋₆ alkyl), —N(C₁₋₆ alkyl)-SO₂—(C₁₋₆ alkyl), optionally substituted aryl and optionally substituted heteroaryl, wherein said aryl or said heteroaryl is optionally substituted with one or more groups independently selected from the group consisting of C₁₋₄ alkyl, halogen, —CF₃, —CN, —OH, —O(C₁₋₄ alkyl), —NH₂, —NH(C₁₋₄ alkyl), and —N(C₁₋₄ alkyl)(C₁₋₄ alkyl);

B is benzoheteroaryl, wherein the heteroaryl moiety comprised in said benzoheteroaryl is a monocyclic heteroaryl moiety having 5 ring atoms, wherein 1 or 2 ring atoms are each independently selected from the group consisting of oxygen, sulfur and nitrogen and the other ring atoms are carbon atoms, and further wherein B is not 1H-indol-3-yl or indazolyl;

m is an integer of 0 to 4; and n is an integer of 0 to 4;

or a pharmaceutically acceptable salt or solvate thereof.

2. The compound of claim 1, wherein R¹ is ethoxy.

3. The compound of claim 1, wherein R¹ is in ortho-position with respect to the carbonyl group.

4. The compound of claim 1, wherein each R² is independently selected from the group consisting of C₁₋₄ alkyl, halogen, —CF₃, —CN, —OH, —O(C₁₋₄ alkyl), —NH₂, —NH(C₁₋₄ alkyl), and —N(C₁₋₄ alkyl)(C₁₋₄ alkyl).

5. The compound of claim 1, wherein each R³ is independently selected from the group consisting of C₁₋₄ alkyl, halogen, —CF₃, —CN, —OH, —O(C₂₋₄ alkyl), —NH₂, —NH(C₁₋₄ alkyl), and —N(C₁₋₄ alkyl)(C₁₋₄ alkyl).

6. The compound of claim 1, wherein B is benzoheteroaryl, wherein the heteroaryl moiety comprised in said benzoheteroaryl is a monocyclic heteroaryl moiety having 5 ring atoms, wherein 1 or 2 ring atoms are each independently selected from the group consisting of oxygen, sulfur and nitrogen and the other ring atoms are carbon atoms, wherein said benzoheteroaryl is attached to the remainder of the compound of formula (I) via the heteroaryl moiety comprised in said benzoheteroaryl, and further wherein B is not 1H-indol-3-yl or indazolyl.

7. The compound of claim 1, wherein B is 1H-indol-2-yl, 1H-indol-5-yl, benzo[b]thienyl, or benzofuranyl.

8. The compound of claim 1, wherein B is 1H-indol-2-yl, 2-benzo[b]thienyl, 3-benzo[b]thienyl, benzofuran-2-yl, or benzofuran-3-yl.

9. The compound of claim 1, wherein said compound is a compound of one of the following formulae 13 to 15, 18 to 29 or 31 to 33:

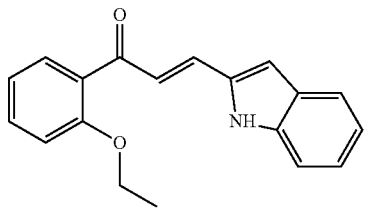
15

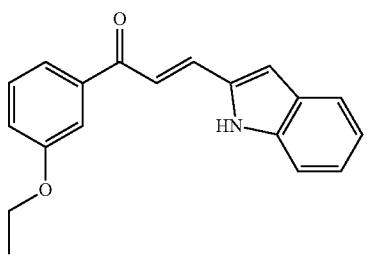
20

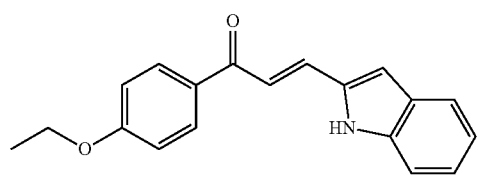
21

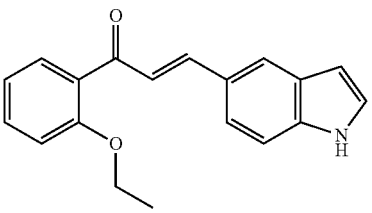
22

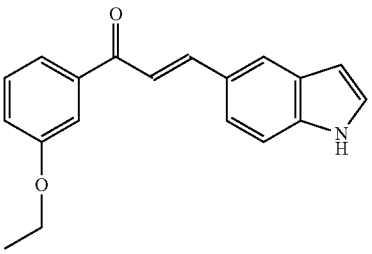
23

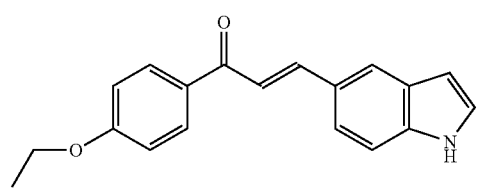
24

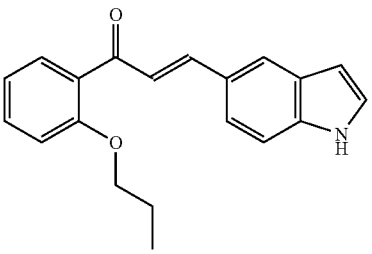
25

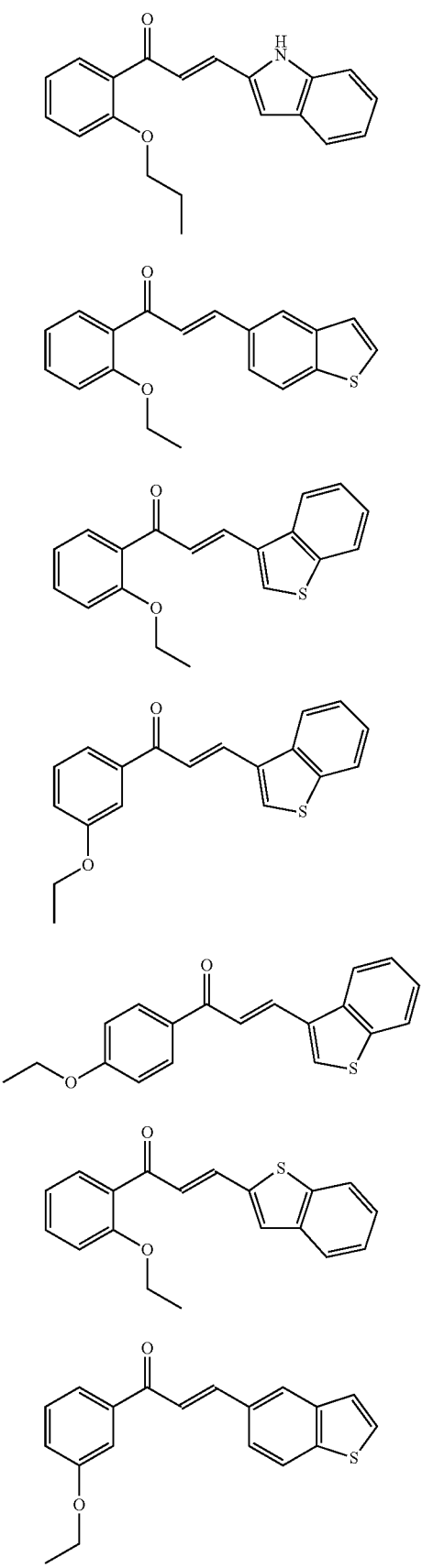

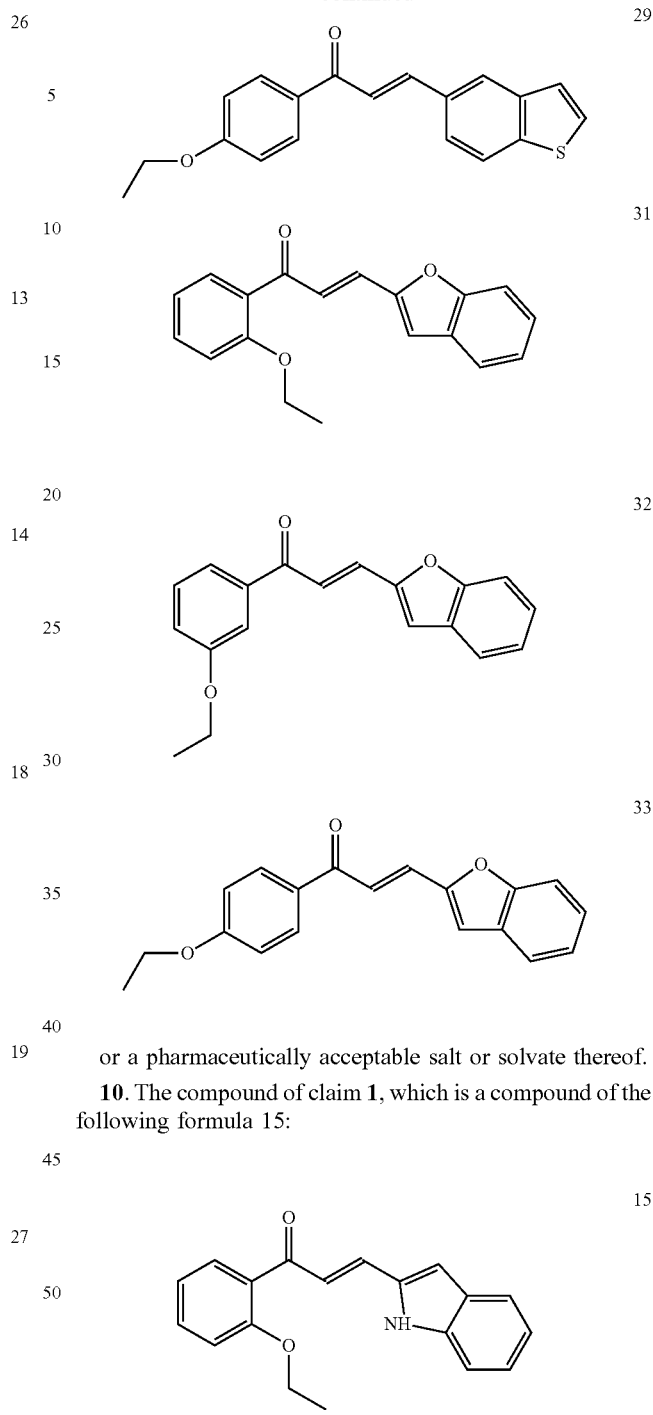

or a pharmaceutically acceptable salt or solvate thereof.

10. The compound of claim 1, which is a compound of the following formula 15:

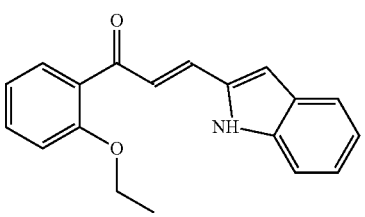

or a pharmaceutically acceptable salt or solvate thereof.

11. A pharmaceutical composition comprising the compound of claim 1 and a pharmaceutically acceptable excipient.

12. A method of treating cancer selected from the group consisting of acute leukemia, chronic lymphocytic leukemia and B-cell lymphoma, the method comprising the administration of a therapeutically effective amount of a compound of the following formula (I) or a pharmaceutically acceptable salt or solvate thereof, to a subject in need thereof:

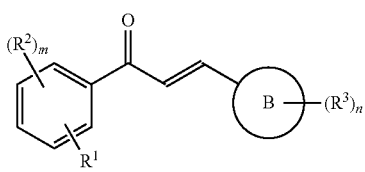

(I)

wherein:

$R^1$ is $C_{2-6}$ alkoxy;

each $R^2$ is independently selected from the group consisting of $C_{1-6}$ alkyl, $C_{2-6}$ alkenyl, $C_{2-6}$ alkynyl, —OH, —O($C_{1-6}$ alkyl), —O($C_{1-6}$ alkyl)-OH, —O($C_{1-6}$ alkyl)-O($C_{1-6}$ alkyl), —SH, —S($C_{1-6}$ alkyl), —S($C_{1-6}$ alkyl)-SH, —S($C_{1-6}$ alkyl)-S($C_{1-6}$ alkyl), —NH$_2$, —NH($C_{1-6}$ alkyl), —N($C_{1-6}$ alkyl)($C_{1-6}$ alkyl), halogen, —CF$_3$, —CN, —NO$_2$, —N$_3$, —CHO, —CO—($C_{1-6}$ alkyl), —COOH, —CO—O—($C_{1-6}$ alkyl), —O—CO—($C_{1-6}$ alkyl), —CO—NH$_2$, —CO—NH($C_{1-6}$ alkyl), —CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —SO$_2$—NH$_2$, —SO$_2$—NH($C_{1-6}$ alkyl), —SO$_2$—N($C_{1-6}$ alkyl)($C_{1-6}$alkyl), —NH—SO$_2$—($C_{1-6}$ alkyl), and —N($C_{1-6}$ alkyl)-SO$_2$—($C_{1-6}$ alkyl);

each $R^3$ is independently selected from the group consisting of $C_{1-6}$ alkyl, $C_{2-6}$ alkenyl, $C_{2-6}$ alkynyl, —OH, —O($C_{1-6}$ alkyl), —O($C_{1-6}$ alkyl)-OH, —O($C_{1-6}$ alkyl)-O($C_{1-6}$ alkyl), —SH, —S($C_{1-6}$ alkyl), —S($C_{1-6}$ alkyl)-SH, —S($C_{1-6}$ alkyl)-S($C_{1-6}$ alkyl), —NH$_2$, —NH($C_{1-6}$ alkyl), —N($C_{1-6}$ alkyl)($C_{1-6}$ alkyl), halogen, —CF$_3$, —CN, —NO$_2$, —N$_3$, —CHO, —CO—($C_{1-6}$ alkyl), —COOH, —CO—O—($C_{1-6}$ alkyl), —O—CO—($C_{1-6}$ alkyl), —CO—NH$_2$, —CO—NH($C_{1-6}$ alkyl), —CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —SO$_2$—NH$_2$, —SO$_2$—NH($C_{1-6}$ alkyl), —SO$_2$—N($C_{1-6}$ alkyl)($C_{1-6}$ alkyl), —NH—SO$_2$—($C_{1-6}$ alkyl), —N($C_{1-6}$ alkyl)-SO$_2$—($C_{1-6}$ alkyl), optionally substituted aryl and optionally substituted heteroaryl, wherein said aryl or said heteroaryl is optionally substituted with one or more groups independently selected from the group consisting of $C_{1-4}$ alkyl, halogen, —CF$_3$, —CN, —OH, —O($C_{1-4}$ alkyl), —NH$_2$, —NH($C_{1-4}$ alkyl), and —N($C_{1-4}$ alkyl)($C_{1-4}$ alkyl);

B is benzoheteroaryl, wherein the heteroaryl moiety comprised in said benzoheteroaryl is a monocyclic heteroaryl moiety having 5 ring atoms, wherein 1 or 2 ring atoms are each independently selected from the group consisting of oxygen, sulfur and nitrogen and the other ring atoms are carbon atoms;

m is an integer of 0 to 4; and n is an integer of 0 to 4.

13. The method of claim 12, wherein the method comprises administering the compound in combination with an anticancer drug and/or in combination with radiotherapy.

14. The method of claim 12, wherein the subject is a human.

* * * * *